US008524249B2

(12) United States Patent
Gomis et al.

(10) Patent No.: US 8,524,249 B2
(45) Date of Patent: Sep. 3, 2013

(54) VACCINES FOR INCLUSION BODY HEPATITIS

(75) Inventors: Susantha Gomis, Saskatoon (CA); Suresh Kumar Tikoo, Saskatoon (CA); Davor Ojkic, Guelph (CA)

(73) Assignees: University of Saskatchewan, Saskatoon (CA); University of Guelph, Guelph (CA)

( * ) Notice: Subject to any disclaimer, the term of this patent is extended or adjusted under 35 U.S.C. 154(b) by 13 days.

(21) Appl. No.: 12/969,444

(22) Filed: Dec. 15, 2010

(65) Prior Publication Data

US 2011/0165224 A1 Jul. 7, 2011

Related U.S. Application Data

(60) Provisional application No. 61/286,664, filed on Dec. 15, 2009.

(51) Int. Cl.
*A61K 39/295* (2006.01)
*A61K 39/235* (2006.01)

(52) U.S. Cl.
USPC .............. 424/233.1; 424/202.1; 424/93.1

(58) Field of Classification Search
None
See application file for complete search history.

(56) References Cited

U.S. PATENT DOCUMENTS

| | | | |
|---|---|---|---|
| 4,751,079 A | 6/1988 | Burger et al. | |
| 5,037,650 A | 8/1991 | Schrier | |
| 5,750,101 A | 5/1998 | Stone | |
| 5,817,320 A | 10/1998 | Stone | |
| 5,906,821 A | 5/1999 | Griffin et al. | |
| 5,914,113 A | 6/1999 | Schrier | |
| 6,048,535 A | 4/2000 | Sharma | |
| 6,203,801 B1 | 3/2001 | Schaap et al. | |
| 6,204,045 B1 | 3/2001 | Griffin et al. | |
| 6,241,991 B1 | 6/2001 | Paul et al. | |
| 6,406,702 B1 | 6/2002 | Sharma | |
| 6,410,222 B1 | 6/2002 | Yokogawa et al. | |
| 6,680,061 B1 | 1/2004 | Schaap et al. | |
| 6,951,650 B1 | 10/2005 | van Loon | |
| 7,150,873 B2 | 12/2006 | Schaap et al. | |
| 2004/0058441 A1 | 3/2004 | Pain et al. | |
| 2007/0178115 A1 | 8/2007 | Tang et al. | |
| 2007/0243199 A1 | 10/2007 | Doelling et al. | |
| 2007/0243212 A1 | 10/2007 | Doelling et al. | |
| 2009/0239297 A1 | 9/2009 | Pain et al. | |

FOREIGN PATENT DOCUMENTS

| | | |
|---|---|---|
| CA | 1189450 C | 6/1985 |
| CA | 2216410 C | 3/1998 |
| CA | 1339963 C | 7/1998 |
| CA | 2285136 C | 4/2000 |
| CA | 2320414 A1 | 6/2000 |
| JP | 1272529 A | 10/1999 |
| WO | WO9535121 A1 | 12/1995 |
| WO | WO9856413 A1 | 12/1998 |
| WO | WO03039593 A1 | 5/2003 |
| WO | WO03076601 A1 | 9/2003 |
| WO | WO2004030614 A2 | 4/2004 |
| WO | WO2007022151 A2 | 2/2007 |
| WO | WO2007126816 A2 | 11/2007 |
| WO | WO2008076518 A2 | 6/2008 |
| WO | WO2008129058 A1 | 10/2008 |

OTHER PUBLICATIONS

Gomis, S. et al. (2006) "Inclusion Body Hepatitis as a primary disease in broilers in Saskatchewan, Canada", Avian Diseases, 50:550.
Ojkic, D. et al. (2008) "Genotyping of Canadian isolates of of fowl adenoviruses", Avian Pathology, 37(1):95-100.
GenBank Accession No. EF685508.1, "Fowl adenovirus E isolate 04-53357-74 hexon protein gene, partial cds", nucleotide sequence.
GenBank Accession No. EF685492.1, "Fowl adenovirus DD0-2007 isolate 04-53357-119 hexon protein gene, partial cds", nucleotide sequence.
GenBank Accession No. EF685580.1, "Fowl adenovirus D isolate 06-58730 hexon protein gene, partial cds", nucleotide sequence.
GenBank Accession No. EF685486.1, "Fowl adenobirus E isolate 04-53357-125 hexon protein gene, partial cds", nucleotide sequence.
Grimes, T.M. (1992) "Cause and control of peracute form of inclusion body hepatitis", Proc. 41st West. Poult. Dis. Conf., Sacramento, CA, 42-44.
Grimes, T.M. (2007) "Inclusion body hepatitis of chickens-occurence and control." Proc. 56th West. Poult. Dis. Conf., Las Vegas, Nevada, 42-46.
Intervet Australia, Pvt. Ltd., "Intervet Nobilis FAV Vaccine", Fowl Adenovirus, living (Esurient strain), Product Label, APVMA Approval No. 52390/1000D/1106.
Intervet Australia, Pvt. Ltd., "Intervet FAV Vaccine: Prime protection for the prevention of Inclusion Body Hepatitis caused by FAV-8", Informational Product Guide, 1-3.
Gomis, S. et al. (Sep. 30, 2008) "Inclusion body hepatitis is a primary disease in broilers in Canada", 19th Western Meeting of Poultry Clinicians and Pathologists "WestVet 19", Lake Louise, Alberta.
Gomis, S. et al. (Jun. 29-Jul. 4, 2008) "Inclusion body hepatitis is a primary disease in Saskatchewan and Alberta, Canada", XXIII World Poultry Congress, Brisbane, Australia.
Ekanayake S. et al. (Jul. 19-23, 2008) "Experimental reproduction of inclusion body hepatitis in boiler chickens", American Association of Avian Pathologists/American Veterniary Medical Association, New Orleans, Louisiana.
Grimes, T. M. et al. (1977a). Virus-neutralizing antibody titers against 8 avian adenovirus serotypes in breeder hens in Georgia by a microneutralization procedure. Avian Dis. 21(2): 220-9.
Grimes, T. M. et al. (1978a). Comparative study of experimental inclusion body hepatitis of chickens caused by serotypes of avian adenovirus Vet. Pathol. 15: 249-263.

(Continued)

*Primary Examiner* — Bao Li
(74) *Attorney, Agent, or Firm* — Bereskin & Parr LLP; Micheline Gravelle; Carmela DeLuca

(57) ABSTRACT

A composition comprising an isolated fowl adenovirus (FAdV), wherein the FAdV is a strain selected from FAdV-2, FAdV-7, FAdv-8a, FAdV-8b, FAdV-8a/8b or FAdV-11 serotype strains; and a suitable carrier and methods for inducing protective immunity in a subject and/or its progeny.

30 Claims, 11 Drawing Sheets

(56) References Cited

OTHER PUBLICATIONS

Figure 1:
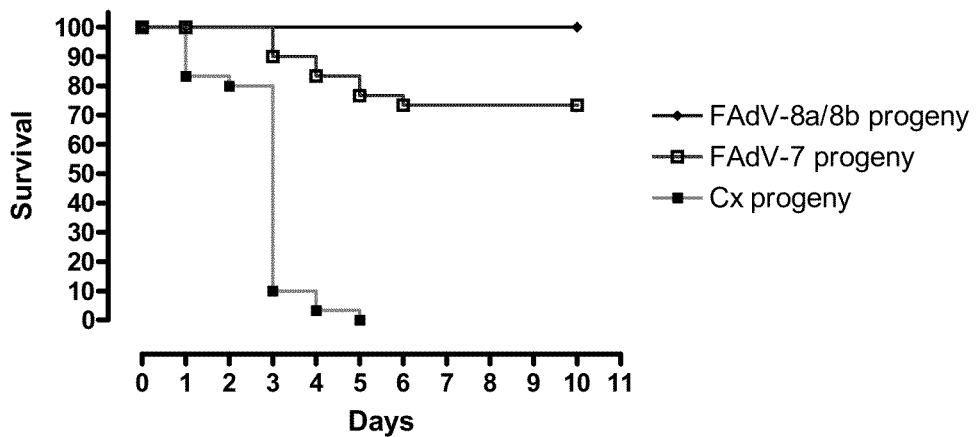

Grimes, T. M., and King, D. J. (1977a). Effects of maternal antibody on experimental infections of chickens with type-8 avian adenovirus. Avian Dis. 21: 97-112.

Grimes, T. M., and King, D. J. (1977b). Serotyping avian adenoviruses by a microneutralization procedure. Am. J. Vet. Res. 38(3): 317-321.

Grimes, T. M. et al. (1978b). Serologic and pathogenicity studies of avian adenovirus isolated from chickens with inclusion body hepatitis. Avian Dis. 22: 177-180.

Grimes, T. M. et al. (1977b). Involvement of a type-8 avian adenovirus in the etiology of inclusion body hepatitis. Avian Dis. 21(1): 26-38.

Ekanayake S. (Jan. 6, 2010) "Inclusion body hepatitis as a primary disease in commercial broiler chickens",. M. Sc. Thesis, University of Saskatchewan.

Grimes, T. (2007) "Inclusion Body Hepatitis of Chickens—Occurence and Control in Australia", 56th Western Poultry Disease Conference 2007.

Matthews, T.D. (2005) "Protection of broiler breeders against a strain of fowl adenovirus and characterization of several fowl adenovirus serotypes", M.Sc. Thesis, University of Georgia.

Alvarado I.R. et al. (2007) "Genetic characterization, pathogenicity, and protection studies with an avian adenovirus isolate associated with inclusion body hepatitis", Avian Diseases Digest, 2(1): e-5.

GenBank Accession No. ABS81119.1, "Hexon Protein [fowl adenovirus DDO-2007]".

GenBank Accession No. EF685489.1, "Fowl adenovirus DDO-2007 isolate 04-53357-122 hexon protein gene, partial cds".

VACCINES FOR INCLUSION BODY HEPATITIS

CROSS REFERENCE TO RELATED APPLICATIONS

This application claims the benefit of 35 U.S.C. 119 based on the priority of corresponding U.S. Provisional Patent Application No. 61/286,664 filed Dec. 15, 2009, which is incorporated herein in its entirety.

INCORPORATION OF SEQUENCE LISTING

A computer readable form of the Sequence Listing "13764-117_SequenceListing.txt" ( 41.183 bytes), submitted via EFS-WEB and created on Feb. 15, 2011, is herein incorporated by reference.

FIELD OF THE DISCLOSURE

The disclosure pertains to methods and compositions for inducing an immune response against fowl adenovirus (FAdV) infection and particularly to methods and compositions for inducing immune protection in poultry from infection with FAdV to prevent inclusion body hepatitis.

BACKGROUND OF THE DISCLOSURE

Inclusion body hepatitis (IBH) is an economically important, emerging problem in broiler chickens in several geographical regions in Southeast Asia, Europe, Middle East, Europe, Australia, New Zealand, North America, Mexico, Central and South America (Gomis et al., 2006; Ojkic et al., 2008b). Historically, IBH has been identified as a secondary disease in broiler chickens associated with common immunosuppressive agents such as infectious bursal disease virus (IBDV) and chicken anemia virus (CAV) (Gomis et al., 2006). Pathogenesis of IBH is not clear due to multiple factors associated with its host, pathogen and the environment (Erny et al., 1991; Gomis et al., 2006; Grimes, 1992; 2007; Mendelson et al., 1995).

The disease is manifested as sudden onset of increased mortality of 1-10% (Gomis et al., 2006), and occasionally exceeding 30-40% (Barr and Scott, 1988; Erny et al., 1991), with a short clinical course of 4-5 days. Inclusion body hepatitis (IBH) is an acute viral disease of 2-7 week old broiler chickens (Adair and Fitzgerald, 2008). The affected chickens typically have pale, friable, swollen livers with focal to extensive necrosis, and large basophilic INIB in hepatocytes (Reece et al., 1986a). Since the initial studies, IBH has been reported in North America (Alvarado et al., 2007; El-Attrache and Villegas, 2001; Gomis et al., 2006; Ojkic et al., 2008b), Mexico (Antillon and Lucio, 1974; Sarfati, 1991), Europe (Hoffman et al., 1975; Young et al., 1972), Japan (Itakura et al., 1974b; Otsuki et al., 1976), New Zealand (Christensen and Saifuddin, 1989), Australia (Grimes, 1992; Reece et al., 1986a; Wells et al., 1977), and several Latin American countries (Toro et al., 1999). Control of IBH has been attempted in several countries by vaccination of boiler breeders and broilers with inactivated, autogenous vaccines (Alvarado et al., 2007; Cowen, 1992).

A fowl adenovirus serotype-5 (FAdV-5), Tipton strain was incriminated in the etiology of IBH (Bickford, 1972; Fadly and Winterfield, 1973; McFerran et al., 1976b; Rosenberger et al., 1974). Thereafter, all other serotypes of FAdV have been associated with outbreaks of IBH in chickens: FAdV-1 (Singh et al., 1996); FAdV-2 (Philippe et al., 2005); FAdV-3 and FAdV-4 (Grimes and King, 1977a); (McFerran et al., 1976b); FAdV-4 (Mazaheri et al., 1998); FAdV-6, FAdV-7, FAdV-8, FAdV-8a, FAdV-8b and FAdV-11 (Grimes et al., 1977b; Kefford and Borland, 1979; Ojkic et al., 2005; Ojkic et al., 2008a); FAdV-9 (Grimes et al., 1978b); FAdV-7 and FAdV-10 (Barr and Scott, 1988); FAdV-11 (Mendelson et al., 1995) and FAdV-12 (Saifuddin et al., 1992). The disease has been experimentally reproduced in broiler chickens with isolates from IBH outbreaks (Fadly and Winterfield, 1973; Wells and Harrigan, 1974).

Identification of IBH as a primary disease in broilers has urged the need of vaccines to control IBH at their parent level (Ahmad and Burgess, 2001; Grimes, 1992). Control of IBH has been attempted in several countries by vaccination of broiler breeders and broiler chickens with inactivated, autogenous, (Alvarado et al., 2007; Cowen, 1992) or chick-embryo propagated vaccines (Engormix, Mexico). In Australia, IBH is controlled by vaccination of broiler breeders with a commercial live, chick embryo liver cell grown vaccine containing a FAdV-8b strain (Intervet Australia, Pvt. Ltd.). Further, this vaccine was recommended to be administered by the eye-drop method in pullets (Grimes, 1992; 2007). The Australian Intervet FAdV vaccine is for the protection of chickens against homologous type-8 FAdV invection (IBH) up to 28 days of age, by vaccinating breeders.

Most cases of acute IBH are the result of vertical transmission of FAdV, and ensuring that breeder flocks have seroconverted prior to the onset of lay can prevent the disease (Grimes, 2007). Maternal antibodies have been shown to protect the progeny against the development of IBH, as shown by challenge of progeny of broiler breeders that had been vaccinated twice with an autogenous killed vaccine (comprising serotype FAdV-8, (8565 strain) and serotype FAdV-11, (1047 strain)] (Alvarado et al., 2007). Vaccination of broiler breeders with a live, (FAdV-8, (Esurient strain)) virulent strain during rearing also has been shown to protect progeny from IBH outbreaks (Grimes, 2007). Effective protection of progeny by dual vaccination of layer breeders against IBH and CAV has been shown to protect progeny against challenge with FAdV associated with IBH (Toro et al., 2001a).

Based on hexon gene loop 1 sequencing analysis, isolates from Canadian outbreaks of inclusion body hepatitis (IBH) have been found to be genetically related to FAdV-2 strain P7-A, FAdV-x11a, FAdV-8a strain TR-59, FAdV-8a/8b strain Ontario (equal percentage identity to FAdV-8a strain T8-A and FAdV-8b strain 764), and FAdV-11 strain 1047 (Ojkic et al., 2008b).

Since 2000, IBH has been responsible for severe economic losses in the Canadian broiler industry due to sudden onset of increased mortality lasting for 5-7 days (Gomis et al., 2006; Ojkic et al., 2008b). Although high mortality and economic losses have continued for several years in the Canadian broiler industry due to IBH, no commercial vaccines are available to-date in Canada, except limited application of autogenous vaccines (Ojkic et al., 2008a).

SUMMARY OF THE DISCLOSURE

It is demonstrated herein that a significant level of homologous as well as heterologous protection of broilers against fowl adenovirus (FAdV) infection and FAdV related diseases such as Inclusion Body Hepatitis (IBH) can be obtained by vaccinating broiler parents.

An aspect of the disclosure provides a composition comprising an isolated live and/or killed fowl adenovirus (FAdV) and/or protein subunit thereof, wherein the FAdV is a strain selected from FAdV-2, FAdV-7, FAdv-8a, FAdV-8b, FAdV-8a/8b or FAdV-11 serotype strains.

In an embodiment, the subunit is a hexon and/or fiber protein.

In an embodiment, the composition comprises live virus.

A further aspect includes a vaccine comprising a composition described herein.

In an embodiment, the vaccine induces heterologous protection to one or more strains in addition to the strain and/or serotype comprised in the vaccine.

A further aspect includes a method of making a vaccine composition described herein, the FAdV strain is propagated according to the following method:
  inoculating a chicken embryonic liver cell culture with the FAdV;
  incubating the cell culture at about 30-39° C. to allow the FAdV to propagate;
  isolating the propagated FAdV; and
  formulating the propagated FAdV suitably for administration.

Yet another aspect includes a method of eliciting an immune response in a subject comprising administering a composition or vaccine described herein.

Another aspect includes a method of producing antibodies in a subject and/or its progeny specific for one or more FAdV strains, comprising administering a composition or vaccine described herein.

A method for inducing protective immunity against infection in a subject and/or its progeny by one or more FAdV strains comprising administering a composition or vaccine described herein.

Figure 12:
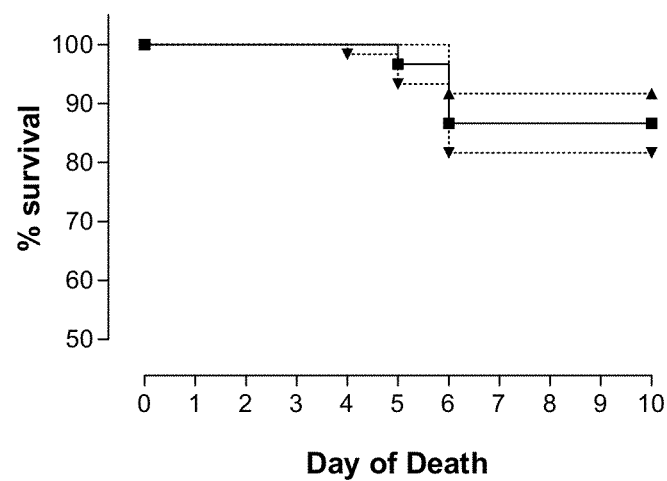

In an embodiment, the method comprises administering a live FAdV vaccine to subject, and obtaining FAdV progeny that are immunized against one or more strains of FAdV, for example one or more D and E species strains, wherein the FAdV progeny are FAdV antibody positive, optionally FAdV-2 antibody positive progeny, FAdV-7 antibody positive progeny, FAdV-8a antibody positive progeny, FAdV-8a/8b antibody positive progeny and/or FAdV-11 antibody positive progeny.

A further aspect of the disclosure includes a kit comprising a composition and/or a vaccine described herein; and an instrument for administering the composition or vaccine.

Another aspect includes a commercial package comprising a composition and/or vaccine described herein comprised in a sterile container, for example a vial.

In an embodiment, the composition, vaccine, method, kit or commercial package comprises a FAdV strain is selected from one of the isolates described herein, for example in Table 6 including for example, the 04-53357-119 isolate. In an embodiment, the strain is the 04-53357-125 isolate, 04-53357-74 isolate, and/or 06-58730 isolate.

In an embodiment, the composition, vaccine kit or package comprises a FAdV strain selected from the isolates deposited under Accession number 081210-01, 081210-02, 081210-03, and/or 081210-04.

In an embodiment, the composition, vaccine, kit, or commercial package comprises two or more strains selected from the isolates deposited under Accession number 081210-01, 081210-02, 081210-03, and/or 081210-04.

Other features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

FIG. 1 (Experiment 1): FAdV 8a/8b (or FAdV-08a strain T8-A) challenge of broiler progenies at day-14 of age.

FIG. 2 (Experiment 1): FAdV-7 (FAdVx11a like) challenge of broiler progenies at day-14 of age.

FIG. 3 (Experiment 2): [Repeat experiment.] FAdV 8a/8b (or FAdV-08a strain T8-A) challenge of broiler progenies at day-14 of age.

FIG. 4 (Experiment 2): [Repeat experiment.] FAdV-7 (FAdVx11a like) challenge of broiler progenies at day-14 of age.

FIG. 5 (Experiment 3): FAdV-11 challenge of broiler progenies at day-14 of age.

FIG. 6 (Experiment 3): FAdV-8a challenge of broiler progenies at day-14 of age.

FIG. 7: Broiler progenies from group 1, 2, 3, 4 and 9 (Table 2) of broiler breeder parents challenged with FAdV-8a/8b [homologus challenge]. Broilers were significantly protected against IBH when their parents were vaccinated with a high dose of FAdV-8a/8b adjuvanted with CpG-ODN. $p<0.05$) [HD=high dose of FAdV-8a/8b inactivated antigens; LD=Low dose of FAdV-8a/8b inactivated antigens; Em=Emulsigen as a vaccine adjuvant; CpG=CpG-ODN as a vaccine adjuvant; control=no vaccination.] n=60/group.

FIG. 8: Broiler progenies from group 5, 6, 7, 8 and 9 (Table 2) of broiler breeder parents challenged with FAdV-8a/8b [heterologus challenge]. Broilers were significantly protected against IBH when their parents were vaccinated with a high dose of FAdV-7 adjuvanted with CpG-ODN. ($p<0.05$) [HD=high dose of FAdV-7 inactivated antigens; LD=Low of FAdV-7 inactivated antigens; Em=Emulsigen as a vaccine adjuvant; CpG=CpG-ODN as a vaccine adjuvant; control=no vaccination.] n=60/group.

FIG. 9. Mortality of groups of 14-day-old commercial broiler chickens following inoculation of FAdV. FAdV-x11a-like virus (▲), FAdV-8a strain TR-59 (●), FAdV-8a strain T8-A (○), FAdV-11 strain 1047 (▼) or saline (■). Birds that were inoculated with either FAdV-8a strain TR-59 or FAdV-11 strain 1047 demonstrated 5% mortality; in contrast, birds that were inoculated with either FAdV-8a strain T8-A or FAdV-x11a-like virus demonstrated 15% mortality (n=64). All FAdV inoculated groups had significantly lower survival when compared to saline injected chickens (control).

FIG. 10. Gross, microscopic and electron microscopic lesions of IBH affected chicken. The liver is swollen; with diffuse hemorrhagic and necrotizing foci due to FAdV infection (A) the pancreas had multifocal hemorrhagic necrotizing foci (B). Dark areas (arrow) demonstrate INIB due to FAdV replication in hepatocytes, (H&E), bar=100 μm (C) and pancreatic acinar cells, (H&E), bar=100 μm (D). Electron microscopic demonstration of adenoviruses in the nucleus of an IBH infected hepatocyte, bar=2500 nm, insert bar=500 nm (E) and pancreatic acinar cell, bar=2 μm (F).

FIG. 11 Survival of 14-day-old broilers following homologous challenge of FAdV. Broilers derived from broiler breeders vaccinated with high dose (▲) or low dose (▼) of FAdV-8a strain T8-A or saline (■) following challenge with $1\times10^7$ $CCID_{50}$ FAdV-8a strain T8-A. The group of broiler chickens derived from vaccinated parents (high dose) had an increased survival although the protection was not statistically significant ($p=0.275$).

FIG. 12. Survival of 14-day-old broilers following heterologous challenge. Survival of 14-day-old broilers derived from broiler breeders vaccinated with high dose (▲) or low dose (▼) of FAdV-8a strain T8-A or saline (■) following challenge with $1 \times 10^7$ $CCID_{50}$ FAdV-8a strain T8-A. The group of broilers derived from vaccinated parents (high dose) had an increased survival although the protection was not statistically significant (p=0.275).

Figure 13:
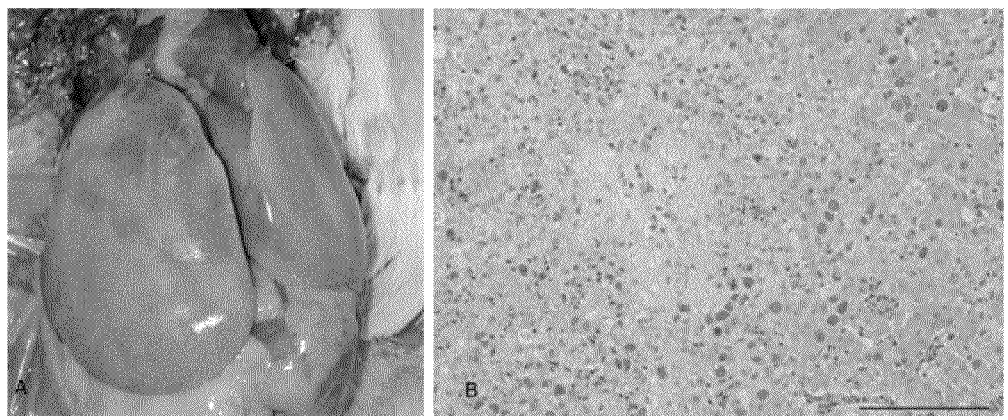

FIG. 13. Liver lesions of a broiler chicken affected with IBH. (A) Severely enlarged, pale liver of a broiler chicken that died following inoculation of FAdV-8a strain T8-A. (B) Section of the liver of an IBH affected chicken with extensive necrosis and large, homogenous, basophilic INIB containing degenerating hepatocytes. H&E. Bar=100 µm.

Figure 14:
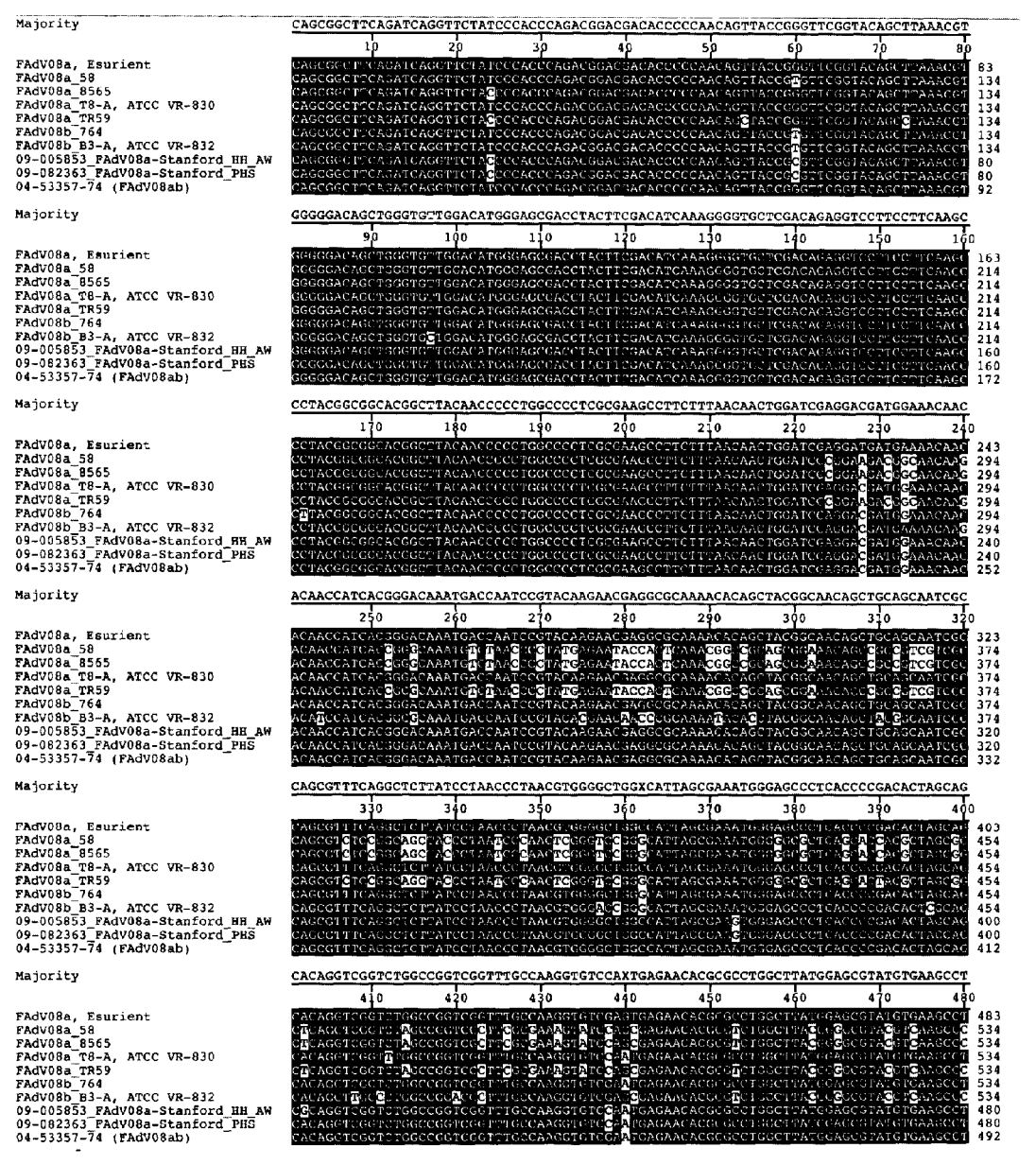
Figure 14:
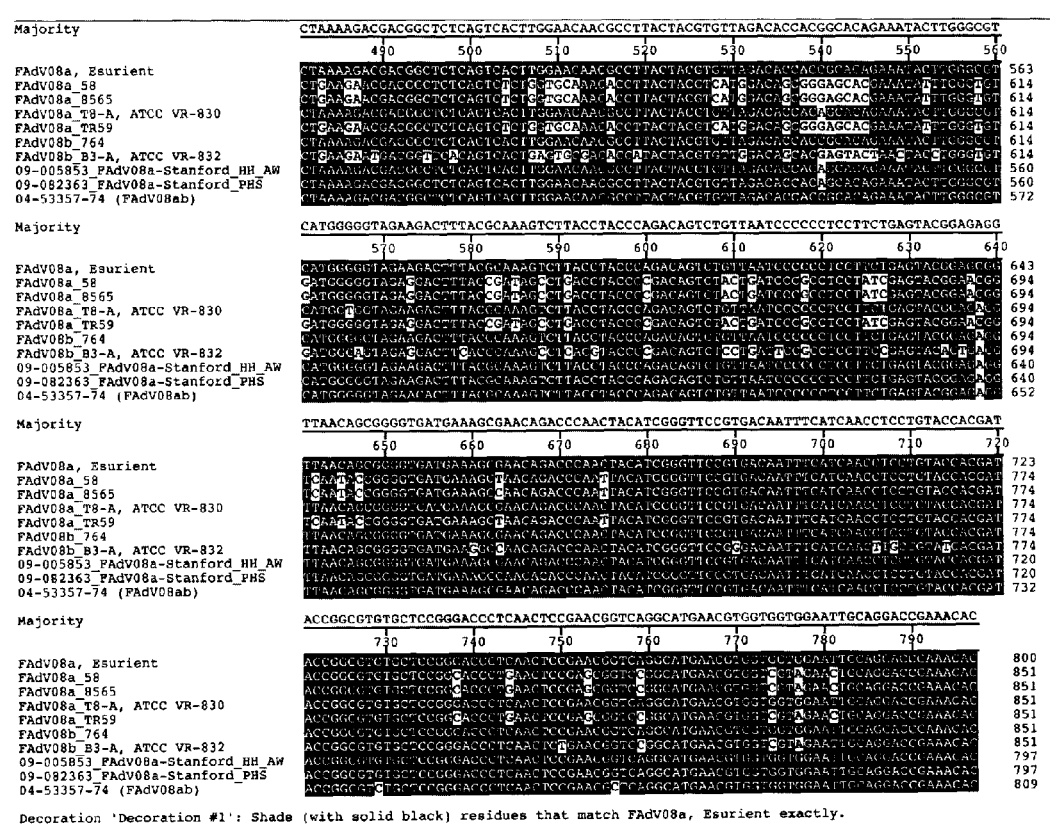

FIG. 14. Sequence alignment

Figure 15:
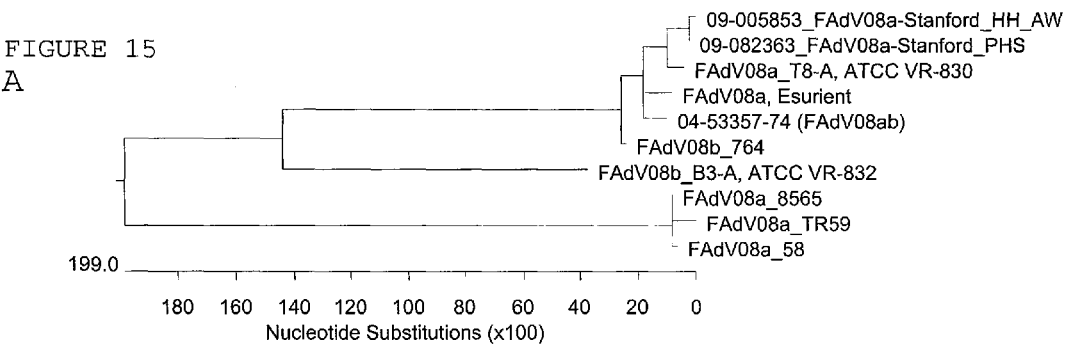

FIG. 15. A) Dendrogram
B) Percent Identity

DETAILED DESCRIPTION OF THE DISCLOSURE

I. Definitions

The term "fowl adenovirus" or "FAdV" as used herein refers to viruses of the Aviadenovirus genus of the family Adenoviridae, which are grouped into five species designated A-E based on their molecular structure and further divided into 12 serotypes based on neutralization tests with each serotype comprising several strains. Inclusion body hepatitis and another diseases and syndromes are related to FAdV infection.

The term "isolated FAdV" as used herein refers to a viral agent, which is substantially free of cellular material or culture medium when propagated.

The term "FAdV vaccine" as used herein includes a live and a killed FAdV vaccine.

The term "live FAdV" as used herein means fowl adenovirus that is infectious, including unattenuated and attenuated fowl adenovirus.

The term "live FAdV vaccine" as used herein refers to a vaccine composition comprising infectious fowl adenovirus, including unattenuated and attenuated fowl adenovirus that upon administration stimulates immunity (e.g. antibody and/or cellular immunity) against the immunizing fowl adenovirus and/or related strains.

The term "killed FAdV" as used herein refers to fowl adenovirus that is non-infections. For example, fowl adenovirus can be inactivated by b-propriolactone as described previously (Garlick and Avery, 1976).

The term "killed FAdV vaccine" or "inactivated FAdV vaccine" as used herein refers to a vaccine composition comprising non-infectious fowl adenovirus that upon administration stimulates immunity (e.g antibody and/or cellular immunity) against the immunizing fowl adenovirus and/or related strains.

The term "FAdV-8a/8b" as used herein refers to FAdV-8 strains that are characterized in having about equal percentage identity to the hexon L1 loop region of FAdV-8a and -8b reference strains, for example FAdV-8a strain T8-A and FAdV-8b strain 764. FAdV 8a/8b isolate 04-53357-74-74 for example was isolated from an IBH diseased 14-day old broiler from Saskatchewan, and has the same % identity to FAdV-8a T8-A and FAdV-8b 764.

The term "FAdV related disease or syndrome" as used herein refers to clinical presentations resulting from or related to FAdV infection including but not limited to pneumonia and tracheitis, proventriculitis, inclusion body hepatitis, quail bronchitis, hydropericardium syndrome, gizzard erosions, and pancreatic necrosis for example in chickens and guinea fowl.

The term "inclusion body hepatitis" or "IBH" as used herein in relation to chickens means a disease that is characterized by a sudden onset of increased mortality for 3-4 days, which usually returns to normal on day 5 but occasionally continues for 2-3 weeks. Mortality may reach 10% and occasionally be as high as 30%. IBH lesions are characterized by hepatic necrosis with microscopic eosinophilic or basophilic intranuclear inclusion bodies in hepatocytes. It has been shown that IBH in chickens with liver necrosis and microscopic intranuclear inclusion bodies could be reproduced by experimental inoculation with different serotypes of FAdVs (Grgic et. al. 2006, Philippe et. al. 2007). Transmission of IBH occurs both vertically and horizontally (McFerran and Adair, Avian Adenoviruses: A review. Avian Pathol 6(3) 189-217. 1977). Immunosuppression due to early infections by viruses such as infectious bursal disease virus (IBDV) or chicken anemia virus (CAV) may facilitate the horizontal transmission of IBH. IBH of chickens was first described in the USA in 1963 and has also been reported in Canada, the UK, Australia, Italy, France and Ireland. The disease has a worldwide distribution with suggestions that its incidence is increasing in many poultry producing areas.

The term "homologous protection" as used herein with regard to FAdV, refers to protection against a same FAdV strain e.g. of the same genotype, for example, administration of a composition comprising a FAdV strain, live and/or dead, provides recipients and/or their progeny, who have successfully mounted an immune response, immune protection from infection by other FAdV having the same genotype (e.g. homologous protection).

The term "heterologous protection" as used herein with regard to FAdV, refers to protection against FAdV related strains, for example administration of a composition comprising a FAdV strain, live and/or dead, provides recipients, and/or their progeny, who have successfully mounted an immune response, immune protection from infection by FAdV having the same genotype as well as by FAdV having different genotypes (e.g. heterologous protection).

The term "FAdV-2 antibody positive progeny" as used herein refers to the progeny of a maternal parent, where the parent was administered or immunized with a FAdV-2 containing composition or vaccine The term "FAdV-7 antibody positive progeny" as used herein refers to the progeny of a maternal parent, where the parent was administered or immunized with a FAdV-7 containing composition or vaccine.

The term "FAdV-8a antibody positive progeny" as used herein refers to the progeny of a maternal parent, where the parent was administered or immunized with a FAdV-8a containing composition or vaccine.

The term "FAdV-8b antibody positive progeny" as used herein refers to the progeny of a maternal parent, where the parent was administered or immunized with a FAdV-8b containing composition or vaccine.

The term "FAdV-8a/b antibody positive progeny" as used herein refers to the progeny of a maternal parent, where the parent was administered or immunized with a FAdV-8a/b containing composition or vaccine.

The term "FAdV-11 antibody positive progeny" as used herein refers to the progeny of a maternal parent, where the parent was administered or immunized with a FAdV-11 containing composition or vaccine.

The term "FAdV antibody positive progeny" as used herein refers to the progeny of a maternal parent, where the parent was administered or immunized with a FAdV containing composition or vaccine, optionally comprising two or more FAdV strains, optionally FAdV-2, FAdV-7, -8a, -8b, -8a/8b, and/or -11 strain wherein the parent mounted an antibody response and wherein maternal FAdV antibodies were passed to the progeny.

The term "non-FAdV progeny" as used herein means progeny of subjects not exposed to the compositions of the application.

The term "high dose" and "low dose" as used herein in reference to the dose of viral particles in a composition for administration to a subject refers to the relative amounts of virus in the dose to be adminstered for example inactivated virus. For example low dose includes amounts $5 \times 10^6$ PFU and less, and high dose includes amounts of more than $5 \times 10^6$ PFU for example $1 \times 10^5$ pfu is considered low dose and $1 \times 10^8$ pfu is a high dose.

The term "immunologically effective amount" of a composition or vaccine of the disclosure comprising a FAdV is a quantity sufficient to, when administered to a subject, elicit an immune response to the FAdV and/or induce protective immunity, including homologous immunity and/or heterologous immunity, in the subject and/or progeny thereof. The "immunologically effective amount" can be readily determined or readily titrated by routine testing. An effective amount is one in which a sufficient immunological response to the vaccine is attained to protect the bird and/or the progeny thereof, exposed to the virus which causes IBH or related illness. Preferably, the avian species, or for example a progeny thereof, is protected to an extent in which one to all of the adverse physiological symptoms or effects of the viral disease are found to be significantly reduced, ameliorated or totally prevented.

The term "induces protective immunity" as used herein means that administration of an effective dose of a composition or vaccine comprising for example, the FAdV-7, -8a, -8b, -8a/8b and/or -11 genotypes described herein, results in the production of antibodies that inhibit infection by one or more of FAdV-7, -8a, -8b, -8a/8b and/or -11 and/or other serotype strains, for example within the same species (e.g. D or E) and for example, result in decreased mortality in the immunized fowl and/or the progeny thereof, when subsequently challenged with a virulent FAdV-7, -8a, -8a/8b and/or -11 compared to an unimmunized fowl and/or progeny thereof. For example, a dose of a virulent FAdV-8a/8b strain which would result in about 100% mortality in unimmunized progeny, would in immunized progeny exhibit less than 70%, less than 60% less than 50%, less than 40% less than 30%, less than 20% or less than 10% mortality. Alternatively stated the composition or vaccine for example reduces mortality in immunized progeny by at least 20%, at least 30%, at least 40%, at least 50%, at least 60%, at least 70%, at least 80%, at least 90%, at least 95%, at least 99.2%, at least 99.3%, at least about 99.4% or about 99.5%.

The term "serious infection" as used herein means an infection that results in clinical disease, acute illness and/or death in a proportion of infected subjects. For example, a serious infection related to FAdV can include for example infections that result in pneumonia and tracheitis, proventriculitis, inclusion body hepatitis (IBH), quail bronchitis, hydropericardium syndrome, gizzard erosions, and pancreatic necrosis.

The term "subject" as used herein refers to any animal that is susceptible to FAdV infection, including for example avian species such as a chicken (broiler, broiler parent, broiler grand-parent, broiler great-grand parent), and pigeon The term "hybridize" refers to the sequence specific non-covalent binding interaction with a complementary nucleic acid. The hybridization is conducted under appropriate stringency conditions such as high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The definitions and embodiments described in particular sections are intended to be applicable to other embodiments herein described for which they are suitable as would be understood by a person skilled in the art.

II. Compositions and Vaccines

It is demonstrated herein that compositions and/or vaccine compositions comprising FAdV, for example FAdV-7, FAdV-8a and/or FAdV-8a/8b strains, administered to chickens, for example breeders, protected and increased survival of their progeny when challenged with for example FAdV-7, FAdV-8a, FAdV-8a/8b and/or FAdV-11 strains. Live FAdV immunization was demonstrated herein to result in dramatically enhanced protective homologous and heterologous immunity in progeny. For example, immunization of parent breeders with FAdV-8a provided heterologous protection in progeny against FAdV-7 and FAdV-11 challenge; immunization of breeders with FAdV-7 provided heterologous protection in progeny against FAdV-8a challenge. Increased survival was also seen when FAdV-7 antibody positive progeny were challenged with FAdV-11, although the increased survival was not statistically significant in the group tested. Killed FAdV vaccine comprising adjuvant also provided homologous and heterologous protection (see for example, FIGS. 7 and 8). It is also demonstrated herein that FAdV related disease, for example disease related to FAdV-8a is transmitted vertically in for example non-immunosuppressed chickens. Vaccination therefore provides protection in breeders and progeny.

The heterologous or cross protection is seen across FAdV serotypes. For example, FAdV serotypes in species D and E of FAdV nomenclature are as follows:

Fowl adenovirus D Serotypes: (FAdV-2, FAdV-3, FAdV-9, FAdV-11)

Fowl adenovirus E Serotypes: (FAdV-6, FAdV-7, FAdV-8a, FAdV-8a/8b, FAdV-8b).

As demonstrated herein, immunization with FAdV E species (e.g. FAdV-8a, FAdV-8a/8b as well as FAdV-7) provides protection against FAdV D species (e.g. FAdV-11). Accordingly, a combination vaccine composition comprising at least one FAdV from each of D and E serotypes may protect birds against multiple strains of FAdV serotypes D and E viruses, in addition to the strains in the combination vaccine.

As it is demonstrated that heterologous protection can be obtained in progeny, vaccination with more than one strain/serotype/species may provide broader serotype protection to progeny of breeders, An aspect of the disclosure includes a composition comprising an isolated fowl adenovirus (FAdV), wherein the FAdV is a strain selected from FAdV D species (e.g. FAdV-2, FAdV-3, FAdV-9, FAdV-11) and/or E (FAdV-6, FAdV-7, FAdV-8a, FAdV-8b). In an embodiment, the FAdV is a strain selected from FAdV-7, FAdv-8a, FAdV-8b, FAdV-8a/8b and/or FAdV-11 serotype strains. In an embodiment, the strain induces heterologous protection to one more FAdV serotypes and or strains. In an embodiment, the composition comprises a suitable carrier.

In an embodiment, the composition is a vaccine composition.

The International Committee on Taxonomy of Viruses (ICTV) has developed a classification based on DNA sequence data. Unless otherwise stated, reference to serotypes herein refers to the ICTV classification nomenclature.

A FAdV serotype is defined as one which shows no cross-neutralization with others, or shows a homologous: heterologous titer ratio greater than 16 in both directions (Benko et al., 2005). If the titer is between 8-16, serotypes can be differentiated by biophysical or biochemical methods (Erny et al., 1995; Hess et al., 1998). In the past, the American and European classification of FAdV have identified 12 serotypes designated as US/FAdV1-12 and EU/FAdV1-12, respectively (McFerran, 1977). The Japanese (Kawamura et al., 1964) and the Hungarian (Khanna, 1964) classifications of FAdV have designated some strains into FAdV serotypes. Classification of 12 FAdV reference strains based on real-time polymerase chain reaction (PCR) and subsequent high-resolution melting point-curve analysis of three regions of the hexon gene has been developed (Steer et al., 2009).

Classification of FAdV strains has been based on cross-neutralization (Calnek and Cowen, 1975; Grimes and King, 1977b; Kawamura et al., 1964; McFerran et al., 1972), restriction enzyme analysis (REA) followed by pair-wise comparison of restriction fragment analysis (Mendelson et al., 1995; Pallister and Sheppard, 1996), or phylogenetic analysis of the hexon protein L1 loop which has the highest variability among the FAdV serotypes and forms type-specific epitopes (Toogood et al., 1992). The fiber also has been shown to contain both type and subgroup-specific antigens (Norrby et al., 1969). The adenovirus fiber protein, for example, mediates adenovirus binding to the coxsackievirus and Ad receptor and is thus a major determinant of viral tropism. In these classifications, each serotype has a representative or type strain and several other strains with varying pathogenecity (Pallister et al., 1996). Strains of the same serotypes exhibit almost identical DNA restriction digestion patterns, whereas strains without cross reaction in neutralization tests show no common fragments (Monreal, 1992). Comparison of FAdV from different countries and continents has been difficult due to lack of agreement between serotypes, representative strains and different strains of each serotype (Benko et al., 2005; McFerran, 1997; Meulemans et al., 2004; Ojkic et al., 2008b; Steer et al., 2009). The classification of FAdV given in ICTV (Benko et al., 2005), and the American and European classifications (McFerran, 1997), with representative strains for each serotype, are summarized in Table 1.

TABLE 1

Classification of avian adenoviruses.
Serotype is in bold; species names are in italic script; strain names are in roman script.

| Fowl adenovirus species[1] | ICTV FAdV serotype/strain[2] | USA FAdV serotype/strain[3] | Europe FAdV serotype/strain[3] |
|---|---|---|---|
| *Fowl adenovirus A* | FAdV-1 CELO, 112, Phelps | FAdV-1 QBV, Indiana C, T3, QT | FAdV-1 CELO |
| *Fowl adenovirus B* | FAdV-5 340, TR-22 | FAdV-3 340-5, M2, IBH, Tipton | FAdV-5 |
| *Fowl adenovirus C* | FAdV-4 KR95, J2, KR5, J2A | FAdV-4 506-1, HR-5 | FAdV-4 KR-5 |
| | FAdV-10 CFA20, C-2B, M11 | FAdV-10 C-2B | FAdV-11 C-2B |
| *Fowl adenovirus D* | FAdV-2 P7-A, GAL-1, 685, Merlin | FAdV-2 GAL-1A, P7, Z7, SSR-48 | FAdV-2 GAL-1 |
| | FAdV-3 75, SR-49 | | |

TABLE 1-continued

Classification of avian adenoviruses.
Serotype is in bold; species names are in italic script; strain names are in roman script.

| Fowl adenovirus species[1] | ICTV FAdV serotype/strain[2] | USA FAdV serotype/strain[3] | Europe FAdV serotype/strain[3] |
|---|---|---|---|
|  | FAdV-9 A2-A, 90 | FAdV-9 (FAdV-8)[1] A2 | FAdV-10 A-2A |
|  | FAdV-11 380, 1047 | ? | FAdV-12 380 |
|  | FAdV-6 CR119, 168 | ? | FAdV-5 CR119 |
| *Fowl adenovirus E* | FAdV-7 YR36, x-11, x11a[4] | FAdV-10 x-11 | FAdV-7 x-11 |
|  | FAdV-8a TR-59, T-8, CFA40, T8-A[4] | FAdV-5 58-1, T-8, TR-59, U-6, Q-1A | FAdV-8 TR-59 |
|  | FAdV-8b Stanford[5] 764, B3 | FAdV-7 764, B3 | FAdV-9 764 |
|  | FAdV-8a/8b Ontario[6] |  |  |

[1](Zsak and Kisary, 1984);
[2](Benko et al., 2005);
[3]McFerran et al., 1977;
[4](Meulemans et al., 2001);
[5](Alvarado et al., 2007),
[6](Ojkic et al., 2008b);
? not available The teachings herein and what is known in the art would readily enable a skilled person to identify, purchase (for example from ATCC) and/or isolate, and test strains that would be useful in the compositions, vaccines, kits and methods of the disclosure. For example, a person skilled in the art, after isolating a FAdV from a chicken with IBH, would on the basis of, for example, hexon L1 loop protein gene sequence comparison and/or serotype neutralization test analysis, be able to subtype the isolate.

As an example, a Canadian FAdV isolate showing identical degrees of homology of the hexon protein L1 loop sequence by phylogenetic analysis to FAdV-8a strain T8-A and FAdV-8b strain 764, and distinguished by DNA sequence analysis (Meulemans et al., 2001) has been designated as FAdV-8a/8b Ontario strain (Ojkic et al., 2008b) which is herein incorporated by reference. FAdV-8a/8b strains e.g. with an about equal identity to FAdV-8a and FAdV-8b reference strains, have also been isolated in other provinces such as Saskatchewan.

In an embodiment, the FAdV strain is selected from FAdV-2, FAdV-7 FAdV-8a, FAdV-8a/8b and/or FAdV-11 serotype strains. In an embodiment, the strain is a FAdV-7 serotype strain. In an embodiment, the FAdV-7 sertoype strain is the 04-53357-119 isolate. In another embodiment, the strain is a FAdV-8a serotype strain. In a further embodiment, the FAdV-8a serotype strain is the 04-53357-125 isolate. In a further embodiment, the strain is a FAdV-8a/8b serotype strain. In a further embodiment, the FAdV-8a/8b serotype strain is the 04-53357-74 isolate. In another embodiment, the strain is FAdV-11 serotype strain. In another embodiment, the FAdV-11 serotype strain is the 06-58730 isolate.

FAdV, x11a-like isolate 04-53357-119 was deposited under Accession number 081210-01; FAdV8ab isolate 04-53357-74 was deposited under Accession number 081210-02; FAdV-8a, strain TR-59 isolate 04-53357-125 was deposited under Accession number 081210-03 and, FAdV11 isolate 06-58730 was deposited under Accession number 081210-04.

The isolates were deposited on Dec. 8, 2010 with the International Depository of Canada, National Microbiology Laboratory, Public Health Agency of Canada, 1015 Arlington Street in Winnipeg, Manitoba Canada R3E 3R2 under the terms of the Budapest Treaty.

In an embodiment, the composition or vaccine comprises 2, 3, 4 or 5 different FAdV selected from FAdV-2, FAdV-7, FAdV-8a, FAdV-8a/8b and/or FAdV-11.

In another embodiment, the FAdV strain is selected from a strain with at least 90%, at least 91%, at least 92%, at least 93%, at least 94%, at least 95%, at least 96%, at least 97%, at least 98%, at least 99%, at least 99.2%, at least 99.3%, at least 99.4%, at least 99.5% or more hexon L1 loop sequence identity with a FAdV-2, FAdV-7, FAdV-8a, FAdV-8a/8b and/or FAdV-11 serotype strain, e.g. for example an amino acid sequence or a nucleotide sequence. In an embodiment, the hexon L1 loop sequence is selected from SEQ ID NOs: 1-8. In an embodiment, the FAdV-7 hexon L1 loop sequence is selected from SEQ ID NO: 1 and/or 2, and/or a sequence that hybridizes with SEQ ID NO: 2 under stringent conditions. In an embodiment, the FAdV-8a hexon L1 loop sequence is selected from SEQ ID NO: 3 and/or 4 and/or a sequence that hybridizes with SEQ ID NO:4 under stringent conditions. In an embodiment, the FAdV-8a/8b hexon L1 loop sequence is selected from SEQ ID NO: 5 and/or 6 and/or a sequence that hybridizes with SEQ ID NO:6 under stringent conditions. In an embodiment, the FAdV-11 hexon L1 loop sequence is selected from SEQ ID NO: 7 and/or 8 and/or a sequence that hybridizes with SEQ ID NO: 8 under stringent conditions. In an embodiment, the stringent conditions are high stringency conditions.

In another embodiment, the FAdV strain has a DNA sequence corresponding to a FAdV-2, -7, -8a, -8a/8b and/or -11 serotype strain hexon loop sequence. In an embodiment, the strain comprises SEQ ID NO: 1, 2, 3, 4, 5, 6, 7, and/or 8. In a further embodiment, the FAdV strain has a neutralization test pattern corresponding to a FAdV 7, -8a, -8a/8b or -11 serotype strain.

In an embodiment, the FAdV serotype is FAdV-7. In an embodiment, the FAdV-7 serotype strain is x11a.

In an embodiment, the FAdV serotype is FAdV-8a. In an embodiment, the FAdV-8a serotype strain is selected from TR-59 and/or T8-A.

In a further embodiment, the FAdV serotype is FAdV-8a/8b. In a further embodiment, the FAdV-8a/8b serotype strain is a strain isolated in Saskatchewan. In yet a further embodiment, the strain is the 04-53357-74 isolate.

In another embodiment, the FAdV serotype is FAdV-11. In an embodiment, the FAdV-11 strain is selected from 380 and 1047 strains.

In another embodiment, the strain is 04-53357-119 isolate. In another embodiment, the strain is the 04-53357-125 isolate. In an embodiment, the strain is the 04-53357-74 isolate. In another embodiment, the strain is the 06-58730 isolate.

In an embodiment, the FAdV does not comprise SEQ ID NO:9. In another embodiment, the FAdV serotype strain is not the Esurient strain.

The L1 region is less than 1% of the genome but is useful for identifying strains belonging to a FAdV class. Since virulence/protective factors could be in other parts of the genome animal studies are conducted to demonstrate that a particular strain provides protection.

FAdV strains useful for preparing the compositions and vaccine compositions described herein can be isolated for example by isolating a virulent isolate for example from a bird with a clinical FAdV disease such as IBH. Isolates, for example FAdV-8a/8b isolates, are tested for example as described herein for their ability to induce immune protection.

Poultry vaccines are typically categorized either as live or inactivated vaccines; and are widely administered via musocal, parenteral and/or in ovo delivery methods to prevent or reduce several viral, bacterial and coccidial diseases (Bermudez, 2008). Inactivated vaccines do not result in vaccine-associated disease outbreaks or reversion of vaccinal Antigen (Ag) to virulence (Bermudez, 2008; Jansen et al., 2007; Schijns et al., 2008). They are used as whole killed viruses or bacterins formulated with immunoenhancing substances or adjuvants (Jansen et al., 2007).

In an embodiment, the composition comprises the whole virus. In another embodiment, the composition comprises live virus. In an embodiment, the composition comprises a FAdV subunit such as a hexon and/or fiber protein. Subunit Ag are optionally selected since they typically exist in a broader range of viruses or bacteria.

In an embodiment, the composition comprises an isolated live fowl adenovirus (FAdV), wherein the live FAdV is a strain selected from FAdV-2, FAdV-7, FAdv-8a, FAdV-8a/8b and/or FAdV-11 serotype strains.

In another embodiment, the FAdV is attenuated FAdV.

In an embodiment, the composition is immunogenic. In another embodiment, the composition comprises an immunologically effective amount of FAdV. In an embodiment, the composition comprises at least $0.01 \times 10^6$ $CCID_{50}$, at least $0.025 \times 10^6$ $CCID_{50}$, at least $0.05 \times 10^6$ $CCID_{50}$, at least $0.075 \times 10^6$ $CCID_{50}$, at least $0.1 \times 10^6$ $CCID_{50}$, at least $0.2 \times 10^6$ $CCID_{50}$, at least $0.4 \times 10^6$ $CCID_{50}$, at least $0.6 \times 10^6$ $CCID_{50}$, at least $0.8 \times 10^6$ $CCID_{50}$, at least $0.1 \times 10^6$ $CCID_{50}$, at least $1 \times 10^6$ $CCID_{50}$, at least $2 \times 10^6$ $CCID_{50}$ at least $3 \times 10^6$ $CCID_{50}$ virus per dose and/or per subject.

In an embodiment, the composition comprises at least $0.01 \times 10^6$ PFU, at least $0.025 \times 10^6$ PFU, at least $0.05 \times 10^6$ PFU, at least $0.075 \times 10^6$ PFU, at least $0.1 \times 10^6$ PFU, at least $0.2 \times 10^6$ PFU, at least $0.4 \times 10^6$ PFU, at least $0.6 \times 10^6$ PFU, at least $0.8 \times 10^6$ PFU, at least $0.1 \times 10^6$ PFU, at least $1 \times 10^6$ PFU, at least $2 \times 10^6$ PFU, or at least $3 \times 10^6$ PFU per dose and/or per subject. A person skilled in the art will be familiar with conversions between CCID and PFU e.g. $1 \times 10^5$ $CCID_{50}$ ($TCID_{50}$)/ml=$0.7 \times 10^5$ PFU/ml.

The immunologically effective amount will, as a person of skill in the art will understand, vary with the formulation, the route of administration, the host being treated and the like but can nevertheless be routinely determined by one skilled in the art.

Another aspect of the disclosure includes a vaccine a composition described herein. In an embodiment, the vaccine comprises an isolated FAdV and/or subunit thereof e.g. hexon or fibril protein, wherein the FAdV is a strain selected from FAdV-2 FAdV-7, FAdV-8a, FAdV-8b, FAdV-8a/8b and/or FAdV-11 serotype strains; and a suitable carrier.

In an embodiment, the vaccine is a subunit vaccine comprising a hexon and/or fiber protein subunit of one or more strains of FAdV. The subunit can comprise the full length protein and/or a truncated portion (e.g. truncated by 5-10 or more amino acids).

In an embodiment, the vaccine comprises an isolated live FAdV, wherein the live FAdV is a strain selected from FAdV-2, FAdV-7, FAdV-8a, FAdV-8b, FAdV-8a/8b and/or FAdV-11 serotype strains; and a suitable carrier.

The composition and/or vaccine can be comprised in a single dose formulation or in a multidose formulation.

In an embodiment, the composition and/or vaccine is comprised in a quantity sufficient to immunize at least 1, at least 10, at least 20, at least 30, at least 50, at least 75 and/or at least 100 subjects. In another embodiment, the composition and/or vaccine is comprised in a quantity sufficient to immunize at least 500, at least 1000, at least 2000, at least 3000 at least 4000, at least 5000, at least 6000, at least 7000, at least 8000, at least 9000 or at least 10,000 subjects.

In an embodiment, the composition or vaccine comprises a single FAdV strain. In another embodiment, the composition or vaccine comprises more than one FAdV strain, for example selected from the strains described herein. In an embodiment, the composition and/or vaccine comprises a strain from species E and a strain from species D. As shown herein, immunization with a strain can provide heterologous protection from challenge with other strains, for example of the same species e.g. immunization of a parent chicken with a FAdV-7 strain provides protection in progeny against challenge with FAdV-7 and/or FAdV-8a.

The composition or vaccine in an embodiment is suitably formulated as a liquid formulation, a solid formulation or a spray formulation.

In an embodiment, the composition or vaccine is suitably formulated for oral administration, for example via drinking water and/or combined with food; intranasal administration, for example via spray; eye drop; intramuscular administration; intradermal administration; subcutaneous administration; intravenous administration and/or in ovo administration. In embodiments, where the composition is administered in ovo, the composition can be administered to the breeder in ovo or to breeder progeny e.g. broiler in ovo.

Vaccine delivery systems can be particulate, and include in an embodiment, emulsions, microparticles, immunostimulatory complexes (ISCOMs) and liposomes that target associated antigens into APCs such as DCs and macrophages (Schijns et al., 2008).

In an embodiment, an immunologically effective amount of the composition or vaccine is administered to a subject in need of protection against FAdV infection or a FAdV related disease or syndrome, for example IBH.

Suitable carriers and/or pharmaceutically acceptable carriers include for example water, including sterile water, saline, ethanol, ethylene glycol, glycerol, water in oil emulsions, oil in water emulsions, saponins and alum based carriers etc and coformulants may be added. Pharmaceutically acceptable carriers include for example carriers that are suitable for animal administration, for example which have been filtered for sterility It is demonstrated herein that live vaccines are particularly effective at protecting progeny of immunized breeders e.g. FAdV antibody-positive progeny. An advantage of live vaccines is that they can be administered via drinking water, and/or at lower concentrations of virus rendering large-scale inoculations less expensive. Live virus for example elicits diverse and/or heightened immune responses in the recipient of the vaccine, including for example systemic, local, humoral and cell-mediated immune responses, generating for example antibodies that are transmissible to progeny.

The compositions and vaccines comprising live FAdV described herein are prepared by general methods known in the art and/or using embryonated eggs or embryo cell cultures for example chicken embryo liver cell cultures as described herein. The virus may be lyophilized (freeze-dried) by methods known in the art to enhance preservability for storage. After subsequent rehydration, the material is then used as a live vaccine.

Attenuated vaccines can be prepared for example by, taking the live, pathogenic virus and rendering it less virulent by methods known in the art. For instance, attenuated viruses may be prepared by serial passage through embryonated chicken eggs. Attenuated viruses can be found in nature and may have naturally-occurring gene deletions or, alternatively, the pathogenic viruses can be attenuated by making gene deletions or producing gene mutations.

In an embodiment, the composition or vaccine is for eliciting an antibody response in a subject and/or a subject progeny. In an embodiment, the composition or vaccine is for producing antibodies specific for a FAdV strain in a subject and/or its progeny. In another embodiment, the composition or vaccine is for inducing protective immunity in a subject and/or its progeny against infection by one or more FAdV strains. In an embodiment, the composition or vaccine is for providing a subject and/or its progeny with protection against a FAdV infection or a FAdV related disease or syndrome. In an embodiment, the composition or vaccine provides homologous protection in a subject and/or its progeny. In another embodiment, the composition or vaccine is a heterologous vaccine and elicits heterologous protection in a subject and/or its progeny to one or more strains in addition to the strain and/or serotype comprised in the composition or vaccine.

In an embodiment, the subject is an avian species. In another embodiment, the subject is a chicken.

In an embodiment, the composition or vaccine comprises an adjuvant. In another embodiment, the composition or vaccine comprising a killed FAdV serotype strain further comprises an adjuvant.

Adjuvants are supplementary/immunomodulatory, formulated heterogenous compounds or additives that are incorporated with Ag (eg. subunit vaccines and/or inactivated virus) to enhance the type, strength and kinetics of the host's immune system. They are broadly classified into two functional groups as signal 1 facilitators and signal 2 facilitators, however, the exact mechanism remains unidentified (Schijns, 2006). Adjuvants are for example particularly useful in compositions and vaccines comprising killed virus.

Most of the commercially available inactivated poultry vaccines are available as water-in-oil (W/O), oil-in-water (O/W), saponins and alum based formulations (Hilgers et al., 1998). The W/O formulations are assumed to form an inert depot from which the Ag is release slowly over a prolonged period and generates a sufficient Ab response (Ioannou et al., 2002b). The O/W emulsions have an oil phase of 15-25%, and are safe, and quickly release Ag from the water phase, but evoke a strong, short term immune response (Aucouturier et al., 2001). The O/W emulsified vaccines contain animal, vegetable or synthetic oils that are shown to be suitable for poultry vaccines (Stone, 1997).

Conventional inactivated vaccines are generally formulated with adjuvants such as aluminium salts (aluminium hydroxide or alum, and aluminium hydroxyphosphate) (HogenEsch, 2002), emulsions or suspensions to enhance the immunostimulatory effects. Alum, the most extensively used adjuvant in commercial vaccines, mainly skews the immune response towards a T-helper type 2 (Th2) response against protein Ag (Comoy et al., 1997).

Conventional adjuvants such as Emulsigen® (MVP Laboratories, Inc., Omaha, Nebr.) combined with dimethyl dioctadecyl ammonium bromide (DDA) also generate a Th2 type immune response accompanied with host inflammation at the site of injection due to the adjuvant (Willson et al., 1995). This preparation is commercially available as EMULSIGEN®-D, a licensed, mineral, stable O/W emulsified adjuvant that is widely used in commercial veterinary vaccines (Mutwiri et al., 2004), and is believed to create a depot at the site of injection from which the Ag is slowly released for prolonged stimulation of the immune system (Ioannou et al., 2002b; Linghua et al., 2006). DDA, a lipophilic quarternary amine adjuvant (Hilgers and Snippe, 1992), combined with other immunoenhancing compounds has been shown to augment humoral and CMI in chickens that were given experimental vaccines against IBDV (Roh et al., 2006) and ND (Rijke et al., 1998).

For example, CpG oligodeoxynucleotides (CpG-ODN) (Merial USA; Operon Technologies, Huntsville, Ala.) used in combination with killed FAdV vaccine demonstrated better immune protection in breeder progeny than FAdV virus alone and/or in combination with another adjuvant. CpG-ODN are synthetic oligodeoxynucleotides (ODNs) containing unmethylated CpG motifs. Accordingly, in an embodiment the adjuvant comprises CpG-ODN.

The adjuvant, which may be administered in conjunction with or comprised in compositions or vaccines described herein, is a substance that increases the immunological response when combined with the composition or vaccine. The adjuvant may be administered at the same time and at the same site as the composition or vaccine, or at a different time, for example, as a booster. Adjuvants also may advantageously be administered to the animal in a manner or at a site different from the manner or site in which the composition or vaccine is administered.

In an embodiment, the composition comprises an isolated fowl adenovirus (FAdV), wherein the FAdV is a strain selected from FAdV-2, FAdV-7, FAdv-8a, FAdV-8a/8b and/or FAdV-11 serotypes; and wherein the FAdV strain is propagated according to the following method:
    inoculating a chicken embryonic liver cell culture with the FAdV;
    incubating the cell culture at about 30-39° C. to allow the FAdV to propagate; and
    isolating the propagated FAdV.

A further aspect of the disclosure includes a vaccine comprising a composition wherein the isolated FAdV is propagated according to the following method:
    inoculating a chicken embryonic liver cell culture with the FAdV;
    incubating the cell culture at about 30-39° C. to allow the FAdV to propagate; and
    isolating the propagated FAdV.

The isolated propagated FAdV is optionally killed or attenuated.

In am embodiment, the embryonic liver cell culture is a primary cell culture. In another embodiment, a cell line is used to propagate the virus.

Further embodiments pertaining to the method of propagation are provided below.

III. Methods

An aspect of the disclosure includes a method of making a composition described herein. In an embodiment, the FAdV strain is propagated according to the following method:
    inoculating a chicken embryonic liver cell culture with the FAdV;
    incubating the cell culture at about 30-39° C. to allow the FAdV to propagate; and
    isolating the propagated FAdV.

A further aspect of the disclosure includes a method of making a live FAdV vaccine comprising:
    inoculating a chicken embryonic liver cell culture with the FAdV;
    incubating the cell culture at about 30-39° C. to allow the FAdV to propagate;
    isolating the propagated FAdV; and
    formulating the propagated suitably for administration.

In an embodiment, the cell culture is a SPF chick embryo liver cell culture (CEL). In another embodiment, a cell line is used to propagate the virus. In an embodiment, the cell line is a hepatoma cell line. In an embodiment, the cell line is Leghorn male hepatoma (LMH) cell line obtainable for example from American Type Culture Collection (ATCC#CRL-2117, VA).

The isolated propagated FAdV is optionally killed or attenuated.

In an embodiment, the FAdV inoculated is a strain selected from FAdV-2, FAdV-7, FAdv-8a, FAdV-8a/8b and/or FAdV-11 serotypes.

In an embodiment, the composition or vaccine comprises a FAdV liver homogenate. In an embodiment, the liver homogenate is suspended in medium, subjected to one or more freeze thaw cycles. In an embodiment, the liver homogenate suspension is centrifuged and the supernatant filtered.

Vertical transmission or reactivation of latent virus has been identified as an important mode of transmission of FAdV (Adair and Fitzgerald, 2008; Symth and McNulty, 2008). It is also possible that virulent FAdV are transmitted vertically from immunologically naïve hens infected during laying (Grimes, 1992) or prior to laying (Monreal, 1992; Ojkic and Nagy, 2003). In broiler breeders, seroconversion and development of neutralizing antibody (Ab) prior to commencement of laying is achieved through vaccination (Cserep, 2008; Guittet et al., 1997), and can prevent the vertical transmission of FAdV and subsequent IBH in the progeny (Nagy, 2007).

A further aspect of the disclosure includes a method of eliciting an immune response in a subject, comprising administering a composition or vaccine described herein to the subject.

Another aspect of the disclosure includes a method of producing antibodies in a subject and/or its progeny specific for one or more FAdV strains, for example of the same or different serotypes and/or strains, comprising administering a composition or vaccine described herein to the subject (e.g breeder).

An aspect includes a method of obtaining a FAdV antibody positive progeny comprising administering an immunologically effective amount of a composition or vaccine described herein comprising a FAdV strain to a subject; obtaining a progeny of the subject, wherein the progeny is FAdV antibody positive to the FAdV strain administered and optionally to one or more additional FAdV strains.

Whether a progeny is antibody positive can be determined for example by standard methods known in the art, including for example by testing for the presence of neutralizing antibodies. Antibody positivity results, for example, in increased resistance to FAdV related diseases or syndromes such as IBH.

A further aspect provides a method for inducing protective immunity in a subject and/or its progeny against infection, including serious infection related to one or more FAdV strains comprising administering a composition or vaccine described herein to the subject. In a further aspect, the disclosure provides a method of providing a subject with immune protection against a FAdV infection and/or a FAdV related disease or syndrome comprising administering an immunologically effective amount of a composition or vaccine described herein to the subject.

Another aspect of the disclosure includes a method of inducing protective immunity in a subject and/or its progeny comprising administering an immunologically effective amount of a composition or vaccine described herein.

A further aspect includes a method of inducing protective immunity against one or more strains of FAdV in a progeny of a subject comprising administering an immunologically effective amount of a FAdV, preferably comprised in a composition or vaccine described herein, to the subject, allowing the subject to produce progeny, wherein progeny comprise antibodies that are transmitted from the subject and which provide protective immunity to the one or more strains of FAdV.

In an embodiment the composition or vaccine administered comprises live FAdV.

A further aspect of the disclosure is a method of inducing protective immunity a subject and/or its progeny against FAdV-7, FAdV-8a, FAdV-8a/8b and/or FAdV-11 infection including serious infection comprising administering an immunologically effective amount of a composition or vaccine comprising an isolated FAdV-2, FAdV-7, FAdV-8a, FAdV-8a/8b and/or FAdV-11 serotype strain, for example a strain described herein to the subject.

Another aspect includes a method of inducing protective immunity in a subject and/or its progeny against FAdV-2, FAdV-7, FAdV-8a, FAdV-8a/8b and/or FAdV-11 serious infection comprising administering an immunologically effective amount of a composition or vaccine comprising an isolated FAdV-8a and/or FAdV-8a/8b strain, for example a strain described herein to the subject.

Another aspect provides a method of inducing immunity against a FAdV induced disease in a subject and/or its progeny, comprising administering to the subject a composition or vaccine described herein. In an embodiment, the method further comprises obtaining progeny from the subject.

Yet a further aspect provides a method of inhibiting vertical transmission of IBH comprising administering a composition or vaccine described herein to a subject, thereby inhibiting the vertical transmission of IBH to a progeny of the subject.

Yet a further aspect provides a method of inhibiting vertical transmission of FAdV comprising administering a composition or vaccine described herein to a subject, thereby inhibiting the vertical transmission of FAdV to a progeny of the subject.

Another aspect includes a method of providing passive immunity to a progeny of a subject comprising administering a composition or vaccine described herein to the subject, wherein antibodies are generated and transmitted to the progeny during reproduction.

Also provided is use of a composition or vaccine described herein for eliciting an immune response in a subject.

Another aspect of the disclosure includes use of a composition or vaccine described herein for producing antibodies in a subject and/or its progeny specific for one or more FAdV strains.

A further aspect use of a composition or vaccine described herein for inducing protective immunity against infection in a subject and/or its progeny by one or more FAdV strains. In a further aspect, the disclosure provides use an immunologically effective amount of a composition or vaccine described herein for providing a subject with immune protection against a FAdV infection or a FAdV related disease or syndrome.

Another aspect of the disclosure includes use of an immunologically effective amount of a composition or vaccine described herein for inducing protective immunity in a subject and/or its progeny.

A further aspect of the disclosure is use of an immunologically effective amount of a composition or vaccine comprising an isolated live FAdV-2, FAdV-7, FAdV-8a and/or FAdV-8a/8b serotype strain, for example a strain described herein for inducing protective immunity a subject and/or its progeny against one or more of D and E species strains, and/or one or more of FAdV-7, FAdV-8a, and/or FAdV-8a/8b.

Another aspect includes use of an immunologically effective amount of a composition or vaccine comprising an isolated live FAdV-8a and/or FAdV-8a/8b strain, for example a strain described herein for inducing protective immunity in a subject and/or its progeny against FAdV-7, FAdV-8a, FAdV-8a/8b and/or FAdV-11.

A further aspect includes use of a composition or vaccine described herein for inducing immunity against a FAdV induced disease in a subject and/or its progeny.

In an embodiment, the use is for inducing passive immunity.

In an embodiment, the method comprises administering an immunologically effective amount of a composition or vaccine comprising a live isolated FAdV-2, FAdV-7, FAdV-8a, FAdV-8a/8b and/or FAdV-11 serotype strain and a suitable carrier. In an embodiment, the immune protection induced reduces mortality in challenged FAdV progeny by at least 20%, at least 30%, at least 40%, at least 50%, at least 60%, at least 70%, at least 80%, at least 90%, at least 95% or about 99% compared to challenged non-FAdV progeny. For example, challenged FAdV progeny refers to FAdV progeny (e.g. FAdV antibody positive progeny) exposed to or challenged by a FAdV, for example to a FAdV that is the serotype, a serotype that is cross protected and/or a strain administered to the maternal parent and challenged non-FAdV progeny refers to birds exposed to or challenged by a FAdV, for example, a FAdV strain, serotype or cross protected serotype that the maternal parent was not immunized against.

In an embodiment, the FAdV related disease or syndrome is one or more of pneumonia and tracheitis, proventriculitis, inclusion body hepatitis (IBH), quail bronchitis, hydropericardium syndrome, gizzard erosions, and pancreatic necrosis for example in chickens and guinea fowl. In addition, FAdV have also been associated with poor production and respiratory problems. In an embodiment, the FAdV related disease or syndrome is IBH.

A further method provided by the disclosure is a method for inducing immunity against a FAdV induced disease in a subject and/or its progeny, comprising administering to the subject a composition or vaccine described herein.

In an embodiment, the method comprises administering a composition comprising an immunologically effective amount of FAdV. In an embodiment, the composition comprises at least $0.1 \times 10^6$ CCID$_{50}$, at least $0.2 \times 10^6$ CCID$_{50}$, at least $0.4 \times 10^6$ CCID$_{50}$, at least $0.6 \times 10^6$ CCID$_{50}$, at least $0.8 \times 10^6$ CCID$_{50}$, at least $0.1 \times 10^6$ CCID$_{50}$, at least $1 \times 10^6$ CCID$_{50}$, at least $2 \times 10^6$ CCID$_{50}$, or at least $3 \times 10^6$ CCID$_{50}$ per dose.

In an embodiment, the method comprises administering the composition or vaccine orally, for example via drinking water and/or combined with food; intranasally, for example via spray; via eye drop; intramuscularly; intradermally; subcutaneously; intravenously and/or by in ovo administration. In embodiments, where the composition is administered in ovo, the composition can be administered to the breeder in ovo or to breeder progeny e.g. broiler in ovo. A person skilled in the art would be familiar with methods for administering the composition or vaccine in ovo.

In an embodiment, the composition or vaccine administered comprises a particulate solution, an emulsion, microparticles, immunostimulatory complexes (ISCOMs) or liposomes.

In an embodiment, the composition or vaccine is administered to the subject any time prior to the subject reaching egg laying maturity. In an embodiment, the composition or vaccine is administered to the subject when the subject is in ovo.

In another embodiment the composition or vaccine is administered when the subject is about 3 weeks to about 22 weeks old. In an embodiment, the subject is at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, or at least 22 weeks old.

In an embodiment, the method further comprises a subsequent administration of a composition or vaccine comprising a FAdV strain, for example as a booster. The subsequent administration can for example comprise live virus and/or killed virus. The composition or vaccine may be the same or different than the first administration, for example the subsequent administration may comprise a lower number of viral particles. One or more subsequent doses are optionally administered.

In an embodiment, the method comprises administering a live FAdV vaccine to a subject, and obtaining FAdV progeny that are immunized against one or more strains of FAdV. In an embodiment the FAdV progeny are FAdV-7 antibody positive progeny. In an embodiment, the progeny are FAdV-8a antibody positive progeny. In an embodiment, the progeny are FAdV-8a/8b antibody positive progeny. In another embodiment, the progeny are FAdV-11 antibody positive progeny. In an embodiment, the progeny comprise FAdV antibody positive progeny, comprising antibodies to one or more strains of FAdV.

Another aspect of the disclosure includes a method of inhibiting an IBH outbreak in a group of subjects and/or their progeny comprising administering to members of a group of subjects a composition or vaccine described herein. In an embodiment, the members who are administered the composition or vaccine comprise at least 10%, at least 20%, at least 30%, at least 40%, at least 50%, at least 60%, at least 70%, at least 80%, at least 90% or more of the members of the group.

Successful immunization can be determined using a number of methods known in the art. For example, a person skilled in the art could test the immunized subject for the presence of virus neutralizing antibodies against FAdV.

In an embodiment, the subject is a breeder. In another embodiment, the progeny is a broiler progeny.

III. Kits and Commercial Package

A further aspect includes a kit comprising a composition or a vaccine described herein and an instrument for administering the composition or vaccine. In an embodiment, the instrument comprises an eye dropper or a syringe. In another embodiment, the kit comprises a lyophilized vaccine vial and a diluent vial.

A further aspect comprises a commercial package comprising a composition or vaccine described herein comprised in a sterile container, for example a vial. In another embodiment, the commercial package comprises frozen vaccine anand/or lyophilized vaccine.

In an embodiment, the kit and/or commercial package comprises a multidose vaccine. In an embodiment, the multidose vaccine comprises sufficient quantity for example for at least 100, at least 500, at least 1000, at least 2000, at least 3000, at least 4000, at least 5000, at least 6000, at least 7000, at least 8000, at least 9000 or at least 10000 vaccinations e.g. doses. In another embodiment, the multidose vaccine comprises a first dose and a booster, each for example in sufficient quantity for example for at least 100, at least 500, at least 1000, at least 2000, at least 3000, at least 4000, at least 5000, at least 6000, at least 7000, at least 8000, at least 9000 or at least 10000 vaccinations e.g. doses.

Multidose refers to the number of vaccine doses. Accordingly, in an embodiment, the multidose vaccine refers to doses for the primary, or secondary vaccination. In an embodiment, the multidose vaccine comprises live or killed products. In an embodiment, the multidose vaccine comprises two products, wherein each can be multidose, for example primary live and secondary killed.

In an embodiment, the kit and/or commercial package comprises a package insert that describes how to administer the composition or vaccine.

In a further embodiment, the kit and/or commercial package comprises a diluent, for example a sterile, buffered aqueous solution that is stable at room temperature.

The following non-limiting examples are illustrative of the present disclosure:

EXAMPLES

Example 1

Live Vaccine
Summary

The objective of this study was to investigate the effect of two live adenoviral vaccines containing either FAdV-8a/8b (or FAdV08a strain T8-A) strain or FAdV-7 (or FAdVx11a-like virus) strain in broiler breeders against Inclusion Body Hepatitis (IBH) in their progeny. At 16 week-of-age, two groups of broiler breeders were vaccinated orally with either FAdV-8a strain T8-A, ($1\times10^6$ 50% cell culture infectious dose $CCID_{50}$) or FAdV-7 strain x11a, ($1\times10^6$ $CCID_{50}$). Control group received 0.2 ml saline. When broiler progenies were 14-day-old, groups were challenged with FAdV-8a/8b, FAdV-7, FAdV-11 or FAdV-8a. Broiler progenies derived from the group of broiler breeders vaccinated with FAdV-8a/8b (or FAdV08a strain T8-A) were protected against FAdV-8a/8b, FAdV-7, FAdV-11 or FAdV-8a at a significant level ($p<0.0001$). Broiler progenies derived from the group of broiler breeders vaccinated with FAdV-7x11a-like were protected against FAdV-7, FAdV-8a/8b and FAdV-8a at a significant level ($p<0.0001$). This study demonstrated protection of broilers against IBH by vaccinating their parents with a single adenovirus vaccine containing either FAdV-8a strain T8-A, or FAdV-7 strain x11a-like virus at a statistically significant level.

Objective

The objective of this study was to investigate the effect of two live adenoviral vaccines containing either FAdV-8a/8b (or FAdV08a strain T8-A) strain or FAdV-7 (or FAdVx11a-like virus) strain in broiler breeders against Inclusion Body Hepatitis (IBH) in their progeny.

Materials and Methods
Management of Broiler Breeders

All procedures involving with animals were approved by the University of Saskatchewan Animal Care Committee. Thirty-nine, 15 week-old commercial broiler breeders (30 females and 9 males) were obtained from a local commercial broiler breeder producer, identified individually by wing-tag, (Ketchum's Clicher Tamperproof Wing Tag, Ketchun Manufacturing, Surrey, UK) and housed in the Animal Care Unit, Western College of Veterinary Medicine, University of Saskatchewan. They were randomly divided into three groups and were placed in three individual rooms; each with 10 females and three males. A lighting program and feeding were implemented according to guidelines for Ross Broiler Breeders (Aviagen™ Inc., AL). They were vaccinated against Marek's disease, Infectious bronchitis, Infectious bursal disease, Reoviral infection, Chicken anemia virus, Newcastle disease, according to the standard broiler breeder vaccination program practiced in Saskatchewan.

FAdV Vaccination of Broiler Breeders

Two FAdVs isolates; FAdV-8a strain T8-A and FAdV-7x 11a (sequenced at Animal Health Laboratory, University of Guelph) (SEQ ID NO: 5 and 6 (04-53357-74 isolate) and SEQ ID NOs: 1 and 2 (FAdV-7x11a 04-53357-119 isolate), obtained from field outbreaks of IBH in Saskatchewan were used in this study. At 16 week-of-age, two groups of broiler breeders were vaccinated orally with either FAdV-8a strain T8-A, ($1\times10^6$ $CCID_{50}$) or FAdV-7 strain x11a, ($1\times10^6$ $CCID_{50}$). Control group received 0.2 ml saline.

IBH Challenge of the Progeny

When broiler breeders were 37-week of age or more, eggs from each group were hatched, and thirty broiler chickens derived from each group were identified individually by neck tag (Swiftack Poultry Tags, Heartland Animal Health Inc., MO) and reared in an isolation facility. Water and feed were provided ad libitum. Air in the room was exhausted through a high efficiency particulate air (HEPA) filter and replaced with non-recirculated intake air at a rate of 18/changes/hr. Air pressure differentials and strict sanitation were maintained in this facility. Photoperiods of 24 h per day for the first 3 days and 16 h per day for the remaining 21 days were established. Room temperatures were maintained at 30-32° C. for the first three days and 28-30° C. for the remaining duration of the experiment.

Virus Isolation

FAdVs were propagated in 14-day-old SPF chick embryo liver cell culture (CEL) for animal challenge studies (Animal Health Laboratory, Guelph).

Experiment 1:

When broiler breeders were 37 week-of-age, eggs were removed and hatched and groups of broiler progenies (n=30) at day-14 of age were challenged with FAdV-8a strain T8-A ($1\times10^7$ $CCID_{50}$) or FAdV-7 strain x11a ($1\times10^7$ $CCID_{50}$) to demonstrate homologous or heterologous protection.

Experiment 2:

When broiler breeders were 39 week-of-age, groups of broiler (n=30) progenies at day-14 of age were challenged with FAdV-8a strain T8-A ($1\times10^7$ $CCID_{50}$) or FAdV-7 strain x11a ($1\times10^7$ $CCID_{50}$) [repeat experiment]. Other groups of broilers were challenged with FAdV-11 ($1\times10^7$ $CCID_{50}$).

Experiment 3:

When broiler breeders were 41 week-of-age, groups of broiler (n=30) progenies at day-14 of age were challenged with FAdV-11 ($1\times10^7$ $CCID_{50}$) [repeat experiment] or FAdV-8a ($1\times10^7$ $CCID_{50}$).

Results

FIG. 1 demonstrates results of Experiment 1 where broiler progenies were challenged with FAdV 8a/8b (or FAdV-08a strain T8-A) at day 14 of age. Broiler progenies were derived from their broiler breeder parents vaccinated with a single vaccination of live FAdV-8a/8b, FAdV-7 or saline (control) by the oral route at the age of 16 weeks. FAdV-8a/8b or FAdV-7 progenies were significantly protected against FAdV-8a/8b challenge ($p<0.0001$).

Figure 2:
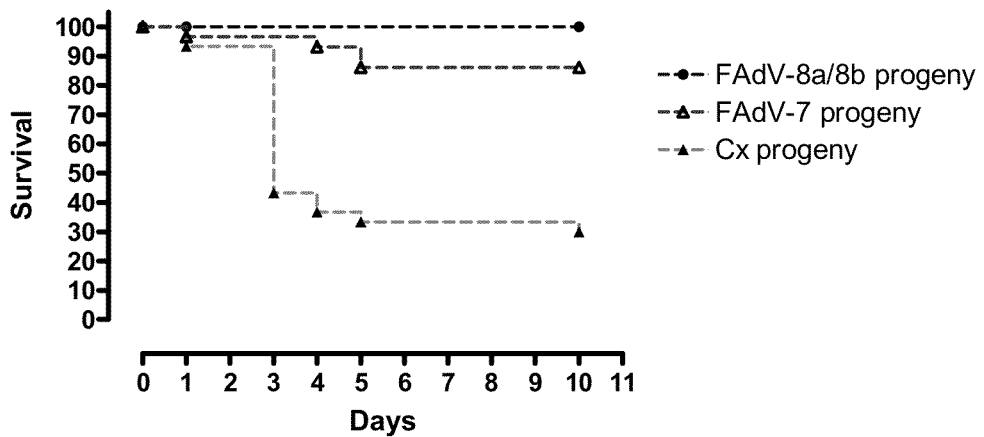

FIG. 2 demonstrates results of Experiment 1 where broiler progenies were challenged with FAdV-7(FAdVx11a like) at day 14 of age. Broiler progenies were derived from their broiler breeder parents vaccinated with a single vaccination of live FAdV-8a/8b, FAdV-7 or saline (control) by the oral route at the age of 16 weeks. FAdV-8a/8b or FAdV-7 progenies were significantly protected against FAdV-7 challenge ($p<0.0001$).

Figure 3:
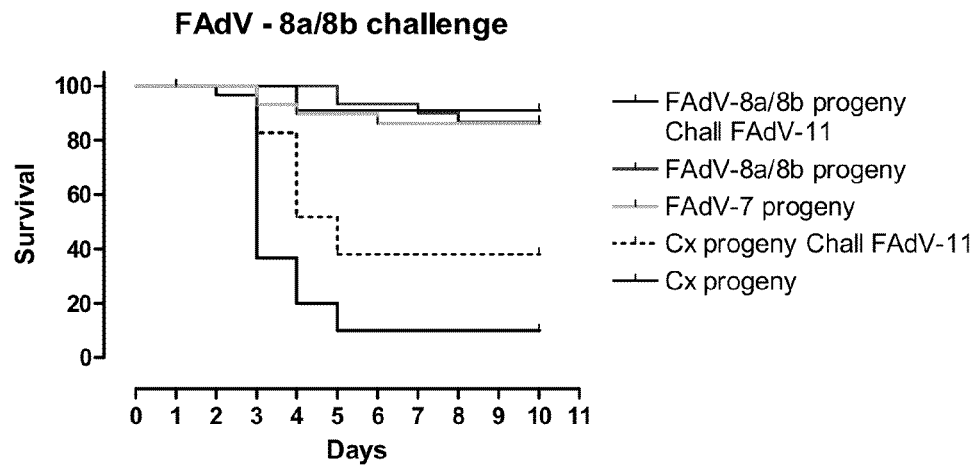

FIG. 3 demonstrates results of Experiment 2 where broiler progenies were challenged with FAdV 8a/8b (or FAdV-08a strain T8-A) at day 14 of age. Broiler progenies were derived from their broiler breeder parents vaccinated with a single vaccination of live FAdV-8a/8b, FAdV-7 or saline (control) by the oral route at the age of 16 weeks. FAdV-8a/8b or FAdV-7 progenies were significantly protected against FAdV-8a/8b challenge (p<0.0001). Furthermore, FAdV-8a/8b antibody positive progeny were significantly protected by FAdV-11 challenge (p<0.0001).

Figure 4:
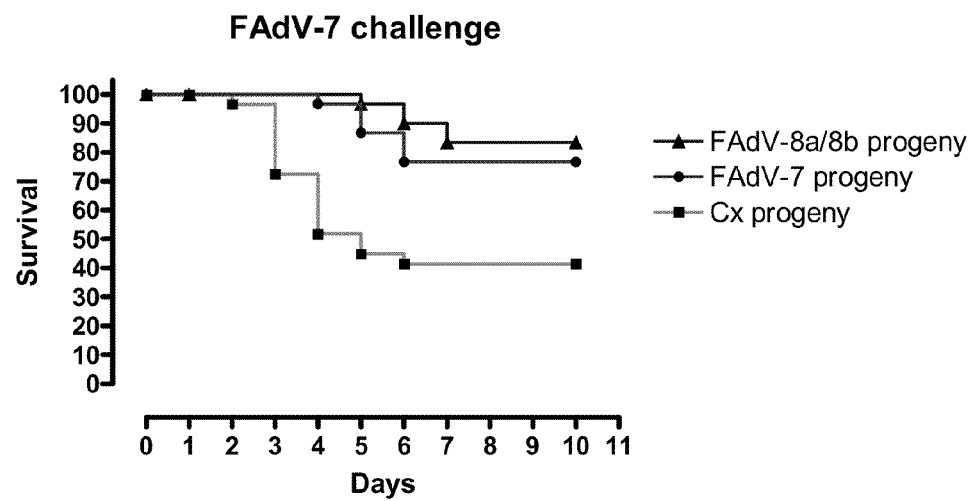

FIG. 4 demonstrates results of Experiment 2 where broiler progenies were challenged with FAdV-7 (FAdVx11a like) at 14 days of age. Broiler progenies were derived from their broiler breeder parents vaccinated with a single vaccination of live FAdV-8a/8b, FAdV-7 or saline (control) by the oral route at the age of 16 weeks. FAdV-8a/8b or FAdV-7 progenies were significantly protected against FAdV-7 challenge (p<0.0001).

Figure 5:
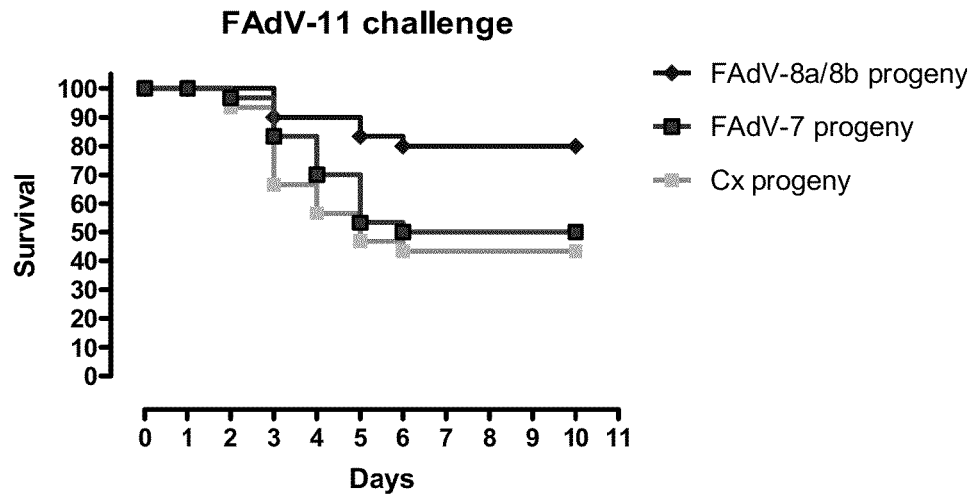

FIG. 5 demonstrates results of Experiment 3 where broiler progenies were challenged with FAdV-11 at 14 days of age. Broiler progenies were derived from their broiler breeder parents vaccinated with a single vaccination of live FAdV-8a/8b, FAdV-7 or saline (control) by the oral route at the age of 16 weeks. FAdV-8a/8b antibody positive progeny were significantly protected against FAdV-11 challenge (p<0.0001).

Figure 6:
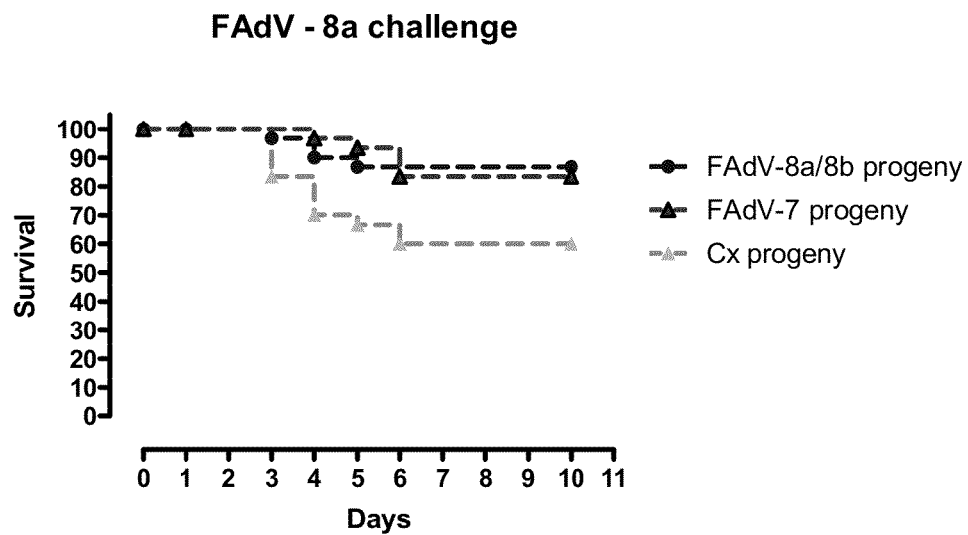

FIG. 6 demonstrates results of Experiment 3 where broiler progenies were challenged with FAdV-8a at 14 days of age. Broiler progenies were derived from their broiler breeder parents vaccinated with a single vaccination of live FAdV-8a/8b, FAdV-7 or saline (control) by the oral route at the age of 16 weeks. FAdV-8a/8b or FAdV-7 progenies were significantly protected against FAdV-8a challenge (p<0.0001).

Termination of the experiments were at day-10 post challenge, survivors did not have any clinical signs or pathological lesions at necropsy.

Example 2

Killed Vaccine

Material and Methods

Inactivated Adenovirus Vaccination in Broiler Breeder Parents and Challenge Protection in their Progeny.

The objective of this experiment was to demonstrate protection of broilers against IBH by vaccinating their parents with an inactivated adenovirus vaccine. Ten-week old broiler breeders were obtained from a local broiler breeder producer in Saskatchewan and maintained them at Animal Care at Western College of Veterinary Medicine. Nine groups of broiler breeders, each group containing five females and one male were vaccinated at 12 and 15 weeks with inactivated $1 \times 10^5$ pfu (low dose) or $1 \times 10^8$ pfu (high dose) of FAdV-8a/8b or FAdV-7 formulated with Emulsigen or oligonucleotide containing CpG-ODN as an adjuvant (Table 2) (CpG-ODN T CGTCGTTGTCGTTTTGTCGTT (SEQ ID NO:22) Emulsigen®] (Ralston, Nebr.). Progenies of these broiler breeders were challenged at day-14. Briefly, groups containing 60 broilers were intramuscularly inoculated with $1 \times 10^7$ pfu of FAdV-8a/8b. Clinical signs were recorded for 10 days following challenge.

TABLE 2

Inactivated adenovirus vaccination in broiler breeders at 12 and 15 week of age.

| Groups | Broiler breeders (n = 6) | Experimental challenge (progeny; n = 60) |
|---|---|---|
| 1 | FAdV-8a/8b-1 × $10^5$ pfu's with 20% Emulsigen-D | FAdV-8a/8b |
| 2 | FAdV-8a/8b-1 × $10^8$ pfu's with 20% Emulsigen-D | FAdV-8a/8b |
| 3 | FAdV-8a/8b-1 × $10^5$ pfu's with 50 µg CpG-ODN | FAdV-8a/8b |
| 4 | FAdV-8a/8b-1 × $10^8$ pfu's with 50 µg CpG-ODN | FAdV-8a/8b |
| 5 | FAdV-7-1 × $10^5$ pfu's with 20% Emulsigen-D | FAdV-8a/8b |
| 6 | FAdV-7-1 × $10^8$ pfu's with 20% Emulsigen-D | FAdV-8a/8b |
| 7 | FAdV-7-1 × $10^5$ pfu's with 50 µg of CpG-ODN | FAdV-8a/8b |
| 8 | FAdV-7-1 × $10^8$ pfu's with 50 µg of CpG-ODN | FAdV-8a/8b |
| 9 | Control | FAdV-8a/8b |

Strain isolates used in experiments are listed in Table 6 of sequences below.

Results:

Inactivated Adenovirus Vaccination in Broiler Breeder Parents and Challenge Protection in their Progeny.

Figure 7:
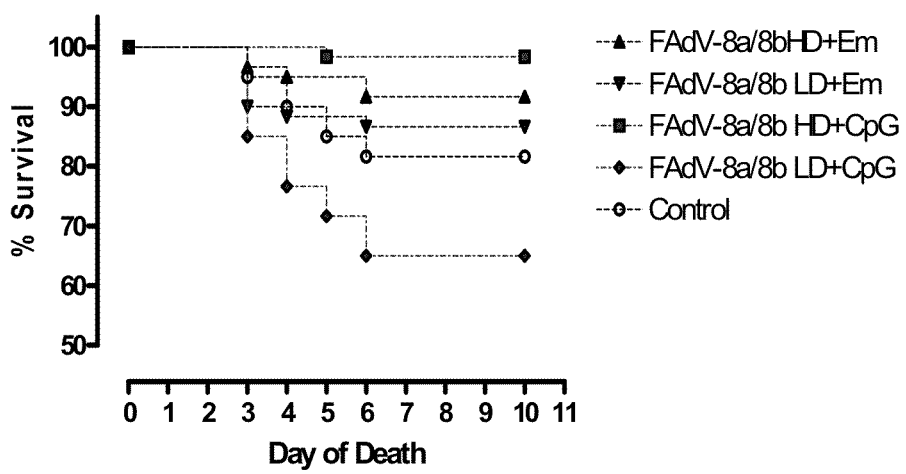

There was a significant protection of broilers against IBH in broiler breeder parents vaccinated with a high dose of inactivated antigens of FAdV-8a/8b adjuvanted with CpG-ODN (p<0.05) [homologus challenge protection] (FIG. 7).

Figure 8:
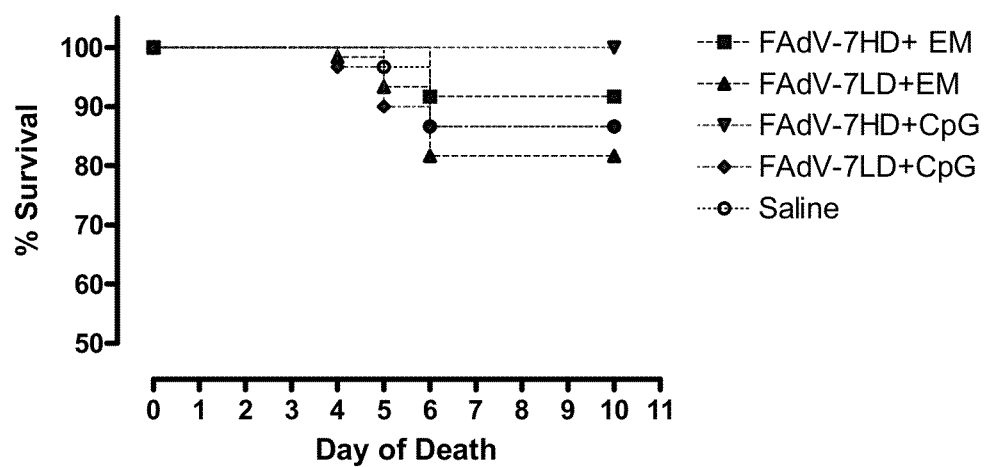

Furthermore, there is a significant protection of broilers against IBH in broiler breeder parents vaccinated with a high dose of inactivated antigens of FAdV-7 adjuvanted with CpG-ODN (p<0.05) [heterologus challenge protection] (FIG. 8).

Discussion

Historically, IBH was mostly considered a secondary disease in broilers associated with immunosuppression following infection with IBDV or CAV. Under these circumstances it was likely that immunosuppressed birds exposed to FAdV from the environment would eventually develop a clinical disease. IBH has also been occasionally described as a primary disease causing economic losses in the broiler industry without prior immunosuppression. Under these circumstances it was suggested that vertical transmission of FAdV from broiler breeders caused the clinical disease of IBH in their progeny.

It was demonstrated that a significant level of protection of broilers against IBH can be provided by vaccinating broiler breeder parents with FAdV-8a/8b or FAdV-7.

Example 3

Inclusion Body Hepatitis Animal Model Development in 14-day-old Broiler Chickens All procedures with animals were conducted according to protocols that were approved by the Animal Care Committee, University of Saskatchewan in accordance with Canadian Council on Animal Care (Olfert et al., 1993). Two hundred and sixty four day-old broiler chickens were obtained from a local hatchery in Saskatchewan, identified individually by neck tags (Swiftack Poultry Tags, Heartland Animal Health Inc., MO), randomly divided into groups and located in the Animal Care Unit, Western College of Veterinary Medicine, University of Saskatchewan, Canada. Water and commercial broiler rations were provided ad libitum and placed on kiln-dried wood shaving bedding. Air from each room was exhausted through a HEPA filter and replaced with non-recirculated intake air at a rate of 18 changes/h. Air pressure differentials and strict sanitation were maintained in this isolation facility. Photoperiods of 24 h per day for the first 3 days and 16 h per day for the remaining 23 days were established. Room temperature was maintained at 30-32° C. for the first week and 28-30° C. for the remaining duration of the animal experiment.

Birds were observed for clinical signs thrice daily for 12 days following FAdV challenge. Daily clinical scores for individual birds were recorded as follows: 0=normal; 1=hesitate to move and tire quickly; 2=unable to stand or forage for food and euthanized; 3=dead. Mortality was counted each day. Dead or euthanized birds were necropsied immediately. Parent flocks of these broiler chickens were vaccinated against IBD at 2 weeks (Clonevac D-78: Intervet Canada Ltd., Ontario, Canada), 8 weeks (Bursa BlenM; Merial Canada Ltd., Quebec, Canada), and 18 weeks (Breedervac IV Plus, Intervet Canada Ltd., Ontario, Canada) and against CAV at 18 weeks (CAV-Vac; Intervet Canada Ltd., Ontario, Canada).

Fourteen-day-old broiler chickens were randomly allocated into 33 groups (Table 4) each containing 8 birds. Groups of chickens were inoculated intramuscularly with $1 \times 10^4$, $1 \times 10^5$, $1 \times 10^6$, or $1 \times 10^7$ $CCID_{50}$ of FAdV in the left thigh as follows: (a) chicken embryo liver (CEL) grown FAdV-x11a-like virus, FAdV-8a strain TR-59, FAdV-8a strain T8-A or FAdV-11 strain 1047; (b) purified liver homogenate (LH) of FAdV from clinical cases of IBH, FAdV-x11a-like virus, FAdV-8a strain TR-59, FAdV-8a strain T8-A or FAdV-11 strain 1047; (c) saline (pH 7.4). Following FAdV or saline inoculation, chickens were comingled to maintain the same environmental and management practices and observed for 12 days for clinical signs and mortality. At 13 day post-challenge, the remaining birds were euthanized and necropsied.

Histology and Transmission Electron Microscopy

Tissue sections from the liver, pancreas and lymphoid organs were fixed in 10% neutral buffered formalin, embedded in paraffin, sectioned at 5 μm thicknesses and stained with H&E for histopathological studies. Tissue sections from the liver and pancreas were fixed in 5% glutaldehyde in sodium cocodylate buffer (Marivac, Quebec, Canada; pH 7.2) for 24 h at 4° C., post-fixed in 1% osmium tetroxide in cocodylate buffer (Electron Microscopy Sciences, PA) for 1 h, dehydrated serially in 50, 70, 90 and 95% ethyl alcohol for 30 min. at each concentration followed by 100% for 1 h. The sections were placed in 1:1 propylene oxide: epon gradually embedded and polymerized at 60° C. Ultra-thin sections were cut, stained with 2% uranyl acetate and 0.5% lead citrate (Electron Microscopy Sciences, PA), mounted on 200-mesh copper grid (Electron Microscopy Sciences, PA) and examined under a Phillips EM-200 transmission electron microscope (Phillips Company, Eindhoven, Holland) operated at 60 kV.

Demonstration of Vertical Transmission of FAdV from Broiler Breeders to their Progeny The objective of this experiment was to investigate if inoculation of FAdV in broiler breeder parents would lead to IBH in their progeny. Sixteen, 20-week-old broiler breeders were obtained from a local broiler breeder producer in Saskatchewan and maintained at the Animal Care Unit, Western College of Veterinary Medicine, University of Saskatchewan, Canada. A lighting program and feeding of broiler breeders were implemented according to the guidelines for Ross Broiler Breeders (Aviagen™ Inc., AL). Broiler breeders were divided into four groups, each group comprised three females, and was inoculated at 35-week of age with $1 \times 10^7$ ($CCID_{50}$) FAdV-x11a-like virus, FAdV-8a strain TR-59, FAdV-8a strain T8-A or FAdV-11 strain 1047 prepared from LH of clinical cases of IBH. Ground up liver was used to infect breeders. The genotype and viral dose was confirmed by sequencing and determining PFU/ml. Vaccine strains were derived from the same liver but propagated in specific pathogen free (SPF) chicken embryo primary livers for vaccination studies. Each group was introduced to a male broiler breeder. Males were inoculated with FAdV-x11a-like virus or FAdV-8a strain T8-A in respective groups and males were not inoculated with FAdV in the remaining two groups. For seven days post-inoculation of the parent breeders, eggs were collected and incubated until hatched. Ten broiler chicks were observed for three weeks post-hatch for clinical signs and mortality. Additionally, 10 broiler chicks were euthanized immediately after hatch and tissue samples were collected for FAdV and AAV isolation. Furthermore, 20 eggs were collected from each group for 7 days at the beginning of the $36^{th}$ and $37^{th}$-week, and chicks were observed for three weeks post-hatch. Broiler breeders were vaccinated against IBD at 2 weeks (Clonevac D-78: Intervet Canada Ltd., Ontario, Canada), 8 weeks (Bursa BlenM; Merial Canada Ltd., Quebec, Canada), and 18 weeks (Breedervac IV Plus, Intervet Canada Ltd., Ontario, Canada) and against CAV at 18 weeks (CAV-Vac; Intervet Canada Ltd., Ontario, Canada).

Virus Propagation, Isolation and Cell Culture Methods
Virus Isolation in Leghorn Male Hepatoma Cell Line Virus isolation was conducted in Leghorn male hepatoma (LMH) cell line obtained from American Type Culture Collection (ATCC#CRL-2117, VA) and maintained as described (Schat and Sellers, 2008). The LMH cells were propagated in Waymouth's MB 752/1 medium (1×) (Invitrogen Corporation, Auckland, NZ) supplemented with 10% fetal bovine serum, L-glutamine 200 mM/ml and 10 μl/ml gentamicin (Invitrogen Corporation, Auckland, NZ) in 75 cm² collagen-coated tissue culture flasks (Becton Dickinson, Bedford, Mass., UK) as described previously (Kawaguchi et al., 1987). Liver samples from 23 different IBH outbreaks were obtained during 2005 and 2006. Pooled liver samples from each barn were identified as FAdV-x11a-like virus, FAdV-8a strain TR-59, FAdV-8a/8b (interchangeably referred to FAdV 8a strain T-8A herein) (showed same percentage identity to both FAdV-8a strain T-8A and FAdV-8b strain 764) or FAdV-11 strain 1047 by sequencing and phylogenetic analysis at the Animal Health Laboratory, University of Guelph. Ten percent liver suspensions in Waymouth's MB 752/1 medium were inoculated at a multiplicity of infection (m.o.i.) of 1 to 80% confluent LMH cells and incubated for 1 h at 37° C. The remaining inoculum was washed 3 times with sterile phosphate-buffered saline (PBS) (pH 7.4) and incubated in 5% $CO_2$ and 85% humidity for 1 week or until a CPE was observed. Samples were considered negative if CPE was not observed after the second passage.

Animal challenge inoculums of FAdV liver homogenates (LHs) were prepared as follows. Ten percent liver suspensions were prepared in Waymouth's MB 752/1 medium (1×) (Invitrogen Corporation, Auckland, NZ) by homogenizing at 1000 rpm for 30 min (Polytron PT 3000, Kinematica, AG, Littau, Switzland). The suspensions were subjected to 6 cycles of freeze-thaw followed by centrifuging at 6000 rpm using a fixed-angle JA-10 rotor (Beckman Coulter, Inc., CA) for 30 min at 4° C. The supernatant was filtered through 5 μm and 2 μm pore-sized; 25 mm diameter-syringe filters (Millipore Ireland BV, Cork, Ireland) to remove debris. Finally, the suspensions were filtered through 0.45 μm and 0.22 μm pore-sized filters (Millipore Ireland BV, Cork, Ireland) to purify FAdV (Davis et al., 1996; Davis et al., 1995) and stored at −80° C. until used for animal inoculation described above.

Preparation of Chick Embryo Cell Culture

Chick embryo liver cell cultures were prepared from livers obtained from nine day old SPF chickens (Charles River Laboratories, CT). Livers were washed three times with sterile phosphate buffered saline; gall bladders were removed and chopped with crossed scalpels. Then, 20 ml of 0.5% trypsin+5.3 mM ethylene diamine tetra acitic acid (Corporation, Auckland, NZ), 30 ml of sterile PBS, 10,000 IU/ml penicillin G and streptomycin 10,000 mg/ml were prewarmed (37° C.), added and incubated at 37° C. for 5 min with vigorous intermittent shaking. The supernatant was filtered through double-layered sterile cheese cloth and centrifuged at 2000 rpm at 4° C. for 5 min. The pellet was resuspended at 1:400 ratio in Dulbecoo's Modified Eagle Medium with nutrient mixture F-12 (Ham) 1X (DMEM/F12 (1:1) (Invitrogen Corporation, Auckland, NZ) supplemented with 5% fetal bovine serum, 10,000 IU/ml penicillin G and streptomycin 10,000 mg/ml (Invitrogen, Auckland, NZ) by repeated gentle pipetting.

CEL cell suspension in DMEM/F 12 (1:1) (Invitrogen Corporation, Auckland, NZ) supplemented with 5% fetal bovine serum, penicillin G 10,000 IU/ml and streptomycin sulphate 10,000 μg/ml (Invitrogen Corporation, Auckland, NZ) were seeded at $2\times10^6$/ml in 75 cm$^2$ collagen-coated tissue culture flask (Becton Dickinson, Bedford, Mass., UK) and incubated in 5% $CO_2$ and 85% humidity at 37° C. to form confluent monolayers in 24 h.

Cell Culture Count

CEL cell suspension (prepared as above) is mixed thoroughly and mixed with 0.4% trypan blue in 0.85% saline (Invitrogen Corporation, Auckland, NZ) at 1:1 ratio and allow to stand for 15 min. Counting chambers of a improved Neubeuer hematocytometer (Bright-Line hemocytometer, 1/10 mm deep, Hausser Scientific Horsham, PA) is filled gently with the mixture and covered with a cover slip. The unstained cells in large squares (4 corners+1 center) on each side of the counting chamber are counted at 100 times magnification under the light microscope. The number of viable cells in each side of the counting chamber was determined by multiplying the number of viable cells counted chamber conversion factor and dilution factor, then dividing by the number of squares counted to obtain the cell count per milliliter.

Virus Isolation in Chick Embryo Liver Cells

Confluent CEL cell cultures were infected individually with LH (prepared above) at 1 m.o.i. at 37° C. for 1 h and remaining inoculum was washed 3 times with sterile PBS (pH 7.4), added and incubated in 5% $CO_2$ and 85% humidity for 5 days or until a CPE is observed. Samples were considered negative if CPE was not observed after the second passage. When maximum CPE was observed, cell cultures were harvested and subjected to 6 cycles of freeze-thaw followed by centrifugation at 2000 rpm for 10 min at 4° C. The supernatant were filtered through syringe filters with porosity of 0.45 μm (Millipore Ireland BV, Cork, Ireland) and stored at −80° C. until used for animal inoculation described in 2.3.1.

Virus Titration

The FAdV in LH and those propagated in CEL were titrated by end point dilitiondilution assay as described previously (Villegas, 2008). Briefly, ten-fold serial dilutions of LH or CEL propagated FAdV in Waymouth's MB 752/1 medium (1x) were inoculated to 80% confluent LMH cells in collagen-coated 96-well, flat-bottom microtiter plates, and incubated at 37° C. for 1 h. The remaining inoculum was washed once with Maymouth's MB 752/1 medium and filled with Waymouth's MB 752/1 (1x) supplemented with 10 fetal bovine serum, gentamicin 10 mg/ml and incubated in 5% $CO_2$ at 37° C. The plates were observed daily under 20 magnification of an inverted microscope (Olympus CKX 41, Olympus Corporation, Japan) for CPE. The proportionate distance (PD) between adjacent dilutions is calculated by percentage infected at dilution next above 50% minus 50% divided by percentage infected at dilution next above 50% minus percentage infected at dilution next below 50%. The 50% end point were calculated by the formula: log of the 50% end point=($_{log}$dilution above 50%−(PDx$_{log}$dilution factor) and TCID$_{50}$ in LMH cell line expressed as positive exponential with one decimal point mililiter.

Sequencing and Genotyping

The L1 region of the FAdV hexon protein gene was amplified by PCR as described previously (Ojkic et al., 2008b). Nucleotide sequences of PCR products were determined at the Laboratory Services, Molecular Supercentre, University of Guelph. Sequence editing and phylogenetic analysis were done by using the LaserGene software package (DNAStar, Inc., Madison, Wis.). The amino acid sequence of the variable region of L1 was determined and analyzed. A 158 amino acid sequence from residues 130 to 287, based on the FAdV-9 hexon gene sequence, was used to calculate sequence identities and construct phylogenetic trees (Neumann et al., 1987).

Statistical Analysis

Survival data were analyzed by Kruskhal-Wallis test using SPSS 16.0 fro Windows® (SPSS Inc., Chicago, Ill., USA) and a p value <0.05 was considered significant. The graphic display was done with GraphPad PRISM 4.0 (GraphPad Software Inc., SanDiego, Calif.).

Results

Figure 9:
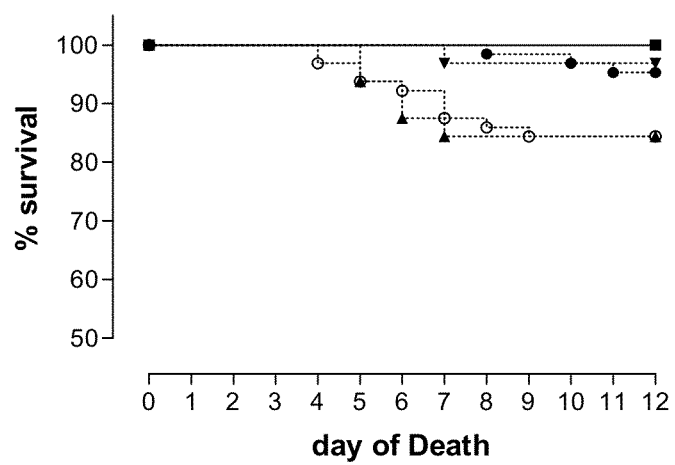
Figure 10:
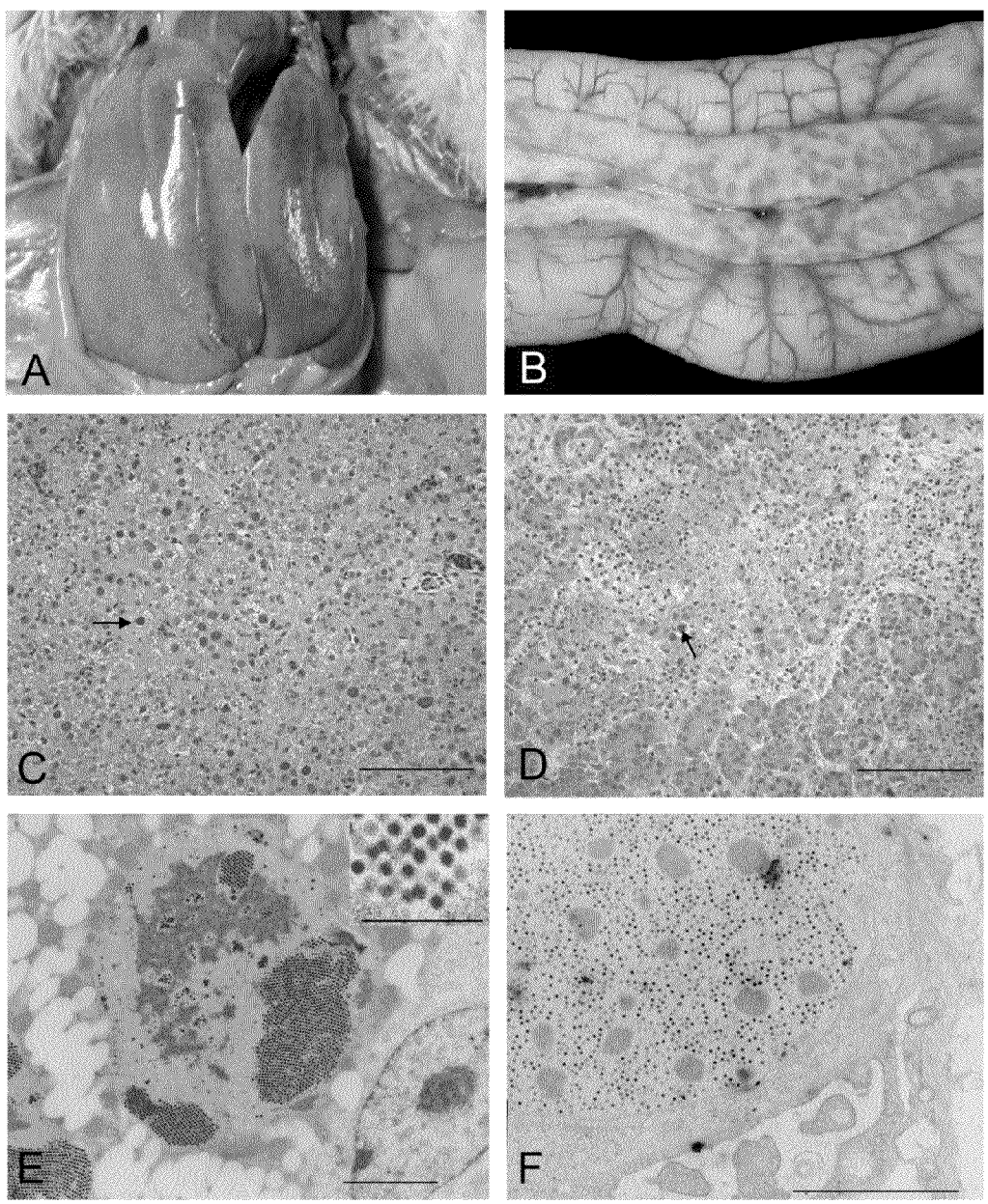

Inclusion Body Hepatitis Animal Model Development in 14-day-old Broiler Chickens No statistical significance was observed among different doses and virus preparations (LH or CEL) of FAdV by Kruskhal-Wallis test (p>0.05). The IBH mortality for each FAdV serotype was calculated as a percentage of IBH deaths. The mortality associated with different serotypes of FAdV varied from 5-15%. Birds inoculated with either FAdV-8a strain TR-59 or FAdV-11 strain 1047 demonstrated 5% mortality; in contrast, birds inoculated with either FAdV-8a strain T8-A or FAdV-x11a-like virus demonstrated 15% mortality (FIG. 9). Inclusion body hepatitis was reproduced in broilers with FAdV either propagated in CEL or by purified FAdV from LH of clinical cases (FIG. 10A, B). All of the four doses ($1\times10^4$-$1\times10^7$ CCID$_{50}$) of FAdV were able to reproduce IBH in broilers. Furthermore, IBH was caused by either CEL-propagated FAdV or FAdV isolated from LH of clinical cases (Table 3). Birds that died or were euthanized had necrotizing, hemorrhagic hepatitis with basophilic INIB (FIG. 10.A, B). Some birds had necrotizing pancreatitis with INIB (FIG. 10.C, D). Electron microscopic examination revealed non-enveloped, hexagonal shape viral particles measuring 70-90 nm in crystalline arrays in nuclei of hepatocytes (FIGS. 10 E and F). A few birds that died of IBH had diffuse yellow discoloration of the body fat and focal to extensive hemorrhages in the proventriculus.

Although birds were comingled, the respective genotype of FAdV was isolated from IBH infected livers corresponding to their challenge FAdV inoculums. Clinical signs were observed only in birds that developed gross lesions of IBH. All the birds that did not develop clinical IBH remained clinically normal until the end of the experiment and did not demonstrate any gross lesions at necropsy.

Demonstration of Vertical Transmission of Adenoviruses from Broiler Breeders to their Progeny Clinical signs of IBH or mortality were not observed in broiler breeders. Broilers hatched from the eggs collected from breeders during 1-7-day post-FAdV-8a strain T8-A inoculation reproduced the clinical IBH in 30% (3 of 10 birds)

of broilers at 6-7 days post-hatch. Broilers that died with clinical IBH had hemorrhagic, necrotizing hepatitis with basophilic INIB. The pancreas had multifocal necrotizing pancreatitis with INIB. The remaining seven of ten birds from FAdV-8a strain T8-A inoculated parents did not develop any clinical signs of IBH during the experiment. [FAdV-8a strain T8-A was confirmed by virus isolation or PCR (Table 3)]. Further, FAdV-8a strain T8-A was isolated from liver, spleen and bursa of Fabricius from all three birds that died of IBH (Table 3). FAdV was isolated from the liver from one of the seven clinically normal birds at the termination of the experiment (Table 3). No FAdV was isolated from the liver samples of another group of ten birds originating from FAdV-8a strain T8-A inoculated parents at the time of hatch (Table 3). In contrast, FAdV-8a strain T8-A was isolated from the spleen, yolk sac and bursa of Fabricius from five of the same ten birds (Table 3). No AAV was detected in any of the birds in which FAdV was isolated. No clinical signs or IBH were observed in any of the broilers from broiler breeder parents inoculated with FAdV-x11a-like virus, FAdV-8a strain TR-59, or FAdV-11 strain 1047 during the entire duration of the experiment. None of the broiler progeny derived from eggs collected at week 36 or 37 developed any clinical signs or IBH during the three week post-hatch period.

TABLE 3

Fowl adenovirus isolation in the broiler progeny originated from broiler breeders inoculated with FAdV-8a strain

|  | Liver | Spleen | Bursa of Fabricius | Yolk sac |
|---|---|---|---|---|
| Day 1 | 0/10 | 4/10 | 4/10 | 5/10 |
| Day 6-7 | 3/3 | 3/3 | 3/3 | * |
| Day 21 | 1/7 | 0/7 | 0/7 | * |

*yolk sac absorbed at that age

TABLE 4

Mortality of broilers inoculated with various doses of FAdV propagated in chicken embryo liver and liver homogenate of clinical cases of IBH

| FAdV preparation | Dose TCID$_{50}$ | FAdV-x11a-like virus | FAdV-8a strain TR-59 | FAdV-8a strain T8-A | FAdV-11 strain 1047 |
|---|---|---|---|---|---|
| LH | $1 \times 10^4$ | 1/8 | 0/8 | 5/8* | 0/8 |
|  | $1 \times 10^5$ | 2/8 | 1/8 | 1/8 | 1/8 |
|  | $1 \times 10^6$ | 1/8 | 1/8 | 2/8 | 0/8 |
|  | $1 \times 10^7$ | 2/8 | 0/8 | 0/8 | 0/8 |
| CEL | $1 \times 10^4$ | 1/8 | 0/8 | 0/8 | 0/8 |
|  | $1 \times 10^5$ | 0/8 | 0/8 | 0/8 | 1/8 |
|  | $1 \times 10^6$ | 2/8 | 0/8 | 2/8 | 0/8 |
|  | $1 \times 10^7$ | 1/8 | 1/8 | 0/8 | 0/8 |
| Control |  |  | 0/8 |  |  |

[LH = liver homogenate, CEL = chicken embryo liver, Control = saline] (n = 8) p < 0.05 in comparison to the control group Discussion Historically, IBH was generally considered a secondary disease in broiler associated with primary immunosuppression following infection with IBDV (Fadly et al., 1976; Rosenberger et al., 1975) or CAV (Rosenberger et al., 1974; Toro et al., 2000). Under these circumstances immunosuppressed birds exposed to FAdV from the environment would eventually develop a clinical disease. IBH has also been occasionally described as a primary disease causing economic losses in the broiler industry without prior immunosuppression (Grgic et al., 2006). Under these circumstances it was suggested that vertical transmission of FAdVs from broiler breeders caused the clinical disease of IBH in their progeny (Toro et al., 2000; Toro et al., 2001b). It has also been demonstrated that vaccination against IBH and IBH/HPS in broiler breeders controlled vertical transmission of FAdV (Grimes, 1992; 2007; Toro et al., 2001a).

The objective of this study was to examine if IBH is a primary disease in commercial broiler chickens. Antibody levels against IBDV and CAV were high in broiler breeders due to vaccinations against IBDV and CAV and hence, their progeny had the expected level of maternal Ab against IBDV and CAV at hatch. Clinical IBH with necrotizing, hemorrhagic lesions and INIB in the liver were seen in all dead or clinically diseased euthanized birds following challenge with FAdV. Mortality was 15% in groups challenged with FAdV-x11a-like virus or FAdV-8a strain T8-A; in contrast, mortality was 5% in birds challenged with FAdV-8a strain TR-59 or FAdV-11 strain 1047. The difference in mortality in groups infected with different IBH genotypes could be associated with the virulence of different strains of FAdV. In a few birds, necrotizing pancreatitis with INIB was evident as shown in previous studies (Grgic et al., 2006; Philippe et al., 2007). The mortality and the clinical disease of IBH were caused by as low as $1 \times 10^4$ TCID$_{50}$ to high as $1 \times 10^7$ TCID$_{50}$ of FAdV. Also, IBH was caused by both CEL cell culture-grown FAdV, and FAdV isolated from clinical cases of IBH. Although all the experimental groups were comingled during the entire experiment, there was no evidence of horizontal transmission of adenoviruses between the groups since the corresponding group challenge genotype of adenovirus was isolated from each of the bird each group.

Although, there were several attempts made previously to demonstrate vertical transmission of FAdV in broiler chickens (Grgic et al., 2006; Neumann et al., 1987; Philippe et al., 2005), this is the first demonstration of vertical transmission of FAdV-8a strain T8-A by virus isolation in commercial broiler chickens following FAdV inoculation of their parents. This observation was confirmed by isolating FAdV-8a strain T8-A in the liver of IBH infected birds corresponding with the challenge inoculums of their parents. Also FAdV-8a strain T8-A was isolated from the spleen and bursa of Fabricius of these birds. Experimental vertical transmission of FAdV was seen in day-7 post-hatch broilers and this is compatible with data from an IBH field study conducted in Canada where clinical IBH was reported to range from 7-91 days of age (Adair and Fitzgerald, 2008)

In conclusion, this study demonstrated IBH is a vertically transmitted primary disease in broiler chickens without apparent immunosuppression.

Example 4

Control of Inclusion Body Hepatitis in Broiler Chickens by Vaccinating their Parents with Inactivated Adenoviruses Inclusion body hepatitis (IBH) is an emerging, economically important viral disease of 2 to 6 weeks old broiler chickens. The objective of this study was to prevent IBH in broiler chickens by vaccinating their parents with a vaccine containing inactivated FAdV Ag formulated with O/W emulsion as an adjuvant. Four groups of broilers breeders were vaccinated with either FAdV-8a strain T8-A ($2 \times 10^7$ or $2 \times 10^4$ CCID$_{50}$) formulated with 20% O/W or FAdV x11a-like virus ($2 \times 10^7$ or $2 \times 10^4$ CCID$_{50}$) formulated with 20% O/W emulsion at the age of 12 and 15 week. The control group received saline. Eggs were collected and incubated until hatched for challenge protection studies. Broiler progeny were challenged with FAdV-8a strain T8-A at a dose of $1 \times 10^7$ TCID$_{50}$ to study the immunoprotective effect of the vaccine. Although, survival of broiler chickens following FAdV-8a strain T8-A challenge was not significantly different among vaccinated and non-vaccinated groups (p>0.05), immunoprotection was enhanced by increased dose of FAdV-8a strain T8-A Ag in the vaccine. Further studies are necessary to optimize the formulation of FAdV-8a strain T8-A with O/W emulsion or vaccination stratergy to improve the utility of this FAdV vaccine in the poultry industry.

The objective of this study was to evaluate protection of broiler chickens against IBH by vaccinating their parents with an inactivated adenoviral vaccine.

Materials and Methods

Management of Broiler Breeders

All procedures involving animals were approved by the University of Saskatchewan Animal Care Committee as described in above. Thirty, 10 week-old commercial broiler breeders (25 pullets (young female) and 5 males) were obtained from a local commercial broiler breeder producer, identified individually by wing-tag, (Ketchum's Clicher Tamperproof Wing Tag, Ketchun Manufacturing, Surrey, UK) and housed in the Animal Care Unit, Western College of Veterinary Medicine, University of Saskatchewan. They were randomly divided into five groups and placed in five pens; each with 5 females and one male. Lighting and feeding programs were implemented according to guidelines for Ross Broiler Breeders (Aviagen™ Inc., AL). They were vaccinated against infectious bursal disease at 2 weeks (Clonevac D-78; Intervet Canada Ltd., Ontario, Canada), 8 weeks (BursaBlenM; Merial Canada Ltd., Quebec, Canada), and 18 weeks (Breedervac IV Plus, Intervet Canada Ltd., Ontario, Canada) and against CAV at 18 weeks of age (CAV-Vac; Intervet Canada Ltd., Ontario, Canada).

FAdV Vaccination of Broiler Breeders

Two FAdVs isolates; FAdV-8a strain T8-A and FAdV-x11-like virus (sequenced at Animal Health Laboratory, University of Guelph) obtained from outbreaks of IBH in Saskatchewan were used in this study. These isolates were inactivated by β-propriolactone as describes previously (Garlick and Avery, 1976), and formulated with 20% O/W emulsion (EMULSIGEN®-D, which is supplemented with DDA, MVP Laboratories Inc., NE) in a dose volume of 0.1 ml to vaccinate broiler breeders. At 12 and 15 weeks-of-age, four groups were vaccinated subcutaneously in the neck using a 25-gauge needle as follows: (a) FAdV-8a strain T8-A, (high dose) ($2 \times 10^7$ $CCID_{50}$) formulated with 20% O/W emulsion; (b) FAdV-8a strain T8-A, (low dose) ($2 \times 10^4$ $CCID_{50}$) formulated with 20% O/W emulsion; (c) FAdV-7 strain x11a, (high dose) ($2 \times 10^7$ $CCID_{50}$) formulated with 20% O/W emulsion; (d) FAdV-7 strain x11a, (low dose) ($2 \times 10^4$ $CCID_{50}$) formulated with 20% O/W emulsion. The control group received 0.1 ml saline.

Management of Broiler Chickens

When broiler breeders were 34 week of age, eggs from each group were hatched, and sixty chickens derived from each group were identified individually by neck tag (Swiftack Poultry Tags, Heartland Animal Health Inc., MO) and reared in an isolation facility. Water and feed were provided ad libitum. Air in the room was exhausted through a high efficiency particulate air (HEPA) filter and replaced with non-recirculated intake air at a rate of 18 changes/h. Air pressure differentials and strict sanitation were maintained in this facility. Photoperiods of 24 h per day for the first 3 days and 16 h. per day for the remaining 21 days were established. Room temperatures were maintained at 30-32° C. for the first three days and 28-30° C. for the remaining duration of the experiment.

Inclusion Body Hepatitis Challenge of the Progeny

Broiler progeny were challenged with FAdV-8a strain T8-A to evaluate homologous or heterologous protection. When broiler breeders were 34 weeks-of-age, 60, 14-day-old broiler chickens each from groups (a), (b) and the control group were inoculated with $1 \times 10^7$ $CCID_{50}$ FAdV-8a strain T8-A as previously described for the homologous challenge. When broiler breeders were 37 weeks-of-age, 60, 14-day-old broiler chickens each from groups (c), (d) and the control group were inoculated with $1 \times 10^7$ $CCID_{50}$ FAdV-8a strain T8-A as previously described for the heterologous challenge. All the birds were observed for clinical signs thrice daily for 10 days following FAdV challenge. Daily clinical scores were recorded as follows: 0=normal; 1=hesitate to move and tire quickly; 2=unable to stand or forage and euthanized; 3=dead. Daily mortality was recorded. Dead or euthanized chickens were necropsied immediately, and tissues from the liver were fixed in 10% buffered formalin.

Statistical Analysis

Survival data were analyzed by Kruskal-Wallis test using SPSS 16.0 for Windows® (SPSS Inc., Chicago, Ill., USA) and a p value <0.05 was considered significant.

Results

Management of Broiler Breeders

Broiler breeders maintained normal health, egg production and fertility following vaccination with FAdV-8a strain T8-A until termination of the animal experiment at 45 weeks.

Inclusion Body Hepatitis Challenge of the Progeny

Figure 11:
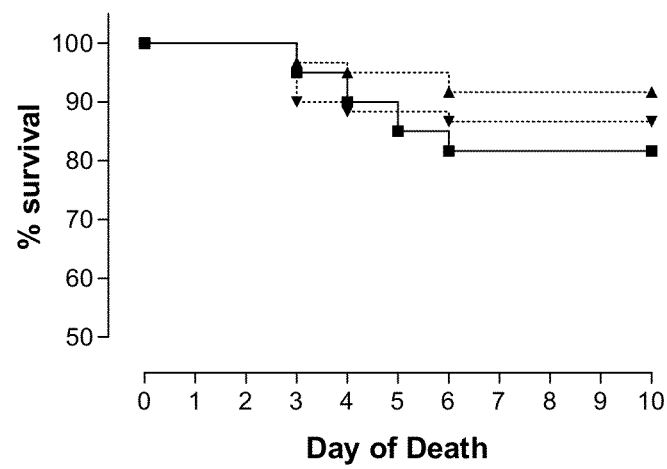

In both homologous and heterologous challenge experiments, mortality due to IBH occurred between 3-6 days post inoculation. The IBH mortality varied from 8-20% (Table 5). In both homologous and heterologous challenges survival of broilers from FAdV vaccinated groups were not significantly different compared to the control group (progeny of unvaccinated broiler breeders) (FIGS. 11 and 12.). All dead or euthanized chickens had enlarged, friable, pale yellow livers (FIG. 13.A). Histologically, the affected livers had focal to extensive areas of necrosis with the presence of large, basophilic inclusion bodies in hepatocytes (FIG. 13.B). In both homologous and heterologous challenges, progeny derived from breeders vaccinated with a high dose of FAdV Ag tend to have more protection against IBH, although the protection was not statistically significant (p=0.275).

TABLE 5

IBH mortality following homologous and heterologous challenges

| Breeder group | IBH mortality in the progeny |
|---|---|
| Homologous challenge | |
| Saline | 12/60 |
| FAdV-8a strain T8-A, $2 \times 10^7$ $CCID_{50}$ | 5/60 |
| FAdV-8a strain T8-A, $2 \times 10^4$ $CCID_{50}$ | 8/60 |
| Heterologous challenge | |
| Saline | 8/60 |
| FAdV-7 strain x11a, $2 \times 10^7$ $CCID_{50}$ | 5/60 |
| FAdV-7 strain x11a, $2 \times 10^4$ $CCID_{50}$ | 11/60 |

Discussion

Disease prevention by vaccination is an integral part of poultry management and disease control programs. Since 1916, inactivated vaccines formulated with emulsion-based adjuvants have been in common practice in the poultry industry (Jansen et al., 2007). Also, immunization of parent flocks against vertically-transmitted viral diseases such as CAV and AE was very successful with live vaccines (Calnek, 1997; 2008; Engstrom, 1999).

A decrease in mortality was demonstrated (from 20% 8.3%) of broilers due to IBH by vaccinating their parents with inactivated Ags of FAdV formulated with O/W as an adjuvant. Although, it was not statistically significant, increased immunoprotection was observed against IBH by increasing the Ag dose of the FAdV in the vaccine.

It was demonstrated that IBH is a primary disease in broilers by development of IBH in commercial broilers without immunosuppression. Development of IBH was achieved by experimental reproduction of the clinical disease of IBH in 14-day-old broiler chickens by inoculation of any of four FAdV serotypes isolated from clinical cases of IBH in Saskatchewan. Moreover, vertical transmission of FAdV and associated clinical disease of IBH in broilers were demonstrated following inoculation of FAdV in broiler breeders. In the animal model of IBH, the mortality associated with different genotypes of FAdV ranged from 5 to 15 to 15%. Birds that were inoculated with either FAdV-8a strain TR59 or FAdV-11 strain 1047 demonstrated 5% mortality; in contrast, birds inoculated with either FAdV-8a strain T8-A or FAdV-x11a like-virus demonstrated 15% mortality. IBH was reproduced in broilers with FAdV either propagated in CEL or by purified FAdV from LH of clinical cases. IBH in broilers was reproduced following administration of any of these four doses ($1\times10^4$-$1\times10^7$ $CCID_{50}$) of FAdV. Birds that died or were euthanized had necrotizing, hemorrhagic hepatitis with basophilic INIB. Some birds also had necrotizing pancreatitis with INIB. Electron microscopic examination revealed non-enveloped, hexagonal-shaped viral particles measuring 70-90 nm in crystalline arrays in nuclei of hepatocytes. Although birds were comingled, the respective genotype of FAdV was isolated from IBH infected livers corresponding to their challenge FAdV inoculums. Electron microscopic examination revealed non-enveloped, hexagonal-shaped viral particles measuring 70-90 nm in crystalline arrays in nuclei of hepatocytes and pancreatic acinar cells which confirms the predilection of FAdV for these cells.

Example 5

FAdVs were propagated in 14-day-old SPF chick embryo liver cell culture (CEL) for animal challenge studies (Animal Health Laboratory, Guelph).

Liver from 12-16 day old embryos were harvested, minced and transferred to a flask. The liver pieces were washed with PBS and subjected to trypsin treatment (0.25%) with shaking. The supernatant suspension was harvested by pouring the suspension through cheesecloth into a centrifuge tube and centrifuging. Cell are plated by resuspending in 100 ml of growth medium (EMEM containing 10% fetal calf serum)/ 0.25 ml of packed cells and dispensing 4 mls at a density of $1\times10^6$ to $2\times10^6$ cells/ml in 25 cm$^2$ tissue culture flasks. Cells were incubated at 37° C. Cell yield was optionally calculated prior to plating for example using a hemocytometer.

Liver cells were inoculated by contacting cells with inoculum at about 23° C. on a rocker platform for 30 minutes. Inoculum was washed off with EMEM and cells were maintained in EMEM+2% FCS.

The inoculum was prepared by homogenizing tissues to prepare a 10-15% suspension comprising virus or by vortexing swabs comprising virus to expel material from swab. Tissue suspensions or swabs were centrifuged to sediment tissue decries and most bacteria. Supernatant was aseptically removed and filtered through a 0.45 um filter into a vial. Inoculum is added undiluted or diluted 10× and 100×.

Virus was harvested when evidence of cytopathic effect (CPE) was observed. CPE is confirmed by morphologic alteration of cells, formation of giant cells and syncytia, viral nucleic acid or viral antigens detection, or other evidence of viral particles.

Example 6

FAdV8a, FAdV8ab, FAdV11 and FAdV7 (FAdVX11a) are the most common serotypes across Canada. (Ojkic, D., Martin, E., Swinton, J., Vaillancourt, J. P., Boulianne, M., and Gomis, S. (2008b). Genotyping of Canadian isolates of fowl adenoviruses. Avian Pathol. 37(1): 95-100. Gomis, S., Goodhope, R., Ojkic, D., and Willson, P. (2006). Inclusion body hepatitis as a primary disease in broilers in Saskatchewan, Canada. Avian Dis. 50(4): 550-555)

It is desirable to protect broilers against the common serotypes (causing IBH) by vaccination. It is demonstrated herein that cross protection can occur for example by demonstrating that the FAdV8ab vaccine protects against FAdV11 challenge (FIG. 5). A combination of FAdV in a vaccine is tested for broad protection against FADV species D & E. Serotypes D and E are distinct enough (at least at molecular level) to put them into different species.

For example FAdV serotypes in species D and E of FAdV nomenclature are as follows:

Fowl adenovirus D Serotypes: (FAdV-2, FAdV-3, FAdV-9, FAdV-11)

Fowl adenovirus E Serotypes: (FAdV-6, FAdV-7, FAdV-8a, FAdV-8b FAdV 8a/8b).

A vaccine comprising FAdVs from both D and E together protect birds against multiple species D and E FAdV viruses, in addition to the strains in the combination.

Broiler breeders will be vaccinated as described above according to the following:

Vaccination Groups
Control—no vaccination
FAdV-8a—($1\times10^5$/bird)-oral
FAdV-11—($1\times10^5$/bird)-oral
FAdV-8a ($1\times10^5$/bird)+FAdV-11 ($1\times10^5$/bird)-oral
FAdV8ab ($1\times10^5$/bird)+FAdV11 ($1\times10^5$/bird)-oral
FAdV2 ($1\times10^5$/bird)+FAdV 7 ($1\times10^5$/bird)-oral
FAdV2 ($1\times10^5$/bird)+FAdV11+FAdV 7+FAdV8ab ($1\times10^5$/bird)-oral
FAdV2 ($1\times10^5$/bird)+FAdV11+FAdV 7+FAdV8a ($1\times10^5$/bird)-oral Broiler progenies will be challenged with FAdV-8a, FAdV-11, FAdV-8a/8b FAdV2 and/or FAdV-7 as described above to study the homologous and heterologous protection.

TABLE 6

Hexon Loop Sequences of Isolates Used in Examples

FAdV-7
GenBank: EF685492.1
Fowl adenovirus DDO-2007 isolate 04-53357-119 hexon protein gene, partial cds
FeaturesSequence
LOCUS       EF685492                1247 bp    DNA     linear   VRL 06 Aug. 2007
DEFINITION  Fowl adenovirus DDO-2007 isolate 04-53357-119 hexon protein gene, partial cds.
ACCESSION   EF685492
VERSION     EF685492.1  GI:154362589
SOURCE      Fowl adenovirus DDO-2007
  ORGANISM  Fowl adenovirus DDO-2007
            Viruses; dsDNA viruses, no RNA stage; Adenoviridae; Aviadenovirus; unclassified Aviadenovirus.

REFERENCE   1  (bases 1 to 1247)
  AUTHORS   Ojkic,D., Martin,E., Swinton,J., Vaillancourt,J.-P., Boulianne,M. and Gomis,S.
  TITLE     Genotyping of Canadian isolates of Fowl adenoviruses
  JOURNAL   Unpublished
REFERENCE   2  (bases 1 to 1247)
  AUTHORS   Ojkic,D., Martin,E., Swinton,J., Vaillancourt,J.-P., Boulianne,M. and Gomis,S.
  TITLE     Direct Submission
  JOURNAL   Submitted (18 Jun. 2007) Animal Health Laboratory, University of Guelph, Box 3612, University of Guelph, Guelph, Ontario N1H 6R8, Canada
FEATURES             Location/Qualifiers
     source          1..1247
                     /organism="Fowl adenovirus DDO-2007"
                     /mol_type="genomic DNA"
                     /isolate="04-53357-119"
                     /db_xref="taxon:457007"
                     /collection_date="2004"
     CDS             <1..>1247
                     /note="loop 1"
                     /codon_start=1
                     /product="hexon protein"
                     /protein_id="ABS81122.1"
                     /db_xref="GI:154362590"

SEQ ID NO: 1

/translation="TEKAQRLQIRFYPTQTDDTPNSYRVRYSLNVGDSWVLDMGATYF
                     DIKGVLDRGPSFKPYGGTAYNPLAPREAFFNNWIEDEDNNTSITGQMTNPYTNEQQNT
                     ATATAGAIASVSGSYPNPNVGLAISEMGALTPTLAAQVGLAGRFAKVSSENTRLAYGA
                     YVKPIKDDGSQSLGTTPYYVLDTTAQKYLGVMGVEDFTQSLTYPDSLLIPPPSEYRAV
                     NSGVMKANRPNYIGFRDNFINLLYHDTGVCSGTLNSERSGMNVVVELQDRNTELSYQY
                     MLADMMSRHHYFALWNQAVDQYDHDVRVFNNDGYEEGVPTYAFSPEGTGQGPISSANI
                     TLSGVKVYTNGQNDKGTEVANTTTYLNAGTVPSYEIDLAASQRRNFIITNIADYLPDK
                     YKYNISGFNPETDNVDPTTYAYM"

/note="N-terminal domain; Region: Adeno_hexon; pfam01065"
                     /db_xref="CDD:110092"

ORIGIN
SEQ ID NO: 2

```
   1 accgagaagg cccagcggct tcagatcagg ttctatccca cccagacgga cgacaccccc
  61 aacagttacc gggttcggta cagcttaaac gtgggggaca gctgggtgtt ggacatggga
 121 gcgacctact tcgacatcaa aggggtgctc gacagaggtc cttccttcaa gccctacggc
 181 ggcacggctt acaaccccct ggccctcgc gaagccttct taacaactg gatcgaggac
 241 gaagacaaca atacatccat cacggggcaa atgaccaatc cgtacacgaa cgagcagcaa
 301 aacacagcta cggcaacagc tggggcaatc gccagcgttt caggctctta tcctaaccct
 361 aacgtggggc tggccattag cgaaatggga gccctcaccc cgacactagc agcacaggtc
 421 ggcctggccg gacgcttgc caaggtgtcg agcgagaaca cgcgcctggc ttatggagcg
 481 tatgtgaagc ctataaaaga cgacggctct cagtcacttg gaacaacgcc ttactacgtg
 541 ttagacacca ccgcacagaa atacttgggc gtcatggggg tagaagactt tacacaaagt
 601 cttacctacc cagacagtct gttaatcccc cctccttctg agtacagagc ggttaacagc
 661 ggggtgatga agccaacag acccaactac atcgggttcc gtgacaattt catcaacctc
 721 ctataccacg ataccggcgt gtgctccggg accctcaact ccgaacggtc aggcatgaac
 781 gtggtggtgg aattgcagga ccgaaatacc gaactcagtt accagtacat gctcgccgat
 841 atgatgtcca ggcatcacta tttcgctctc tggaaccagg ccgtggatca gtacgaccac
 901 gacgtgcgcg tgtttaacaa cgacggctac gaggagggcg tccccacgta cgccttctcg
```

TABLE 6-continued

Hexon Loop Sequences of Isolates Used in Examples

```
 961 cccgagggta caggacaggg acccatcagt tcagcaaata tcacgctttc tggtgtcaag
1021 gtgtacacta acggacagaa cgacaagggc accgaagtcg caaacactac gacgtatctc
1081 aatgccggca ccgttccttc ctacgagatc gatctggcgg cctctcaacg gcgaaacttt
1141 atcatcacca atatcgccga ctacctgccc gataagtaca agtacaacat ttccgggttc
1201 aaccccgaaa ccgataacgt agaccccacg acttacgcgt acatgaa
```

FAdV-8a
GenBank: EF685486.1
Fowl adenovirus E isolate 04-53357-125 hexon protein gene, partial cds
FeaturesSequence
LOCUS EF685486 860 bp DNA linear VRL 06 Aug. 2007
DEFINITION Fowl adenovirus E isolate 04-53357-125 hexon protein gene,
partial cds.
ACCESSION EF685486
VERSION EF685486.1 GI:154362577
KEYWORDS.
SOURCE Fowl adenovirus E
ORGANISM Fowl adenovirus E
Viruses; dsDNA viruses, no RNA stage; *Adenoviridae*; *Aviadenovirus*.
REFERENCE 1 (bases 1 to 860)
AUTHORS Ojkic,D., Martin,E., Swinton,J., Vaillancourt,J.-P., Boulianne,M.
and Gomis,S.
TITLE *Genotyping of Canadian isolates of Fowl adenoviruses*
JOURNAL Unpublished
REFERENCE 2 (bases 1 to 860)
AUTHORS Ojkic,D., Martin,E., Swinton,J., Vaillancourt,J.-P., Boulianne,M.
and Gomis,S.
TITLE *Direct Submission*
JOURNAL Submitted (18 Jun. 2007) Animal Health Laboratory, University of
Guelph, Box 3612, University of Guelph, Guelph, Ontario N1H 6R8,
Canada
FEATURES Location/Qualifiers
source 1..860
/organism="Fowl adenovirus E"
/mol_type="genomic DNA"
/isolate="04-53357-125"
/db_xref="taxon:190065"
/collection_date="2004"
CDS <1..>860
/note="loop 1"
/codon_start=1
/product="hexon protein"
/protein_id="ABS81116.1"
/db_xref="GI:154362578"

SEQ ID NO: 3

/translation="PTRNVTTEKAQRLQIRFYPTQTDDTPNSYRVRYSLNVGDSWVLD
MGATYFDIKGVLDRGPSFKPYGGTAYNPLAPREAFFNNWIAEDGNKTTITGQMSNPYE
NTTQTAAAETAAVVASVSGSYPNPNSGPGISEMGALSTTLAAQVGLAGRFAKVSSENT
RLAYGAYVKPLKNDGSQSLVQTPYYVMDSGSTKYLGVMGVEDFTDSLTYPDSLLIPPP
IEYGTVNTGVMKANRPNYIGFRDNFINLLYHDTGVCSGTLNSERSGMNVVVELQDRNT
ELSYQYMLAD"
misc_feature 1..>860
/note="N-terminal domain; Region: Adeno_hexon; pfam01065"
/db_xref="CDD:110092"

ORIGIN
                                                              SEQ ID NO: 4
   1 cctacccgca atgtcactac cgagaaggcc cagcggcttc agatcaggtt ctaccccacc
  61 cagacggacg acacccccaa cagctaccgg gttcggtaca gcctaaacgt gggggacagc
 121 tgggtgttgg acatgggagc gacctacttc gacatcaaag gggtgctcga cagaggtcct
 181 tccttcaagc cctacggcgg cacggcttac aaccccctgg cccctcgcga agccttcttt
 241 aacaactgga tcgcggaaga cggcaacaag acaaccatca ccgggcaaat gtctaacccc
 301 tatgagaata ccactcaaac ggccgcagcg gaaacagccg ccgtcgtcgc cagcgtctcc
 361 ggcagctacc ctaatcccaa ctcgggtccg ggcattagcg aaatggggc gctcagcact
 421 acgctagcgg ctcaggtcgg tctagccggt cgcttcgcga agtatccag cgagaacacg
 481 cgtctggctt acggggcgta cgtcaagccc ctgaagaacg acggctctca gtctctggtg
 541 caaacacctt actacgtcat ggacagcggg agcacgaaat atttgggtgt gatgggggta
 601 gaggacttta ccgatagcct gacctacccc gacagtctac tgatcccgcc tcctatcgag
 661 tacggaacgg tcaataccgg ggtgatgaaa gctaacagac caattacat cgggttccgt
 721 gacaattca tcaacctcct gtaccacgat accggcgtgt gctccggcac cctgaactcc
 781 gagcggtccg gcatgaacgt ggtcgtagaa ctgcaggacc gaaacaccga actcagttac
 841 cagtacatgc tcgccgacat
```

TABLE 6-continued

Hexon Loop Sequences of Isolates Used in Examples

FAdV-8a/8b
GenBank: EF685508.1
Fowl adenovirus E isolate 04-53357-74 hexon protein gene, partial cds
FeaturesSequence
LOCUS EF685508 1301 bp DNA linear VRL 06 Aug. 2007
DEFINITION Fowl adenovirus E isolate 04-53357-74 hexon protein gene,
partial cds.
ACCESSION EF685508
VERSION EF685508.1 GI:154362621
KEYWORDS.
SOURCE Fowl adenovirus E
ORGANISM Fowl adenovirus E
Viruses; dsDNA viruses, no RNA stage; Adenoviridae; Aviadenovirus.
REFERENCE 1 (bases 1 to 1301)
AUTHORS Ojkic,D., Martin,E., Swinton,J., Vaillancourt,J.-P., Boulianne,M.
and Gomis,S.
TITLE Genotyping of Canadian isolates of Fowl adenoviruses
JOURNAL Unpublished
REFERENCE 2 (bases 1 to 1301)
AUTHORS Ojkic,D., Martin,E., Swinton,J., Vaillancourt,J.-P., Boulianne,M.
and Gomis,S.
TITLE Direct Submission
JOURNAL Submitted (18 Jun. 2007) Animal Health Laboratory, University of
Guelph, Box 3612, University of Guelph, Guelph, Ontario N1H 6R8,
Canada
FEATURES Location/Qualifiers
source 1..1301
/organism="Fowl adenovirus E"
/mol_type="genomic DNA"
/isolate="04-53357-74"
/db_xref="taxon:190065"
/collection_date="2004"
CDS <1..>1301
/note="loop 1"
/codon_start=1
/product="hexon protein"
/protein_id="ABS81138.1"
/db_xref="GI:154362622"

SEQ ID NO: 5

/translation="TEKAQRLQIRFYPTQTDDTPNSYRVRYSLNVGDSWVLDMGATYF
DIKGVLDRGPSFKPYGGTAYNPLAPREAFFNNWIEDDGNNTTITGQMTNPYKNEAQNT
ATATAAAIASVSGSYPNPNVGLAISEMGALTPTLAAQVGLAGRFAKVSNENTRLAYGA
YVKPLKDDGSQSLGTTPYYVLDTTAQKYLGVMGVEDFTQSLTYPDSLLIPPPSEYGEV
NSGVMKANRPNYIGFRDNFINLLYHDTGVCSGTLNSERSGMNVVVELQDRNTELSYQY
MLADMMSRHHYFALWNQAVDQYDHDVRVFNNDGYEEGVPTYAFSPEGTGQGPISSANI
TLSGVKVYTNGQNDKGTEVTNLTTYLNAGAVPSYEIDLAASQRRNFIITNIADYLPDK
YKYSIAGFNPETDNVDPTTYAYMNRRVPLTNVVDSVTNIGP"

misc_feature 1..1296
/note="N-terminal domain; Region: Adeno_hexon; pfam01065"
/db_xref="CDD:110092"

ORIGIN

SEQ ID NO: 6

```
   1 accgagaagg cccagcggct tcagatcagg ttctatccca cccagacgga cgacaccccc
  61 aacagttacc gggttcggta cagcttaaac gtgggggaca gctgggtgtt ggacatggga
 121 gcgacctact tcgacatcaa aggggtgctc gacagaggtc cttccttcaa gccctacggc
 181 ggcacggctt acaaccccct ggcccctcgc gaagccttct taacaactg gatcgaggac
 241 gatggaaaca acacaaccat cacgggacaa atgaccaatc cgtacaagaa cgaggcgcaa
 301 aacacagcta cggcaacagc tgcagcaatc gccagcgttt caggctctta tcctaaccct
 361 aacgtggggc tggccattag cgaaatggga gccctcaccc cgacactagc agcacaggtc
 421 ggtctggccg tcggtttgc caaggtgtcg aatgagaaca cgcgcctggc ttatggagcg
 481 tatgtgaagc ctctaaaaga cgacggctct cagtcacttg gaacaacgcc ttactacgtg
 541 ttagacacca ccgcacagaa atacttgggc gtcatggggg tagaagactt tacgcaaagt
 601 cttacctacc cagacagtct gttaatcccc cctccttctg agtacggaga ggttaacagc
 661 gggtgatga aagcgaacag acccaactac atcgggttcc gtgacaattt catcaacctc
 721 ctgtaccacg ataccggcgt ctgctccggg accctcaact ccgaacgctc aggcatgaac
 781 gtggtggtgg aattgcagga ccgaaacacc gaactcagct accagtacat gctcgccgat
 841 atgatgtcca ggcatcacta tttcgctctc tggaaccagg ccgtggatca gtacgaccac
 901 gacgtgcgcg tgtttaacaa cgacggctac gaggagggcg tgcccacgta cgccttctcg
 961 cccgaggta caggacaggg tccatcagt tcggcaaata tcacgcttc tggtgtcaag
1021 gtgtacacta acggtcagaa cgacaagggc accgaagtca caatcttac aacgtacctc
1081 aatgccggc ccgtgccttc ctacgagatc gatctgcgcg cctcccagcg gcgtaatttt
1141 atcatcacca acatcgccga ctacctgccc gataagtaca agtacagcat tgccgggttc
1201 aacccgaaa ccgataacgt ggaccccacc acttacgcgt acatgaacag gagggtgccc
1261 ctgaccaacg tggtggattc tgttaccaac atcgggccag a
```

TABLE 6-continued

Hexon Loop Sequences of Isolates Used in Examples

FAdV-11
GenBank: EF685580.1
Fowl adenovirus D isolate 06-58730 hexon protein gene, partial cds
FeaturesSequence
LOCUS EF685580 820 bp DNA linear VRL 06 Aug. 2007
DEFINITION Fowl adenovirus D isolate 06-58730 hexon protein gene, partial cds.
ACCESSION EF685580
VERSION EF685580.1 GI:154362765
KEYWORDS.
SOURCE Fowl adenovirus D
ORGANISM Fowl adenovirus D
Viruses; dsDNA viruses, no RNA stage; *Adenoviridae*; *Aviadenovirus*.
REFERENCE 1 (bases 1 to 820)
AUTHORS Ojkic,D., Martin,E., Swinton,J., Vaillancourt,J.-P., Boulianne,M. and Gomis,S.
TITLE *Genotyping of Canadian isolates of Fowl adenoviruses*
JOURNAL Unpublished
REFERENCE 2 (bases 1 to 820)
AUTHORS Ojkic,D., Martin,E., Swinton,J., Vaillancourt,J.-P., Boulianne,M. and Gomis,S.
TITLE *Direct Submission*
JOURNAL Submitted (18 Jun. 2007) Animal Health Laboratory, University of Guelph, Box 3612, University of Guelph, Guelph, Ontario NIH 6R8, Canada FEATURES Location/Qualifiers
source 1..820
/organism="Fowl adenovirus D"
/mol_type="genomic DNA"
/isolate="06-58730"
/db_xref="taxon:190064"
/collection_date="2006"
CDS <1..>820
/note="loop 1"
/codon_start=1
/product="hexon protein"
/protein_id="ABS81210.1"
/db_xref="GI:154362766"

SEQ ID NO: 7

/translation="QRLQIRFYPTQTDDTPNSYRVRYSLNVGDSWVLDMGATYFDIKG
VLDRGPSFKPYGGTAYNPLAPREAFFNNWVDTEASKTVITGQMTTPYENVQGAKDKTA
AIVAALSGVYPDPNIGTAISEMGALDATSAAQVGLAARFAKVSSDNTRLAYGAYVKPL
KNDGSQSINPTPYWVMDSNATNYLGVMGVEDFSASLTYPDTLLIPPPTEYSEVNTGVM
KANRPNYIGFRDNFINLLYHDTGVCSGTLNSERSGMNVVVELQDRNTELSYQYML"

FAdV Sequences for U of SK.txt
misc_feature 1..>820
/note="N-terminal domain; Region: Adeno_hexon; pfam01065"
/db_xref="CDD:110092"

ORIGIN

SEQ ID NO: 8

```
  1 cagaggcttc agatcaggtt ttacccgacg cagaccgacg acacgcccaa cagttaccgc
 61 gtgcggtaca gtttaaacgt gggcgacagt tgggttcttg acatgggagc cacctacttc
121 gacatcaagg gcgtcctaga cagaggacct tcttttaaac cgtatggagg aaccgcatac
181 aatcccctcg cgccccgcga agccttttc aacaattggg ttgacacaga ggcgagcaag
241 accgtcatca cgggtcagat gacaactccc tacgaaaacg tccagggcgc taaagacaag
301 actgccgcga tcgtcgccgc tctttcaggg gtttatcccg atcccaatat cggtaccgcc
361 atcagcgaga tgggcgcctt agacgcgacg tcggcagcc aagtcggatt ggctgcccga
421 ttcgcgaaag tgtcgagcga taacacgcgt ctagcctacg gagcctacgt taaaccgctc
481 aagaacgacg gttctcaatc gattaacccc actccttact gggtcatgga cagcaacgcc
541 acaaactatc tcggagtcat gggagtcgaa gactttagcg cctcgctaac ctatcccgat
601 acgctcctca ttccccgcc gaccgaatac tcagaagtga ataccggcgt catgaaggca
661 aacaggccga attcatcgg atttagggac aatttttatca acctgctcta tcatgatacg
721 ggtgtgtgct cgggtactct gaattcggag cgttcgggta tgaacgtcgt cgtcgagctc
781 caggacagaa acacggaact cagttaccag tacatgttag
```

Esurient Strain (Australian Intervet Vaccine)
Sequence is listed in FIG. 14 identified as Esurient. SEQ ID NO: 9

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Full Citations for References Referred to in the Specification

Ahmad, M. U. D., and Burgess, G. W. (2001). Production and characterization of monoclonal antibodies to fowl adenoviruses. Avian Pathol. 30(5): 457-463

Alvarado, I. R., Villegas, P., El-Attrache, J., Jensen, E., Rosales, G., Perozo, F., and Purvis, L. B. (2007). Genetic Characterization, Pathogenicity, and Protection Studies with an Avian Adenovirus Isolate Associated with Inclusion Body Hepatitis. Avian Dis. 51(1): 27-32

Antillon, A., and Lucio, B. (1974). Inclusion body hepatitis in Mexico. Avian Dis. 19: 195-196

Aucouturier, J., Dupuis, L., and Ganne, V. (2001). Adjuvants designed for veterinary and human vaccines. Vaccine 19: 2666-1672

Babiuk, L. A., Gomis, S., and Hecker, R. (2003). Molecular approaches to disease cintrol. Poult. Sci. 82: 870-857

Barr, D. A., and Scott, P. (1988). Adenoviruses and IBH. Proc. Second Asian/Pacific Poult. Heal. Conf., Sydney, Australia, 323-326

Benko, M., Harrach, B., Both, G. W., Russell, W. C., Adair, B. M., Adam, E., de Jong, J. C., Hess, M., Johnson, M., Kajon, A., Kidd, A. H., Lehmkuhl, H. D., Li, Q. G., Mautner, V., Pring-Akerblom, P., and Wadell, G. (2005). Family Adenoviridae. In: Fauquet, C. M., Mayo, M. A., Maniloff, J., Desselberger, U., and Ball, L. A., Eds., Virus taxonomy. Eighth report of the International Committee on Taxonomy of Viruses. Elservier, New York, 213-228

Bickford, A. A. (1972). Inclusion body hepatitis of chickens. Proc. 21st West. Poult. Dis. Conf.

Calnek, B. W., and Cowen, B. S. (1975). Adenoviruses of chickens: Serologic groups. Avian Dis. 19: 91-103

Christensen, N. H., and Saifuddin, M. (1989). A primary epidemic of inclusion body hepatitis in broilers. Avian Dis. 33(4): 622-630

Comoy, E. E., Capron, A., and Thyphronitis, G. (1997). In vivo induction of type 1 and 2 immune responses against protein antigens. Int. Immunol. 9(4): 523-531

Cowen, B. S. (1992). Inclusion body hepatitis-anaemia and hydropericardium syndrome: aetiology and control. World's Poul. Sci. 48: 247-254

El-Attrache, J., and Villegas, P. (2001). Genomic identification and characterization of avian adenoviruses associated with inclusion body hepatitis. Avian Dis. 45(4): 780-787

Erny, K. M., Barr, D. A., and Fahey, K. J. (1991). Molecular characterization of highly virulent fowl adenoviruses associated with outbreaks of inclusion body hepatitis. Avian Pathol. 20(4): 597-606

Erny, K., Pallister, J., and Sheppard, M. (1995). Immunological and molecular comparison of fowl adenovirus serotypes 4 and 10. Arch. Virol. 140(3): 491-501

Fadly, A. M., and Winterfield, R. W. (1973). Isolation and some characteristics of an agent associated with inclusion body hepatitis, hemorrhages, and aplastic anemia in chickens. Avian Dis. 17(1): 182-93

Fadly, A. M., and Winterfield, R. W. (1975). Antigenic characterization of the inclusion body hepatitis virus. Am. J. Vet. Res. 36: 532-534

Glisson, J. R., and Klevan, S. H. (1993). Poultry vaccines. In: Peters, A. R., (Ed.), Vaccines and veterinary applications. Butterworth and Heinemann Ltd., Oxford, UK, 165-198

Gomis, S., Babiuk, L., Godson, D. L., Allan, B., Thrush, T., Townsend, H., Willson, P., Waters, E., Hecker, R., and Potter, A. (2003). Protection of chickens against *Escherichia coli* infections by DNA containing CpG motifs. Infect. Immun. 71(2): 857-863

Gomis, S., Babiuk, L., Allan, B., Willson, P., Waters, E., Hecker, R., and Potter, A. (2007). Protection of chickens against a lethal challenge of *Escherichia coli* by a vaccine containing CpG oligodeoxynucliotide as an adjuvant. Avian Dis. 51: 78-83

Gomis, S., Goodhope, R., Ojkic, D., and Willson, P. (2006). Inclusion body hepatitis as a primary disease in broilers in Saskatchewan, Canada. Avian Dis. 50(4): 550-555

Grimes, T. M. (1992). Cause and control of a peracute form of inclusion body hepatitis. Proc. 41st West. Poult. Dis. Conf., Sacramento, Calif., 42-44

Grimes, T. M. (2007). Inclusion body hepatitis of chickens-occurence and control. Proc. 56th West. Poult. Dis. Conf., March 27-29, Las Vegas, Nev., 42-46

Grimes, T. M., and King, D. J. (1977b). Serotyping avian adenoviruses by a microneutralization procedure. Am. J. Vet. Res. 38(3): 317-321

Grimes, T. M., Culver, D. H., and King, D. J. (1977a). Virus-neutralizing antibody titers against 8 avian adenovirus serotypes in breeder hens in Georgia by a microneutralization procedure. Avian Dis. 21(2): 220-9

Grimes, T. M., King, D. J., Kleven, S. H., and Fletcher, O. J. (1977b). Involvement of a type-8 avian adenovirus in the etiology of inclusion body hepatitis. Avian Dis. 21(1): 26-38

Grimes, T. M., King, D. J., Fletcher, O. J., and PAge, R. K. (1978b). Serologic and pathogenicity studies of avian adenovirus isolated from chickens with inclusion body hepatitis. Avian Dis. 22: 177-180

Hess, M., Prusas, C., and Monreal, G. (1998). Growth analysis of adenoviruses isolated from pigeons in chicken cells and serological characterization of the isolates. Avian Pathol. 27(2): 196-199

Hilgers, L. A., Nicolas, I., Lejeune, G., Dewil, E., and Boon, M. (1998). Effect of various adjuvants on secondary immune response in chickens. Vet. Immunol. Immunopathol. 66: 159-171

Hilgers, L. A. T., and Snippe, H. (1992). DDA as an immunological adjuvant. Res. Immunol. 143: 494-503

Hoffman, R., Wessling, E., Dorn, P., and Dangschat, H. (1975). Lesions in chickens with spontaneous or experimental infectious hepato-myelopoietic disease (inclusion body hepatitis) in Germany. Avian Dis. 19: 224-236

HogenEsch, H. (2002). Mechanisms of stimulation of the immune response by aluminium adjuvants. Vaccine 20(Suppl. 3): 34-39

Ioannou, X. P., Griebel, P., Hecker, R., Babiuk, L. A., and van Drunen Littel-van den Hurk, S. (2002b). The immunogenicity and protective efficacy of bovine herpesvirus 1 glycoprotein D plus Emulsigen are increased by formulation with CpG oligodeoxynucleotides. J. Virol. 76(18): 9002-9010

Itakura, C., Yasuba, M., and Goto, M. (1974b). Histopatholoical studies on inclusion body hepatitis in broiler chickens. Jap. J. Vet. Sci. 36: 329-340

Janeway C A Jr. (1992) The immune system evolved to discriminate infectious nonself from noninfectious self. Immunol. Today 13: 11-16.

Kawamura, H., Shimizu, F., and Tsubahara (1964). Avian adenoviruses: its properties and serological classification. Natl. Inst Ani. Heal. Q. (Tokyo) 4: 183-193

Kefford, B., and Borland, R. (1979). Isolation of a serotype 8 avian adenovirus associated with inclusion body hepatitis Aust. Vet. J. 55(12): 599

Khanna, P. N. (1964). Studies on cytopathogenic avian enteroviruses. 1. Their isolation and serological classification. Avian Dis. 8: 632-637

Klinman, D. M., Grusel, I., and Verthelti, D. (2004). Use of CpG oligodeoxynucliotides as immune adjuvants. Immunol. Rev. 199: 201-216

Linghua, Z., Xingshan, T., and Fengzhen, Z. (2006). The efficacy of CpG oligodeoxynucliotides, in combination with conventional adjuvants, as immunological adjuvants to swine streptococci septicemia vaccine in pigs in vivo. Int. Immunopharmcol. 6: 1267-1276

Mazaheri, A., Prusas, C., Voβ, M., and Hess, M. (1998). Some strains of serotype 4 fowl adenoviruses cause inclusion body hepatitis and hydropericardium syndrome in chickens. Avian Pathol. 27(3): 269-276

Mendelson, C., Nothelfer, H. B., and Monreal, G. (1995). Identification and characterization of an avian adenovirus isolated from a 'spiking mortality syndrome' field outbreak in broilers on the Delmarva Peninsula, USA. Avian Pathol. 24(4): 693-706

Meulemans, G., Boschmans, M., van den Berg, T. P., and Decaesstecker, M. (2001). Polymerase chain reaction combined with restriction enzyme analysis for detection and differentiation of fowl adenoviruses. Avian Pathol. 30(6): 655-660

Meulemans, G., Couvreur, B., Decaesstecker, M., Boschmans, M., and Berg, T. P. (2004). Phylogenetic analysis of fowl adenoviruses. Avian Pathol. 33(2): 164-170

McFerran, J. B. (1997). Adenovirus infections. In: Calnek, B. W., Barnes, H. J., Reid, W. M., and Yoder, J., H. W., Eds., Diseases of Poultry Vol. 10. Iowa State University Press, Ames, Iowa, 608-620

McFerran, J. B., and Adair, B. M. C. (1977). Avian adenoviruses: a review. Avian Pathol. 6(3): 189-217

McFerran, J. B., Clarke, J. K., and Connor, T. J. (1972). Serological classification of avian adenoviruses. Arch. Virol. 39(1): 132-139

McFerran, J. B., McCracken, R. M., Connor, T. J., and Evans, R. T. (1976b). Isolation of viruses from clinical outbreaks of inclusion body hepatitis. Avian Pathol. 5(4): 315-324

Monreal, G. (1992). Adenovirus and adeno-associated viruses of poultry. Poul. Sci. Rev. 4(1): 1-27

Mutwiri, G. K., Nichani, A. K., Babiuk, S., and Babiuk, L. A. (2004). Stratagies for enhancing immunostimulatory effects of CpG oligodeoxynucleotides. J. Control Release 97: 1-17

Norrby, E., and Wadell, G. (1969). Immunological relationships between hexons of certain human adenoviruses. J. Virol. 4: 663-670

Ojkic, D., Binnington, B., and Martin, E. (2005). Phylogenetic analysis of fowl adenoviruses isolated from chicken with inclusion body hepatitis in Canada. 77th Northeastern Conf. Avian Dis., Ithaca, N.Y., 19

Ojkic, D., Krell, P. J., Tuboly, T., and Nagy, É. (2008a). Characterization of fowl adenoviruses isolated in Ontario and Quebec, Canada. Can. J. Vet. Res. 72(3): 236-241

Ojkic, D., Martin, E., Swinton, J., Vaillancourt, J. P., Boulianne, M., and Gomis, S. (2008b). Genotyping of Canadian isolates of fowl adenoviruses. Avian Pathol. 37(1): 95-100

Otsuki, K., Tsubokura, M., Yamamoto, H., Imamura, M., Sakagami, Y., Saio, H., and Hosokawa, D. (1976). Some properties of avian adenoviruses isolated from chickens with inclusion body hepatitis in Japan. Avian Dis. 20(4): 693-705

Pallister, J. A., and Sheppard, M. (1996). Comparison by restriction enzyme analysis of three fowl adenoviruses of varying pathogenicity. Vet. Micro. 48: 155-163

Pallister, J., Wright, P. J., and Sheppard, M. (1996). A single gene encoding the fiber is responsible for variations in virulence in the fowl adenoviruses. J. Virol. 70(8): 5115-5122

Philippe, C., Grgic, H., and Nagy, É. (2005). Inclusion body hepatitis in young broiler breeders associated with a serotype 2 adenovirus in Ontario, Canada. J. App. Poult. Res. 14(3): 588-593

Reece, R. L., Barr, D. A., Grix, D. C., Forsyth, W. M., Condron, R. J., and Huindmarsh, M. (1986a). Observations on naturally occurring inclusion body hepatitis in Victorian chickens. Aust. Vet. J. 63(6): 201-202

Rijke, E. O., Loeffen, A. H. C., and Lutticken, D. (1998). The use of lipid amines as immunopotentiators for viral vaccines. In: Bizzini, B., and Bonmassar, E., Eds., Advances in immunomodulation. Pythagota Press, Rome-Milan, 433-443

Roh, H. J., Sung, H. W., and Kwon, H. M. (2006). Effects of DDA, CpG-ODN, and plasmid-encoded chicken IFN-on protective immunity by a DNA vaccine against IBDV in chickens. J. Vet. Sci. 7(4): 361-368

Rosenberger, J. K., Eckroade, R. J., Klopp, S., and Krauss, W. C. (1974). Characterisation of several viruses isolated from chickens with inclusion body hepatitis and aplastic anaemia. Avian Dis. 18: 399-409

Saifuddin, M., Wilks, C. R., and Murray, A. (1992). Characterisation of avian adenoviruses associated with inclusion body hepatitis. N. Z. Vet. J. 40: 52-55

Sarfati, D. (1991). Inclusion body hepatitis in Mexico: epidemiological survey. Proc. 41st West. Poult. Dis. Conf., Acapulco, Mexico, 250

Schijns, V. E. J. C. (2006). Perspective on immunological mechanisms underlying adjuvant activity. Unraveling "the immunologist's dirty secrete". In: Schijns, V. E. J. C., and O'Hagon, D. T., Eds., Immunopotentiation in morden vaccines. Elsevier Academic Press, Amsterdam, 1-16

Schijns, V. E. J. C., Sharma, J., and Tarpey, I. (2008). Practical aspects of poultry vaccination. In: Davison, F., Kaspers, B., and Schat, K. A., Eds., Avian immunology, 1st edn. Elsevier, Amsterdam, 373-393

Singh, A., Oberoi, M. S., Jand, S. K., and Singh, A. B. (1996). Epidemiology of inclusion body hepatitis in poultry in Northern India from 1990 to 1994. Rev. Sci. Tech. Off. Int. Epi. 15(3): 1053-1060

Steer, P. A., Kirkpatrick, N. C., O'Rourke, D., and Noionohammadi, A. H. (2009). Classification of fowl adenovirus serotypes by use of high-resolution melting-curve analysis of the hexon gene region. J. Clin. Micro. 47(2): 311-321

Stone, H. D. (1997). Newcastle disease oil emusion vaccines prepared with animal, vegetable, and synthetic oils. Avian Dis. 41: 591-597

Toogood, C. I., Crompton, J., and Hay, R. T. (1992). Antipeptide antisera define neutralizing epitopes on the adenovirus hexon. J. Gen. Virol. 73(6): 1429-1435

Toro, H., Gonzalez, C., Cerda, L., Morales, M. A., Dooner, P., and Salamero, M. (2001a). Prevention of inclusion body hepatitis/hydropericardium syndrome in progeny chickens by vaccination of breeders with fowl adenovirus and chicken anemia virus. Avian Dis. 46: 547-554

Toro, H., Prusas, C., Raue, R., Cerda, L., Geisse, C., Gonzalez, C., and Hess, M. (1999). Characterization of fowl adenoviruses from outbreaks inclusion body hepatitis/hydromericardium syndrome in chile. Avian Dis. 43: 262-270

Wells, R. J., and Harrigan, K. (1974). A fatal adenovirus infection of broiler chickens: inclusion body hepatitis. Vet. Rec. 94(21): 481-2

Wells, R. J. H., Westbury, H. A., Harrigan, K. E., Coleman, G. D. C., and Beilharz, R. G. (1977). Epidemic adenovirus inclusions body hepatitis of the chicken in Australia. Aust. Vet. J. 53(12): 586-590

Willson, P. J., Rossi-Campos, A., and Potter, A. A. (1995). Tissue reaction and immunity in swine immunized with *Actinobacillus pleuropneumoniae*. Can. J. Vet. Res. 59: 299-305

Winterfield, R. W., Fadly, A. M., and Hoerr, F. J. (1977). Immunization of chickens against adenovirus infection. Poul. Sci. 56(5): 1481-6

Young, J. A., Purcell, D. A., and Kavanagh, P. J. (1972). Inclusion body hepatitis outbreak in broiler flocks. Vet. Rec. 90: 72

SEQUENCE LISTING

```
<160> NUMBER OF SEQ ID NOS: 23

<210> SEQ ID NO 1
<211> LENGTH: 415
<212> TYPE: PRT
<213> ORGANISM: fowl adenovirus
<220> FEATURE:
<221> NAME/KEY: MISC_FEATURE
<223> OTHER INFORMATION: FAdV-7

<400> SEQUENCE: 1

Thr Glu Lys Ala Gln Arg Leu Gln Ile Arg Phe Tyr Pro Thr Gln Thr
1               5                   10                  15

Asp Asp Thr Pro Asn Ser Tyr Arg Val Arg Tyr Ser Leu Asn Val Gly
                20                  25                  30

Asp Ser Trp Val Leu Asp Met Gly Ala Thr Tyr Phe Asp Ile Lys Gly
            35                  40                  45

Val Leu Asp Arg Gly Pro Ser Phe Lys Pro Tyr Gly Gly Thr Ala Tyr
        50                  55                  60

Asn Pro Leu Ala Pro Arg Glu Ala Phe Phe Asn Asn Trp Ile Glu Asp
65                  70                  75                  80

Glu Asp Asn Asn Thr Ser Ile Thr Gly Gln Met Thr Asn Pro Tyr Thr
                85                  90                  95

Asn Glu Gln Gln Asn Thr Ala Thr Ala Thr Ala Gly Ala Ile Ala Ser
            100                 105                 110

Val Ser Gly Ser Tyr Pro Asn Pro Asn Val Gly Leu Ala Ile Ser Glu
        115                 120                 125

Met Gly Ala Leu Thr Pro Thr Leu Ala Ala Gln Val Gly Leu Ala Gly
    130                 135                 140

Arg Phe Ala Lys Val Ser Ser Glu Asn Thr Arg Leu Ala Tyr Gly Ala
145                 150                 155                 160

Tyr Val Lys Pro Ile Lys Asp Asp Gly Ser Gln Ser Leu Gly Thr Thr
                165                 170                 175

Pro Tyr Tyr Val Leu Asp Thr Thr Ala Gln Lys Tyr Leu Gly Val Met
            180                 185                 190

Gly Val Glu Asp Phe Thr Gln Ser Leu Thr Tyr Pro Asp Ser Leu Leu
        195                 200                 205

Ile Pro Pro Pro Ser Glu Tyr Arg Ala Val Asn Ser Gly Val Met Lys
    210                 215                 220

Ala Asn Arg Pro Asn Tyr Ile Gly Phe Arg Asp Asn Phe Ile Asn Leu
225                 230                 235                 240

Leu Tyr His Asp Thr Gly Val Cys Ser Gly Thr Leu Asn Ser Glu Arg
```

|       |       |       |       | 245   |       |       |       |       | 250   |       |       |       |       | 255   |       |
|-------|-------|-------|-------|-------|-------|-------|-------|-------|-------|-------|-------|-------|-------|-------|-------|
| Ser   | Gly   | Met   | Asn   | Val   | Val   | Glu   | Leu   | Gln   | Asp   | Arg   | Asn   | Thr   | Glu   | Leu   |       |
|       |       |       |       | 260   |       |       |       |       | 265   |       |       |       |       | 270   |       |
| Ser   | Tyr   | Gln   | Tyr   | Met   | Leu   | Ala   | Asp   | Met   | Met   | Ser   | Arg   | His   | His   | Tyr   | Phe   |
|       |       |       | 275   |       |       |       |       | 280   |       |       |       |       | 285   |       |       |
| Ala   | Leu   | Trp   | Asn   | Gln   | Ala   | Val   | Asp   | Gln   | Tyr   | Asp   | His   | Asp   | Val   | Arg   | Val   |
|       |       |       | 290   |       |       |       |       | 295   |       |       |       |       | 300   |       |       |
| Phe   | Asn   | Asn   | Asp   | Gly   | Tyr   | Glu   | Glu   | Gly   | Val   | Pro   | Thr   | Tyr   | Ala   | Phe   | Ser   |
| 305   |       |       |       |       | 310   |       |       |       |       | 315   |       |       |       |       | 320   |
| Pro   | Glu   | Gly   | Thr   | Gly   | Gln   | Gly   | Pro   | Ile   | Ser   | Ser   | Ala   | Asn   | Ile   | Thr   | Leu   |
|       |       |       |       | 325   |       |       |       |       | 330   |       |       |       |       | 335   |       |
| Ser   | Gly   | Val   | Lys   | Val   | Tyr   | Thr   | Asn   | Gly   | Gln   | Asn   | Asp   | Lys   | Gly   | Thr   | Glu   |
|       |       |       |       | 340   |       |       |       |       | 345   |       |       |       |       | 350   |       |
| Val   | Ala   | Asn   | Thr   | Thr   | Thr   | Tyr   | Leu   | Asn   | Ala   | Gly   | Thr   | Val   | Pro   | Ser   | Tyr   |
|       |       |       | 355   |       |       |       |       | 360   |       |       |       |       | 365   |       |       |
| Glu   | Ile   | Asp   | Leu   | Ala   | Ala   | Ser   | Gln   | Arg   | Arg   | Asn   | Phe   | Ile   | Ile   | Thr   | Asn   |
|       |       | 370   |       |       |       |       | 375   |       |       |       |       | 380   |       |       |       |
| Ile   | Ala   | Asp   | Tyr   | Leu   | Pro   | Asp   | Lys   | Tyr   | Lys   | Tyr   | Asn   | Ile   | Ser   | Gly   | Phe   |
| 385   |       |       |       |       | 390   |       |       |       |       | 395   |       |       |       |       | 400   |
| Asn   | Pro   | Glu   | Thr   | Asp   | Asn   | Val   | Asp   | Pro   | Thr   | Thr   | Tyr   | Ala   | Tyr   | Met   |       |
|       |       |       |       | 405   |       |       |       |       | 410   |       |       |       |       | 415   |       |

<210> SEQ ID NO 2
<211> LENGTH: 1247
<212> TYPE: DNA
<213> ORGANISM: fowl adenovirus
<220> FEATURE:
<221> NAME/KEY: misc_feature
<223> OTHER INFORMATION: FAdV-7

<400> SEQUENCE: 2

```
accgagaagg cccagcggct tcagatcagg ttctatccca cccagacgga cgacaccccc      60
aacagttacc gggttcggta cagcttaaac gtggggacga gctgggtgtt ggacatggga     120
gcgacctact tcgacatcaa aggggtgctc gacagaggtc cttccttcaa gcccttacggc    180
ggcacggctt acaacccect ggcccctcgc gaagccttct ttaacaactg gatcgaggac     240
gaagacaaca atacatccat cacggggcaa atgaccaatc cgtacacgaa cgagcagcaa     300
aacacagcta cggcaacagc tggggcaatc gccagcgttt caggctctta tcctaaccct     360
aacgtggggc tggccattag cgaaatggga gccctcaccc cgacactagc agcacaggtc     420
ggcctggccg gacgctttgc caaggtgtcg agcgagaaca cgcgcctggc ttatggagcg     480
tatgtgaagc ctataaaaga cgacggctct cagtcacttg aacaacgcc ttactacgtg      540
ttagacacca ccgcacagaa atacttgggc gtcatggggg tagaagactt tacacaaagt     600
cttacctacc cagacagtct gttaatcccc cctccttctg agtacagagc ggttaacagc     660
ggggtgatga aagccaacag acccaactac atcgggttcc gtgacaattt catcaacctc     720
ctataccacg ataccggcgt gtgctccggg accctcaact ccgaacggtc aggcatgaac     780
gtggtggtgg aattgcagga ccgaaatacc gaactcagtt accagtacat gctcgccgat     840
atgatgtcca ggcatcacta tttcgctctc tggaaccagg ccgtggatca gtacgaccac     900
gacgtgcgcg tgtttaacaa cgacggctac gaggagggcg tccccacgta cgccttctcg     960
cccgagggta caggacaggg acccatcagt tcagcaaata tcacgctttc tggtgtcaag    1020
gtgtacacta cggacagaaa cgacaagggc accgaagtcg caaacactac gacgtatctc    1080
aatgccggca ccgttcctte ctacgagatc gatctggcgg cctctcaacg gcgaaacttt    1140
```
atcatcacca atatcgccga ctacctgccc gataagtaca agtacaacat ttccgggttc     1200
aaccccgaaa ccgataacgt agaccccacg acttacgcgt acatgaa                  1247

<210> SEQ ID NO 3
<211> LENGTH: 286
<212> TYPE: PRT
<213> ORGANISM: fowl adenovirus
<220> FEATURE:
<221> NAME/KEY: MISC_FEATURE
<223> OTHER INFORMATION: FAdV-8a

<400> SEQUENCE: 3

Pro Thr Arg Asn Val Thr Thr Glu Lys Ala Gln Arg Leu Gln Ile Arg
1               5                   10                  15

Phe Tyr Pro Thr Gln Thr Asp Asp Thr Pro Asn Ser Tyr Arg Val Arg
            20                  25                  30

Tyr Ser Leu Asn Val Gly Asp Ser Trp Val Leu Asp Met Gly Ala Thr
        35                  40                  45

Tyr Phe Asp Ile Lys Gly Val Leu Asp Arg Gly Pro Ser Phe Lys Pro
    50                  55                  60

Tyr Gly Gly Thr Ala Tyr Asn Pro Leu Ala Pro Arg Glu Ala Phe Phe
65                  70                  75                  80

Asn Asn Trp Ile Ala Glu Asp Gly Asn Lys Thr Thr Ile Thr Gly Gln
                85                  90                  95

Met Ser Asn Pro Tyr Glu Asn Thr Thr Gln Thr Ala Ala Ala Glu Thr
            100                 105                 110

Ala Ala Val Val Ala Ser Val Ser Gly Ser Tyr Pro Asn Pro Asn Ser
        115                 120                 125

Gly Pro Gly Ile Ser Glu Met Gly Ala Leu Ser Thr Thr Leu Ala Ala
    130                 135                 140

Gln Val Gly Leu Ala Gly Arg Phe Ala Lys Val Ser Ser Glu Asn Thr
145                 150                 155                 160

Arg Leu Ala Tyr Gly Ala Tyr Val Lys Pro Leu Lys Asn Asp Gly Ser
                165                 170                 175

Gln Ser Leu Val Gln Thr Pro Tyr Tyr Val Met Asp Ser Gly Ser Thr
            180                 185                 190

Lys Tyr Leu Gly Val Met Gly Val Glu Asp Phe Thr Asp Ser Leu Thr
        195                 200                 205

Tyr Pro Asp Ser Leu Leu Ile Pro Pro Ile Glu Tyr Gly Thr Val
    210                 215                 220

Asn Thr Gly Val Met Lys Ala Asn Arg Pro Asn Tyr Ile Gly Phe Arg
225                 230                 235                 240

Asp Asn Phe Ile Asn Leu Leu Tyr His Asp Thr Gly Val Cys Ser Gly
                245                 250                 255

Thr Leu Asn Ser Glu Arg Ser Gly Met Asn Val Val Val Glu Leu Gln
            260                 265                 270

Asp Arg Asn Thr Glu Leu Ser Tyr Gln Tyr Met Leu Ala Asp
        275                 280                 285

<210> SEQ ID NO 4
<211> LENGTH: 860
<212> TYPE: DNA
<213> ORGANISM: fowl adenovirus
<220> FEATURE:
<221> NAME/KEY: misc_feature
<223> OTHER INFORMATION: FAdV-8a

<400> SEQUENCE: 4

-continued

```
cctacccgca atgtcactac cgagaaggcc cagcggcttc agatcaggtt ctaccccacc    60
cagacggacg acaccccca cagctaccgg gttcggtaca gcctaaacgt ggggacagc    120 tgggtgttgg acatgggagc gacctacttc gacatcaaag gggtgctcga cagaggtcct    180
tccttcaagc cctacggcgg cacggcttac aacccctgg cccctcgcga agccttcttt    240
aacaactgga tcgcggaaga cggcaacaag acaaccatca ccgggcaaat gtctaacccc    300
tatgagaata ccactcaaac ggccgcagcg gaaacagccg ccgtcgtcgc cagcgtctcc    360
ggcagctacc ctaatcccaa ctcgggtccg gcattagcg aaatgggggc gctcagcact    420
acgctagcgg ctcaggtcgg tctagccggt cgcttcgcga agtatccag cgagaacacg    480 cgtctggctt acggggcgta cgtcaagccc ctgaagaacg acggctctca gtctctggtg    540
caaacacctt actacgtcat ggacagcggg agcacgaaat atttgggtgt gatgggggta    600
gaggacttta ccgatagcct gacctacccc gacagtctac tgatcccgcc tcctatcgag    660 tacgaacgg tcaataccgg ggtgatgaaa gctaacagac ccaattacat cgggttccgt    720
gacaatttca tcaacctcct gtaccacgat accggcgtgt gctccggcac cctgaactcc    780
gagcggtccg gcatgaacgt ggtcgtagaa ctgcaggacc gaaacaccga actcagttac    840
cagtacatgc tcgccgacat                                                860
```

<210> SEQ ID NO 5
<211> LENGTH: 433
<212> TYPE: PRT
<213> ORGANISM: fowl adenovirus
<220> FEATURE:
<221> NAME/KEY: MISC_FEATURE
<223> OTHER INFORMATION: FAdV-8a/8b

<400> SEQUENCE: 5

```
Thr Glu Lys Ala Gln Arg Leu Gln Ile Arg Phe Tyr Pro Thr Gln Thr
1               5                   10                  15

Asp Asp Thr Pro Asn Ser Tyr Arg Val Arg Tyr Ser Leu Asn Val Gly
            20                  25                  30

Asp Ser Trp Val Leu Asp Met Gly Ala Thr Tyr Phe Asp Ile Lys Gly
        35                  40                  45

Val Leu Asp Arg Gly Pro Ser Phe Lys Pro Tyr Gly Gly Thr Ala Tyr
    50                  55                  60

Asn Pro Leu Ala Pro Arg Glu Ala Phe Phe Asn Asn Trp Ile Glu Asp
65                  70                  75                  80

Asp Gly Asn Asn Thr Thr Ile Thr Gly Gln Met Thr Asn Pro Tyr Lys
                85                  90                  95

Asn Glu Ala Gln Asn Thr Ala Thr Ala Thr Ala Ala Ile Ala Ser
            100                 105                 110

Val Ser Gly Ser Tyr Pro Asn Pro Asn Val Gly Leu Ala Ile Ser Glu
        115                 120                 125

Met Gly Ala Leu Thr Pro Thr Leu Ala Ala Gln Val Gly Leu Ala Gly
    130                 135                 140

Arg Phe Ala Lys Val Ser Asn Glu Asn Thr Arg Leu Ala Tyr Gly Ala
145                 150                 155                 160

Tyr Val Lys Pro Leu Lys Asp Asp Gly Ser Gln Ser Leu Gly Thr Thr
                165                 170                 175

Pro Tyr Tyr Val Leu Asp Thr Thr Ala Gln Lys Tyr Leu Gly Val Met
            180                 185                 190

Gly Val Glu Asp Phe Thr Gln Ser Leu Thr Tyr Pro Asp Ser Leu Leu
        195                 200                 205
```

```
Ile Pro Pro Pro Ser Glu Tyr Gly Glu Val Asn Ser Gly Val Met Lys
    210                 215                 220
Ala Asn Arg Pro Asn Tyr Ile Gly Phe Arg Asp Asn Phe Ile Asn Leu
225                 230                 235                 240
Leu Tyr His Asp Thr Gly Val Cys Ser Gly Thr Leu Asn Ser Glu Arg
            245                 250                 255
Ser Gly Met Asn Val Val Glu Leu Gln Asp Arg Asn Thr Glu Leu
        260                 265                 270
Ser Tyr Gln Tyr Met Leu Ala Asp Met Met Ser Arg His His Tyr Phe
    275                 280                 285
Ala Leu Trp Asn Gln Ala Val Asp Gln Tyr Asp His Asp Val Arg Val
290                 295                 300
Phe Asn Asn Asp Gly Tyr Glu Glu Gly Val Pro Thr Tyr Ala Phe Ser
305                 310                 315                 320
Pro Glu Gly Thr Gly Gln Gly Pro Ile Ser Ser Ala Asn Ile Thr Leu
            325                 330                 335
Ser Gly Val Lys Val Tyr Thr Asn Gly Gln Asn Asp Lys Gly Thr Glu
        340                 345                 350
Val Thr Asn Leu Thr Thr Tyr Leu Asn Ala Gly Ala Val Pro Ser Tyr
    355                 360                 365
Glu Ile Asp Leu Ala Ala Ser Gln Arg Arg Asn Phe Ile Ile Thr Asn
370                 375                 380
Ile Ala Asp Tyr Leu Pro Asp Lys Tyr Lys Tyr Ser Ile Ala Gly Phe
385                 390                 395                 400
Asn Pro Glu Thr Asp Asn Val Asp Pro Thr Thr Tyr Ala Tyr Met Asn
            405                 410                 415
Arg Arg Val Pro Leu Thr Asn Val Val Asp Ser Val Thr Asn Ile Gly
        420                 425                 430
Pro
```

<210> SEQ ID NO 6
<211> LENGTH: 1301
<212> TYPE: DNA
<213> ORGANISM: fowl adenovirus
<220> FEATURE:
<221> NAME/KEY: misc_feature
<223> OTHER INFORMATION: FAdV-8a/8b

<400> SEQUENCE: 6

```
accgagaagg cccagcggct tcagatcagg ttctatccca cccagacgga cgacaccccc      60
aacagttacc gggttcggta cagcttaaac gtggggggaca gctgggtgtt ggacatggga     120
gcgacctact tcgacatcaa agggtgctc gacagaggtc cttccttcaa gccctacggc      180
ggcacggctt acaaccccct ggcccctcgc gaagccttct ttaacaactg gatcgaggac     240
gatggaaaca cacaaccat cacgggacaa atgaccaatc cgtacaagaa cgaggcgcaa      300
aacacagcta cggcaacagc tgcagcaatc gccagcgttt caggctctta tcctaaccct     360
aacgtggggc tggccattag cgaaatggga gccctcaccc cgacactagc agcacaggtc     420
ggtctggccg gtcggtttgc caaggtgtcg aatgagaaca cgcgcctggc ttatggagcg     480
tatgtgaagc tctaaaaga cgacggctct cagtcacttg aacaacgcc ttactacgtg       540
ttagacacca ccgcacagaa atacttgggc gtcatggggg tagaagactt tacgcaaagt     600
cttacctacc cagacagtct gttaatcccc cctccttctg agtacggaga ggttaacagc     660
ggggtgatga agcgaacag acccaactac atcgggttcc gtgacaattt catcaacctc     720
```

```
ctgtaccacg ataccggcgt ctgctccggg accctcaact ccgaacgctc aggcatgaac       780
gtggtggtgg aattgcagga ccgaaacacc gaactcagct accagtacat gctcgccgat       840
atgatgtcca ggcatcacta tttcgctctc tggaaccagg ccgtggatca gtacgaccac       900
gacgtgcgcg tgtttaacaa cgacggctac gaggagggcg tgcccacgta cgccttctcg       960 cccgaggta caggacaggg tcccatcagt tcggcaaata tcacgctttc tggtgtcaag      1020
gtgtacacta acgtcagaa cgacaagggc accgaagtca caaatcttac aacgtacctc      1080
aatgccggcg ccgtgccttc ctacgagatc gatctggcgg cctcccagcg gcgtaatttt      1140
atcatcacca acatcgccga ctacctgccc gataagtaca agtacagcat tgccgggttc      1200
aaccccgaaa ccgataacgt ggaccccacc acttacgcgt acatgaacag gagggtgccc      1260
ctgaccaacg tggtggattc tgttaccaac atcgggccag a                         1301
```

<210> SEQ ID NO 7
<211> LENGTH: 273
<212> TYPE: PRT
<213> ORGANISM: fowl adenovirus
<220> FEATURE:
<221> NAME/KEY: MISC_FEATURE
<223> OTHER INFORMATION: FAdV-11

<400> SEQUENCE: 7

```
Gln Arg Leu Gln Ile Arg Phe Tyr Pro Thr Gln Thr Asp Asp Thr Pro
1               5                   10                  15

Asn Ser Tyr Arg Val Arg Tyr Ser Leu Asn Val Gly Asp Ser Trp Val
            20                  25                  30

Leu Asp Met Gly Ala Thr Tyr Phe Asp Ile Lys Gly Val Leu Asp Arg
        35                  40                  45

Gly Pro Ser Phe Lys Pro Tyr Gly Gly Thr Ala Tyr Asn Pro Leu Ala
    50                  55                  60

Pro Arg Glu Ala Phe Phe Asn Asn Trp Val Asp Thr Glu Ala Ser Lys
65                  70                  75                  80

Thr Val Ile Thr Gly Gln Met Thr Thr Pro Tyr Glu Asn Val Gln Gly
                85                  90                  95

Ala Lys Asp Lys Thr Ala Ala Ile Val Ala Ala Leu Ser Gly Val Tyr
            100                 105                 110

Pro Asp Pro Asn Ile Gly Thr Ala Ile Ser Glu Met Gly Ala Leu Asp
        115                 120                 125

Ala Thr Ser Ala Ala Gln Val Gly Leu Ala Ala Arg Phe Ala Lys Val
    130                 135                 140

Ser Ser Asp Asn Thr Arg Leu Ala Tyr Gly Ala Tyr Val Lys Pro Leu
145                 150                 155                 160

Lys Asn Asp Gly Ser Gln Ser Ile Asn Pro Thr Pro Tyr Trp Val Met
                165                 170                 175

Asp Ser Asn Ala Thr Asn Tyr Leu Gly Val Met Gly Val Glu Asp Phe
            180                 185                 190

Ser Ala Ser Leu Thr Tyr Pro Asp Thr Leu Leu Ile Pro Pro Thr
        195                 200                 205

Glu Tyr Ser Glu Val Asn Thr Gly Val Met Lys Ala Asn Arg Pro Asn
    210                 215                 220

Tyr Ile Gly Phe Arg Asp Asn Phe Ile Asn Leu Leu Tyr His Asp Thr
225                 230                 235                 240

Gly Val Cys Ser Gly Thr Leu Asn Ser Glu Arg Ser Gly Met Asn Val
                245                 250                 255

Val Val Glu Leu Gln Asp Arg Asn Thr Glu Leu Ser Tyr Gln Tyr Met
```

Leu

<210> SEQ ID NO 8
<211> LENGTH: 820
<212> TYPE: DNA
<213> ORGANISM: fowl adenovirus
<220> FEATURE:
<221> NAME/KEY: misc_feature
<223> OTHER INFORMATION: FAdV-11

<400> SEQUENCE: 8

| | | | | | |
|---|---|---|---|---|---|
| cagaggcttc | agatcaggtt | ttacccgacg | cagaccgacg | acacgcccaa | cagttaccgc | 60 |
| gtgcggtaca | gtttaaacgt | gggcgacagt | tgggttcttg | acatgggagc | cacctacttc | 120 |
| gacatcaagg | gcgtcctaga | cagaggacct | tcttttaaac | cgtatggagg | aaccgcatac | 180 |
| aatcccctcg | cgccccgcga | agccttttc | aacaattggg | ttgacacaga | ggcgagcaag | 240 |
| accgtcatca | cgggtcagat | gacaactccc | tacgaaaacg | tccagggcgc | taaagacaag | 300 |
| actgccgcga | tcgtcgccgc | tctttcaggg | gtttatcccg | atcccaatat | cggtaccgcc | 360 |
| atcagcgaga | tgggcgcctt | agacgcgacg | tcggcagccc | aagtcggatt | ggctgcccga | 420 |
| ttcgcgaaag | tgtcgagcga | taacacgcgt | ctagcctacg | agcctacgt | taaaccgctc | 480 |
| aagaacgacg | gttctcaatc | gattaacccc | actccttact | gggtcatgga | cagcaacgcc | 540 |
| acaaactatc | tcggagtcat | gggagtcgaa | gactttagcg | cctcgctaac | ctatcccgat | 600 |
| acgctcctca | ttccccgcc | gaccgaatac | tcagaagtga | ataccggcgt | catgaaggca | 660 |
| aacaggccga | attcatcgg | atttagggac | aattttatca | acctgctcta | tcatgatacg | 720 |
| ggtgtgtgct | cgggtactct | gaattcggag | cgttcgggta | tgaacgtcgt | cgtcgagctc | 780 |
| caggacagaa | acacggaact | cagttaccag | tacatgttag | | | 820 |

<210> SEQ ID NO 9
<211> LENGTH: 800
<212> TYPE: DNA
<213> ORGANISM: fowl adenovirus
<220> FEATURE:
<221> NAME/KEY: misc_feature
<223> OTHER INFORMATION: FAdV08a, Esurient

<400> SEQUENCE: 9

| | | | | | |
|---|---|---|---|---|---|
| gcccagcggc | ttcagatcag | gttctatccc | acccagacgg | acgacaccc | caacagttac | 60 |
| cgggttcggt | acagcttaaa | cgtggggac | agctgggtgt | tggacatggg | agcgacctac | 120 |
| ttcgacatca | aggggtgct | cgacagaggt | ccttccttca | agccctacgg | cggcacggct | 180 |
| tacaaccccc | tggcccctcg | cgaagccttc | tttaacaact | ggatcgagga | tgatgaaaac | 240 |
| aacacaacca | tcacgggaca | aatgaccaat | ccgtacaaga | acgaggcgca | aaacacagct | 300 |
| acggcaacag | ctgcagcaat | cgccagcgtt | tcaggctctt | atcctaaccc | taacgtgggg | 360 |
| ctggccatta | gcgaaatggg | agccctcacc | ccgacactag | cagcacaggt | cggtctggcc | 420 |
| ggtcggtttg | ccaaggtgtc | gagtgagaac | acgcgcctgg | cttatggagc | gtatgtgaag | 480 |
| cctctaaaag | acgacggctc | tcagtcactt | ggaacaacgc | cttactacgt | gttagacacc | 540 |
| accgcacaga | aatacttggg | cgtcatgggg | gtagaagact | ttacgcaaag | tcttacctac | 600 |
| ccagacagtc | tgttaatccc | cctccttct | gagtacggag | cggttaacag | cggggtgatg | 660 |
| aaagcgaaca | gacccaacta | catcgggttc | cgtgacaatt | tcatcaacct | cctgtaccac | 720 |
| gataccggcg | tgtgctccgg | gaccctcaac | tccgaacggt | caggcatgaa | cgtggtggtg | 780 | gaattgcagg accgaaacac											800

<210> SEQ ID NO 10
<211> LENGTH: 300
<212> TYPE: PRT
<213> ORGANISM: fowl adenovirus
<220> FEATURE:
<221> NAME/KEY: MISC_FEATURE
<223> OTHER INFORMATION: FAdV08a_58

<400> SEQUENCE: 10

```
Lys Phe Arg Gln Thr Val Val Ala Pro Thr Arg Asn Val Thr Thr Glu
1               5                   10                  15

Lys Ala Gln Arg Leu Gln Ile Arg Phe Tyr Pro Thr Gln Thr Asp Asp
            20                  25                  30

Thr Pro Asn Ser Tyr Arg Val Arg Tyr Ser Leu Asn Val Gly Asp Ser
        35                  40                  45

Trp Val Leu Asp Met Gly Ala Thr Tyr Phe Asp Ile Lys Gly Val Leu
    50                  55                  60

Asp Arg Gly Pro Ser Phe Lys Pro Tyr Gly Gly Thr Ala Tyr Asn Pro
65                  70                  75                  80

Leu Ala Pro Arg Glu Ala Phe Phe Asn Asn Trp Ile Ala Glu Asp Gly
                85                  90                  95

Asn Lys Thr Thr Ile Thr Gly Gln Met Ser Asn Pro Tyr Glu Asn Thr
            100                 105                 110

Thr Gln Thr Ala Ala Ala Glu Thr Ala Ala Val Val Ala Ser Val Ser
        115                 120                 125

Gly Ser Tyr Pro Asn Pro Asn Ser Gly Pro Gly Ile Ser Glu Met Gly
    130                 135                 140

Ala Leu Ser Thr Thr Leu Ala Ala Gln Val Gly Leu Ala Gly Arg Phe
145                 150                 155                 160

Ala Lys Val Ser Ser Glu Asn Thr Arg Leu Ala Tyr Gly Ala Tyr Val
                165                 170                 175

Lys Pro Leu Lys Asn Asp Gly Ser Gln Ser Leu Val Gln Thr Pro Tyr
            180                 185                 190

Tyr Val Met Asp Ser Gly Ser Thr Lys Tyr Leu Gly Val Met Gly Val
        195                 200                 205

Glu Asp Phe Thr Asp Ser Leu Thr Tyr Pro Asp Ser Leu Leu Ile Pro
    210                 215                 220

Pro Pro Ile Glu Tyr Gly Thr Val Asn Thr Gly Val Met Lys Ala Asn
225                 230                 235                 240

Arg Pro Asn Tyr Ile Gly Phe Arg Asp Asn Phe Ile Asn Leu Leu Tyr
                245                 250                 255

His Asp Thr Gly Val Cys Ser Gly Thr Leu Asn Ser Glu Arg Ser Gly
            260                 265                 270

Met Asn Val Val Val Glu Leu Gln Asp Arg Asn Thr Glu Leu Ser Tyr
        275                 280                 285

Gln Tyr Met Leu Ala Asp Met Met Ser Arg His His
    290                 295                 300
```

<210> SEQ ID NO 11
<211> LENGTH: 902
<212> TYPE: DNA
<213> ORGANISM: fowl adenovirus
<220> FEATURE:
<221> NAME/KEY: misc_feature
<223> OTHER INFORMATION: FAdV08a_58

<400> SEQUENCE: 11

```
aagttcaggc agacggtggt cgcgcctacc cgcaatgtca ctaccgagaa ggcccagcgg      60
cttcagatca ggttctatcc cacccagacg gacgacaccc ccaacagtta ccgtgttcgg     120
tacagcttaa acgtggggga cagctgggtg ttggacatgg gagcgaccta cttcgacatc     180 aaagggggtgc tcgacagagg tccttccttc aagccctacg gcggcacggc ttacaacccc    240
ctggcccctc gcgaagcctt ctttaacaac tggatcgcgg aagacggcaa caagacaacc     300
atcaccgggc aaatgtctaa ccccctatgag aataccactc aaacggccgc agcggaaaca    360
gccgccgtcg tcgccagcgt ctccggcagc tacccctaatc ccaactcggg tccgggcatt    420
agcgaaatgg gggcgctcag caccacgcta gcggctcagg tcggtctagc cggtcgcttc     480
gcgaaagtat ccagcgagaa cacgcgtctg gcttacgggg cgtacgtcaa gcccctgaag     540
aacgacggct ctcagtctct ggtgcaaaca ccttactacg tcatggacag cgggagcacg     600
aaatatttgg gtgtgatggg ggtagaggac tttaccgata gcctgaccta ccccgacagt    660
ctactgatcc cgcctcctat cgagtacgga acggtcaata ccggggtgat gaaagctaac     720
agacccaatt acatcgggtt ccgtgacaat ttcatcaacc tcctgtacca cgataccggc     780
gtgtgctccg gcaccctgaa ctccgagcgg tccggcatga acgtggtcgt agaactgcag     840
gaccgaaaca ccgaactcag ttaccagtac atgctcgccg acatgatgtc ccggcatcac     900
ta                                                                    902

<210> SEQ ID NO 12
<211> LENGTH: 900
<212> TYPE: DNA
<213> ORGANISM: fowl adenovirus
<220> FEATURE:
<221> NAME/KEY: misc_feature
<223> OTHER INFORMATION: FAdV08a_8565

<400> SEQUENCE: 12
aagttcaggc agacggtggt cgcgcctacc cgcaatgtca ctaccgagaa ggcccagcgg      60
cttcagatca ggttctaccc cacccagacg gacgacaccc ccaacagtta ccgggttcgg     120
tacagcttaa acgtggggga cagctgggtg ttggacatgg gagcgaccta cttcgacatc     180 aaagggggtgc tcgacagagg tccttccttc aagccctacg gcggcacggc ttacaacccc    240
ctggcccctc gcgaagcctt ctttaacaac tggatcgcgg aagacggcaa caagacaacc     300
atcaccgggc aaatgtctaa ccccctatgag aataccactc aaacggccgc agcggaaaca    360
gccgccgtcg tcgccagcgt ctccggcagc tacccctaatc ccaactcggg tccgggcatt    420
agcgaaatgg gggcgctcag caccacgcta gcggctcagg tcggtctagc cggtcgcttc     480
gcgaaagtat ccagcgagaa cacgcgtctg gcttacgggg cgtacgtcaa gcccctgaag     540
aacgacggct ctcagtctct ggtgcaaaca ccttactacg tcatggacag cgggagcacg     600
aaatatttgg gtgtgatggg ggtagaggac tttaccgata gcctgaccta ccccgacagt    660
ctactgatcc cgcctcctat cgagtacgga acggtcaata ccggggtgat gaaagccaac     720
agacccaatt acatcgggtt ccgtgacaat ttcatcaacc tcctgtacca cgataccggc     780
gtgtgctccg gcaccctgaa ctccgagcgg tccggcatga acgtggtcgt agaactgcag     840
gaccgaaaca ccgaactcag ttaccagtac atgctcgccg acatgatgtc caggcatcac     900

<210> SEQ ID NO 13
<211> LENGTH: 300
<212> TYPE: PRT
<213> ORGANISM: fowl adenovirus
<220> FEATURE:
```

<221> NAME/KEY: MISC_FEATURE
<223> OTHER INFORMATION: FAdV08a_T8-A, ATCC VR-830

<400> SEQUENCE: 13

```
Lys Phe Arg Gln Thr Val Val Ala Pro Thr Arg Asn Val Thr Thr Glu
1               5                   10                  15

Lys Ala Gln Arg Leu Gln Ile Arg Phe Tyr Pro Thr Gln Thr Asp Asp
            20                  25                  30

Thr Pro Asn Ser Tyr Arg Val Arg Tyr Ser Leu Asn Val Gly Asp Ser
        35                  40                  45

Trp Val Leu Asp Met Gly Ala Thr Tyr Phe Asp Ile Lys Gly Val Leu
    50                  55                  60

Asp Arg Gly Pro Ser Phe Lys Pro Tyr Gly Gly Thr Ala Tyr Asn Pro
65                  70                  75                  80

Leu Ala Pro Arg Glu Ala Phe Phe Asn Asn Trp Ile Glu Asp Asp Gly
                85                  90                  95

Asn Asn Thr Thr Ile Thr Gly Gln Met Thr Asn Pro Tyr Lys Asn Glu
            100                 105                 110

Ala Gln Asn Thr Ala Thr Ala Thr Ala Ala Ile Ala Ser Val Ser
        115                 120                 125

Gly Ser Tyr Pro Asn Pro Asn Val Gly Leu Ala Ile Ser Glu Met Gly
    130                 135                 140

Ala Leu Thr Pro Thr Leu Ala Ala Gln Val Gly Leu Ala Gly Arg Phe
145                 150                 155                 160

Ala Lys Val Ser Asn Glu Asn Thr Arg Leu Ala Tyr Gly Ala Tyr Val
                165                 170                 175

Lys Pro Leu Lys Asp Asp Gly Ser Gln Ser Leu Gly Thr Thr Pro Tyr
            180                 185                 190

Tyr Val Leu Asp Thr Thr Ala Gln Lys Tyr Leu Gly Val Met Val Val
        195                 200                 205

Glu Asp Phe Thr Gln Ser Leu Thr Tyr Pro Asp Ser Leu Leu Ile Pro
    210                 215                 220

Pro Pro Ser Glu Tyr Gly Glu Val Asn Ser Gly Val Met Lys Ala Asn
225                 230                 235                 240

Arg Pro Asn Tyr Ile Gly Phe Arg Asp Asn Phe Ile Asn Leu Leu Tyr
                245                 250                 255

His Asp Thr Gly Val Cys Ser Gly Thr Leu Asn Ser Glu Arg Ser Gly
            260                 265                 270

Met Asn Val Val Val Glu Leu Gln Asp Arg Asn Thr Glu Leu Ser Tyr
        275                 280                 285

Gln Tyr Met Leu Ala Asp Met Met Ser Arg His His
    290                 295                 300
```

<210> SEQ ID NO 14
<211> LENGTH: 902
<212> TYPE: DNA
<213> ORGANISM: fowl adenovirus
<220> FEATURE:
<221> NAME/KEY: misc_feature
<223> OTHER INFORMATION: FAdV08a_T8-A, ATCC VR-830

<400> SEQUENCE: 14

```
aagttcaggc agacggtggt cgcgcctacc cgcaatgtca ctaccgagaa ggcccagcgg    60
cttcagatca ggttctatcc cacccagacg gacgacaccc ccaacagtta ccgggttcgg   120
tacagcttaa acgtggggga cagctgggtg ttggacatgg agcgacctta cttcgacatc   180
aaaggggtgc tcgacagagg tccttccttc aagccctacg gcggcacggc ttacaacccc   240
```

```
ctggcccctc gcgaagcctt ctttaacaac tggatcgagg acgatggaaa caacacaacc    300
atcacgggac aaatgaccaa tccgtacaag aacgaggcgc aaaacacagc tacggcaaca    360
gctgcagcaa tcgccagcgt ttcaggctct tatcctaacc ctaacgtggg gctggccatt    420
agcgaaatgg gagccctcac cccgacacta gcagcacagg tcggtttggc cggtcggttt    480
gccaaggtgt ccaatgagaa cacgcgcctg gcttatggag cgtatgtgaa gcctctaaaa    540
gacgacggct ctcagtcact tggaacaacg ccttactacg tgttagacac cacagcacag    600
aaatacttgg gcgtcatggt ggtagaagac tttacgcaaa gtcttaccta cccagacagt    660
ctgttaatcc cccctccttc tgagtacgga gaggttaaca gcggggtgat gaaagcgaac    720
agacccaact acatcgggtt ccgtgacaat ttcatcaacc tcctgtacca cgataccggc    780
gtgtgctccg ggaccctcaa ctccgaacgg tcaggcatga acgtggtggt ggaattgcag    840
gaccgaaaca ccgaactcag ctaccagtac atgctcgccg atatgatgtc ccggcatcac    900
ta                                                                    902
```

<210> SEQ ID NO 15
<211> LENGTH: 902
<212> TYPE: DNA
<213> ORGANISM: fowl adenovirus
<220> FEATURE:
<221> NAME/KEY: misc_feature
<223> OTHER INFORMATION: FAdV08a_TR59

<400> SEQUENCE: 15

```
aagttcaggc agacggtggt cgcgcctacc cgcaatgtca ctaccgagaa ggcccagcgg     60
cttcagatca ggttctaccc cacccagacg gacgacaccc caacagcta ccgggttcgg    120 tacagcctaa acgtggggga cagctgggtg ttggacatgg gagcgaccta cttcgacatc    180 aaagggtgc tcgacagagg tccttccttc aagcccacg gcggcacggc ttacaacccc    240
ctggcccctc gcgaagcctt ctttaacaac tggatcgcgg aagacggcaa caagacaacc    300 atcaccggc aaatgtctaa ccctatgag aataccactc aaacggccgc agcggaaaca    360
gccgccgtcg tcgccagcgt ctccggcagc taccctaatc ccaactcggg tccgggcatt    420
agcgaaatgg gggcgctcag cactacgcta gcggctcagg tcggtctagc cggtcgcttc    480
gcgaaagtat ccagcgagaa cacgcgtctg gcttacgggg cgtacgtcaa gcccctgaag    540
aacgacggct ctcagtctct ggtgcaaaca ccttactacg tcatggacag cgggagcacg    600
aaatatttgg gtgtgatggg ggtagaggac tttaccgata gcctgaccta ccccgacagt    660
ctactgatcc cgcctcctat cgagtacgga acggtcaata ccggggtgat gaaagctaac    720
agacccaatt acatcgggtt ccgtgacaat ttcatcaacc tcctgtacca cgataccggc    780
gtgtgctccg gcaccctgaa ctccgagcgg tccggcatga acgtggtcgt agaactgcag    840
gaccgaaaca ccgaactcag ttaccagtac atgctcgccg acatgatgtc ccggcatcac    900
ta                                                                    902
```

<210> SEQ ID NO 16
<211> LENGTH: 902
<212> TYPE: DNA
<213> ORGANISM: fowl adenovirus
<220> FEATURE:
<221> NAME/KEY: misc_feature
<223> OTHER INFORMATION: FAdV08b_764

<400> SEQUENCE: 16

```
aagttcaggc agacggtggt cgcgcctacc cgcaatgtca ctaccgagaa ggcccagcgg     60
```

-continued

```
cttcagatca ggttctatcc cacccagacg gacgacaccc ccaacagtta ccgtgttcgg      120
tacagcttaa acgtgggga cagctgggtg ttggacatgg gagcgaccta cttcgacatc      180 aaagggtgc tcgacagagg tccttccttc aagccttacg gcggcacggc ttacaacccc      240
ctggcccctc gcgaagcctt ctttaacaac tggatcgagg acgatggaaa caacacaacc      300
atcacgggac aaatgaccaa tccgtacaag aacgaggcgc aaaacacagc tacggcaaca      360
gctgcagcaa tcgccagcgt ttcaggctct tatcctaacc ctaacgtggg gctgggcatt      420
agcgaaatgg gagccctcac cccgacacta gcagcacagg tcggtctggc cggtcggttt      480
gccaaggtgt cgaatgagaa cacgcgcctg gcttatggag cgtatgtgaa gcctctaaaa      540
gacgacggct ctcagtcact tggaacaacg ccttactacg tgttagacac caccgcacag      600
aaatacttgg gcgtcatggg ggtagaagac tttacgcaaa gtcttaccta cccagacagt      660
ctgttaatcc cccctccttc tgagtacgga gaggttaaca gcggggtgat gaaagcgaac      720
agacccaact acatcgggtt ccgtgacaat ttcatcaacc tcctgtacca cgataccggc      780
gtgtgctccg ggaccctcaa ctccgaacgg tcaggcatga acgtggtggt ggaattgcag      840
gaccgaaaca ccgaactcag ctaccagtac atgctcgccg atatgatgtc ccgtcatcac      900
ta                                                                    902
```

<210> SEQ ID NO 17
<211> LENGTH: 300
<212> TYPE: PRT
<213> ORGANISM: fowl adenovirus
<220> FEATURE:
<221> NAME/KEY: MISC_FEATURE
<223> OTHER INFORMATION: FAdV08b_B3-A, ATCC VR-832

<400> SEQUENCE: 17

```
Lys Phe Arg Gln Thr Val Val Ala Pro Thr Arg Asn Val Thr Thr Glu
1               5                   10                  15

Lys Ala Gln Arg Leu Gln Ile Arg Phe Tyr Pro Thr Gln Thr Asp Asp
                20                  25                  30

Thr Pro Asn Ser Tyr Arg Val Arg Tyr Ser Leu Asn Val Gly Asp Ser
            35                  40                  45

Trp Val Leu Asp Met Gly Ala Thr Tyr Phe Asp Ile Lys Gly Val Leu
    50                  55                  60

Asp Arg Gly Pro Ser Phe Lys Pro Tyr Gly Gly Thr Ala Tyr Asn Pro
65                  70                  75                  80

Leu Ala Pro Arg Glu Ala Phe Phe Asn Asn Trp Ile Glu Asp Asp Glu
                85                  90                  95

Asn Lys Thr Ser Ile Thr Gly Gln Met Thr Asn Pro Tyr Thr Asn Asn
            100                 105                 110

Pro Gln Asn Thr Pro Thr Ala Thr Ala Thr Ile Ala Ser Val Ser
        115                 120                 125

Gly Ser Tyr Pro Asn Pro Asn Val Gly Pro Gly Ile Ser Glu Met Gly
    130                 135                 140

Ala Leu Thr Pro Thr Leu Ala Ala Gln Val Gly Leu Ala Gly Arg Phe
145                 150                 155                 160

Ala Lys Val Ser Ser Glu Asn Thr Arg Leu Ala Tyr Gly Ala Tyr Val
                165                 170                 175

Lys Pro Leu Lys Asn Asp Gly Ser Gln Ser Leu Ser Ala Thr Pro Tyr
            180                 185                 190

Tyr Val Leu Asp Ser Thr Ser Thr Asn Tyr Leu Gly Val Met Gly Val
        195                 200                 205
```

```
Glu Asp Phe Thr Gln Ser Leu Thr Tyr Pro Asp Ser Leu Leu Ile Pro
        210                 215                 220

Pro Pro Ser Glu Tyr Ser Glu Val Asn Ser Gly Val Met Lys Ala Asn
225                 230                 235                 240

Arg Pro Asn Tyr Ile Gly Phe Arg Asp Asn Phe Ile Asn Leu Leu Tyr
                245                 250                 255

His Asp Thr Gly Val Cys Ser Gly Thr Leu Asn Ser Glu Arg Ser Gly
            260                 265                 270

Met Asn Val Val Val Glu Leu Gln Asp Arg Asn Thr Glu Leu Ser Tyr
        275                 280                 285

Gln Tyr Met Leu Ala Asp Met Met Ser Arg His His
    290                 295                 300
```

<210> SEQ ID NO 18
<211> LENGTH: 902
<212> TYPE: DNA
<213> ORGANISM: fowl adenovirus
<220> FEATURE:
<221> NAME/KEY: misc_feature
<223> OTHER INFORMATION: FAdV08b_B3-A, ATCC VR-832

<400> SEQUENCE: 18

```
aagttcaggc agacggtggt cgcgcctacc cgcaatgtca ctaccgagaa ggcccagcgg    60
cttcagatca ggttctatcc cacccagacg gacgacaccc ccaacagtta ccgtgttcgg   120
tacagcttaa cgtgggggga cagctgggtg ctggacatgg agcgacccta cttcgacatc   180
aaagggtgtg tcgacagagg tccttccttc aagccctacg gcggcacggc ttacaacccc   240
ctggcccctc gcgaagcctt ctttaacaac tggatcgagg acgatgaaaa caagacatcc   300
atcacggggc aaatgaccaa tccgtacacg aacaacccgc aaaatacacc tacggcaaca   360
gctacggcaa tcgccagcgt ttcaggctct tatcctaacc ctaacgtggg accgggcatt   420
agcgaaatgg gagccctcac cccgacactc gcagcacagg ttggcctggc cggacgcttt   480
gccaaggtgt cgagcgagaa cacgcgtctg gcttacgggg cgtacgtcaa gcccctgaag   540
aatgacggtt cacagtcact gagtgcgaca ccatactacg tgttggacag cacgagtact   600
aactacctgg tgtgatggg agtagaggac ttcacgcaaa gcctcacgta ccccgacagt   660
ctcctgattc cgcctccttc cgagtacagt gaggttaaca gcggggtgat gaaggccaac   720
agacccaact acatcgggtt ccgggacaat ttcatcaact tgctgtatca cgataccggc   780
gtgtgctccg ggaccctcaa ctctgaacgg tccggcatga acgtggtcgt agaattgcag   840
gaccgaaaca ccgaactcag ttaccagtac atgctcgccg atatgatgtc ccgtcatcac   900
ta                                                                 902
```

<210> SEQ ID NO 19
<211> LENGTH: 798
<212> TYPE: DNA
<213> ORGANISM: fowl adenovirus
<220> FEATURE:
<221> NAME/KEY: misc_feature
<223> OTHER INFORMATION: 09-005853_FAdV08a-Stanford_HH_AW

<400> SEQUENCE: 19

```
cagcggcttc agatcaggtt ctaccccacc cagacggacg acaccccaa cagttaccgc    60
gttcggtaca gcttaaacgt gggggacagc tgggtgttgg acatgggagc gacctacttc   120
gacatcaaag gggtgctcga cagaggtcct tccttcaagc cctacggcgg cacggcttac   180
aaccccctgg cccctcgcga agccttcttt aacaactgga tcgaggacga tggaaacaac   240
```

```
acaaccatca cgggacaaat gaccaatccg tacaagaacg aggcgcaaaa cacagctacg    300
gcaacagctg cagcaatcgc cagcgtttca ggctcttatc ctaacccta  cgtggggctg    360 gccattagcg aagtgggagc cctcaccccg acactagcag cgcaggtcgg tctggccggt    420
cggtttgcca aggtgtccaa tgagaacacg cgcctggctt atggagcgta tgtgaagcct    480
ctaaaagacg acggctctca gtcacttgga acaacgcctt actacgtgtt agacaccaca    540
gcacagaaat acttgggcgt catgggggta gaagacttta cgcaaagtct tacctaccca    600
gacagtctgt taatccccc tccttctgag tacggagagg ttaacagcgg ggtgatgaaa     660
gcgaacagac ccaactacat cgggttccgt gacaatttca tcaacctcct gtaccacgat    720
accggcgtgt gctccgggac cctcaactcc gaacggtcag gcatgaacgt ggtggtggaa    780
ttgcaggacc gaaacacc                                                  798

<210> SEQ ID NO 20
<211> LENGTH: 837
<212> TYPE: DNA
<213> ORGANISM: fowl adenovirus
<220> FEATURE:
<221> NAME/KEY: misc_feature
<223> OTHER INFORMATION: 09-082363_FAdV08a-Stanford_PHS

<400> SEQUENCE: 20
cagcggcttc agatcaggtt ctaccccacc cagacggacg acaccccca  cagttaccgc     60 gttcggtaca gcttaaacgt gggggacagc tgggtgttgg acatgggagc gacctacttc    120
gacatcaaag gggtgctcga cagaggtcct tccttcaagc cctacggcgg cacggcttac    180 aacccctgg  cccctcgcga agccttcttt aacaactgga tcgaggacga tggaaacaac    240
acaaccatca cgggacaaat gaccaatccg tacaagaacg aggcgcaaaa cacagctacg    300
gcaacagctg cagcaatcgc cagcgtttca ggctcttatc ctaacccta  cgtggggctg    360 gccattagcg aagtgggagc cctcaccccg acactagcag cacaggtcgg tctggccggt    420
cggtttgcca aggtgtccaa tgagaacacg cgcctggctt atggagcgta tgtgaagcct    480
ctaaaagacg acggctctca gtcacttgga acaacgcctt actacgtgtt agacaccaca    540
gcacagaaat acttgggcgt catgggggta gaagacttta cgcaaagtct tacctaccca    600
gacagtctgt taatccccc tccttctgag tacggagagg ttaacagcgg ggtgatgaaa     660
gcgaacagac ccaactacat cgggttccgt gacaatttca tcaacctcct gtaccacgat    720
accggcgtgt gctccgggac cctcaactcc gaacggtcag gcatgaacgt ggtggtggaa    780
ttgcaggacc gaaacaccga actcagctac cagtacatgc tcgccgatat gatgtcc       837

<210> SEQ ID NO 21
<211> LENGTH: 1301
<212> TYPE: DNA
<213> ORGANISM: fowl adenovirus
<220> FEATURE:
<221> NAME/KEY: misc_feature
<223> OTHER INFORMATION: 04-53357-74 (FAdV08ab)

<400> SEQUENCE: 21
accgagaagg cccagcggct tcagatcagg ttctatccca cccagacgga cgacaccccc     60
aacagttacc gggttcggta cagcttaaac gtgggggaca gctgggtgtt ggacatggga    120
gcgacctact tcgacatcaa aggggtgctc gacagaggtc cttccttcaa gccctacggc    180
ggcacggctt acaacccct  ggcccctcgc gaagccttct ttaacaactg gatcgaggac    240
gatggaaaca acacaaccat cacgggacaa atgaccaatc cgtacaagaa cgaggcgcaa    300
```

```
aacacagcta cggcaacagc tgcagcaatc gccagcgttt caggctctta tcctaaccct    360 aacgtgggc  tggccattag cgaaatggga gccctcaccc cgacactagc agcacaggtc    420
ggtctggccg gtcggtttgc caaggtgtcg aatgagaaca cgcgcctggc ttatggagcg    480
tatgtgaagc ctctaaaaga cgacggctct cagtcacttg gaacaacgcc ttactacgtg    540
ttagacacca ccgcacagaa atacttgggc gtcatggggg tagaagactt tacgcaaagt    600
cttacctacc cagacagtct gttaatcccc cctccttctg agtacggaga ggttaacagc    660
ggggtgatga aagcgaacag acccaactac atcgggttcc gtgacaattt catcaacctc    720
ctgtaccacg ataccggcgt ctgctccggg accctcaact ccgaacgctc aggcatgaac    780
gtggtggtgg aattgcagga ccgaaacacc gaactcagct accagtacat gctcgccgat    840
atgatgtcca ggcatcacta tttcgctctc tggaaccagg ccgtggatca gtacgaccac    900
gacgtgcgcg tgtttaacaa cgacggctac gaggagggcg tgcccacgta cgccttctcg    960
cccgaggtaa caggacaggg tcccatcagt tcggcaaata tcacgctttc tggtgtcaag    1020
gtgtacacta acgtcagaa  cgacaagggc accgaagtca caaatcttac aacgtacctc    1080
aatgccggcg ccgtgccttc ctacgagatc gatctggcgg cctcccagcg gcgtaattt     1140 atcatcacca acatcgccga ctacctgccc gataagtaca agtacagcat gccgggttc     1200 aaccccgaaa ccgataacgt ggaccccacc acttacgcgt acatgaacag gagggtgccc    1260
ctgaccaacg tggtggattc tgttaccaac atcgggccag a                       1301

<210> SEQ ID NO 22
<211> LENGTH: 22
<212> TYPE: DNA
<213> ORGANISM: Artificial Sequence
<220> FEATURE:
<223> OTHER INFORMATION: Synthetic oligodeoxynucleotide

<400> SEQUENCE: 22
tcgtcgttgt cgttttgtcg tt                                              22

<210> SEQ ID NO 23
<211> LENGTH: 797
<212> TYPE: DNA
<213> ORGANISM: fowl adenovirus
<220> FEATURE:
<221> NAME/KEY: misc_feature
<223> OTHER INFORMATION: Majority
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t

<400> SEQUENCE: 23
cagcggcttc agatcaggtt ctatcccacc cagacggacg acaccccca  cagttaccgg     60 gttcggtaca gcttaaacgt gggggacagc tgggtgttgg acatgggagc gacctacttc    120
gacatcaaag gggtgctcga cagaggtcct tccttcaagc cctacggcgg cacggcttac    180
aaccccctgg cccctcgcga agccttcttt aacaactgga tcgaggacga tggaaacaac    240
acaaccatca cgggacaaat gaccaatccg tacaagaacg aggcgcaaaa cacagctacg    300
gcaacagctg cagcaatcgc cagcgtttca ggctcttatc ctaaccctaa cgtgggctg     360 gncattagcg aaatgggagc cctcaccccg acactagcag cacaggtcgg tctggccggt    420
```

-continued

```
cggtttgcca aggtgtccan tgagaacacg cgcctggctt atggagcgta tgtgaagcct      480
ctaaaagacg acggctctca gtcacttgga acaacgcctt actacgtgtt agacaccacg      540
gcacagaaat acttgggcgt catgggggta gaagacttta cgcaaagtct tacctaccca      600
gacagtctgt taatccccc tccttctgag tacgagagg ttaacagcgg ggtgatgaaa        660
gcgaacagac ccaactacat cgggttccgt gacaatttca tcaacctcct gtaccacgat      720
accggcgtgt gctccgggac cctcaactcc gaacggtcag gcatgaacgt ggtggtggaa      780
ttgcaggacc gaaacac                                                    797
```

We claim:

1. A composition or vaccine composition comprising: an isolated live and/or killed fowl adenovirus FAdV-8a/8b serotype strain; and a second FAdV serotype strain selected from FAdV-2, FAdV-7, FAdV-8a, FAdV-8b and/or FAdV-11 serotype strains, optionally a FAdV D species strain, wherein the composition provides heterologous protection against one or more FAdV serotype strains in addition to the strains and/or serotypes comprised in the composition.

2. The composition of claim 1, wherein the FAdV-8a/8b serotype strain comprises FAdV hexon L1 loop sequence selected from any one of SEQ ID NO: 5 and 6 and a sequence with at feast 99.0%, 99.1%, 99.2%, 99.3%, 99.4%, 99.5%, 99.6%, 99.7%, 99.8%, or 99.9% identity with any one of SEQ: NOs: 5 and 6; and/or the second FAdV serotype strain comprises a FAdV hexon L1 loop sequence selected from any one of SEQ ID NOs: 1-4 and 7-8 and a sequence with at least 99.0%, 99.1%, 99.2%, 99.3%, 99.4%, 99.5%, 99.6%, 99.7%, 99.8%, or 99.9% identity with any one of SEQ ID NOs: 1-4 and 7-8.

3. The composition of claim 1, wherein the second FAdV serotype strain comprises a FAdV-7 hexon L1 loop sequence selected from SEQ ID NO: 1, SEQ ID NO: 2, and a sequence that is the complement of SEQ ID NO: 2; wherein the second FAdV serotype strain comprises a FAdV-8a hexon L1 loop sequence selected from SEQ ID NO: 3, SEQ ID NO: 4, and a sequence that is the complement of SEQ ID NO: 4; wherein the FAdV-8a/8b strain comprises a hexon L1 loop sequence selected from SEQ ID NO: 5, SEQ ID NO 6, and a sequence that is the complement of SEQ ID NO: 6; and/or wherein the second FAdV serotype strain comprises a FAdV-11 hexon L1 loop sequence is selected from SEQ ID NO: 7, SEQ ID NO: 8 and a sequence that is the complement of SEQ ID NO: 8.

4. The composition of claim 1, wherein the FAdV-7 serotype strain is selected from x-11 and x11a strain, wherein the FAdV-8a serotype strain is selected from TR-59 and T8-A strain, and/or wherein the FAdV-11 serotype strain is selected from 380 and 1047 strain.

5. The composition of claim 1 wherein the FAdV-8/8b serotype strain is FAdV-8a/8b isolate 04-53357-74 deposited under Accession number 081210-02; and/or the second FAdV serotype strain is selected from, FAdV x11a-like isolate 04-53357-119 deposited under Accession number 081210-01; FAdV-8a strain TR-59 isolate 04-53357-125 deposited under Accession number 081210-03 and FAdV-11 isolate 06-58730 deposited under Accession number 081210-04.

6. The composition of claim 1, wherein the FAdV-8a/8b and/or the second FAdV serotype strain is comprised in liver homogenate.

7. The composition of claim 1, wherein the composition does not comprise a FAdV Esurient strain.

8. The composition of claim 1, wherein the FAdV-8a/8b serotype strain and the second FAdV serotype strain are live and/or attenuated.

9. The composition of claim 1, wherein the FAdV-8a/8b serotype strain is FAdV-8a/8b isolate 04-55357-74 deposited under Accession number 081210-02 and the composition optionally comprises an immunologically effective amount of the FAdV-8a/8b isolate.

10. The composition of claim 1 wherein, the composition comprises at least $0.1 \times 10^6$ CCID$_{50}$, at least $0.2 \times 10^6$ CCID$_{50}$, at least $0.4 \times 10^6$ CCID$_{50}$, at least $0.6 \times 10^6$ CCID$_{50}$, at least $0.8 \times 10^6$ CCID$_{50}$, at least $0.1 \times 10^6$ CCID$_{50}$, at least $1 \times 10^6$ CCID$_{50}$, at least $2 \times 10^6$ CCID$_{50}$, or at least $3 \times 10^6$ CCID$_{50}$, of the FAdV-8a/8b and/or the second FAdV serotype strain virus per dose.

11. The composition of claim 1, provided in a single or multidose formulation suitably formulated as a liquid formulation, a solid formulation or a spray formulation, for oral, intranasal, eye drop, intramuscular, intradermal, subcutaneous, intravenous and/or in ovo administration.

12. The composition of claim 11, wherein the oral administration is via drinking water and/or combined with food, and the intranasal administration is via spray.

13. The composition of claim 1, wherein the composition further comprises a particulate delivery system, optionally microparticles, immunostimulatory complexes (ISCOMs) or liposomes.

14. The composition of claim 1, wherein the composition is provided in combination with one or more poultry vaccines.

15. The composition of claim 1, wherein the FAdV-8a/8b and the second FAdV is killed, and the composition further an adjuvant.

16. The composition of claim 1, wherein the hexon L1 loop sequence of the FAdV-8a/8b serotype strain has at least 92.3% sequence identity to SEQ ID NO: 6.

17. The composition of claim 15, wherein the adjuvant is CpG-ODN.

18. The composition of claim 1, wherein the second FAdV serotype strain is a FAdV-11 serotype strain.

19. The composition of claim 1, wherein the second FAdV serotype strain is a FAdV-2 serotype strain.

20. The composition of claim 2, wherein the second FAdV serotype strain is a FAdV-11 serotype strain.

21. The composition of claim 3, wherein the second FAdV serofvpe strain is a FAdV-11 serotype strain.

22. The composition of claim 5, wherein the second FAdV serotype strain is a FAdV-11 serotype strain.

23. The composition of claim 9, wherein the second serotype strain is FAdV-11 isolate 06-58730 deposited under Accession number 081210-04.

24. A method of making a composition of claim 1 comprising:
a) propagating the FAdV-8a/8b strain according to the following method:
   i) inoculating a chicken embryonic liver cell culture with the FAdV-8a/8b strain;
   ii) incubating the cell culture at about 30-39° C. to allow the FAdV-8a/8b strain to propagate; and
   iii) isolating the propagated FAdV-8a/8b strain; and
b) formulating the propagated FAdV-8a/8b in combination with a second FAdV serotype strain selected from FAdV-2, FAdV-7, FAdV-8a, FAdV-8b and/or FAdV-11 serotype strains, optionally a FAdV D species strain, suitably for administration.

25. A kit comprising a composition of claim 1 and an instrument for administering the composition or vaccine, or comprising a commercial package comprising the composition comprised in a sterile container.

26. A method for eliciting an immune response in a subject, for producing antibodies in a subject and/or its progeny, or for inducing protective immunity against a FAdV related disease or syndrome in a subject and/or its progeny comprising administering an effective amount of a composition of claim 1 or a vaccine comprising said composition to the subject.

27. The method of claim 26, wherein the second FAdV strain is selected from:
(a) FADV-2, FADV-7, FADV-8a, and/or FAdV-11 serotype strain;
(b) FADV-2 serotype strain; or
(c) FAdV-11 serotype strain.

28. The method of claim 26, wherein the effective amount is effective to reduce mortality in FAdV progeny exposed to or challenged with FAdV by at least 20%, at least 30%, at least 40%, at least 50%, at least 60%, at least 70%, at least 80%, of least 90%, at least 95%, or about 99% compared to exposed or challenged non FAdV progeny.

29. The method of claim 26, wherein the FAdV related disease or syndrome is one or more of pneumonia and tracheitis, proventriculitis, inclusion body hepatitis (IBH) quail bronchitis, hydropericardium syndrome, gizzard erosions, and pancreatic necrosis.

30. The method of claim 26, wherein the effective amount of FAdV comprises at least $0.1 \times 10^6$ CCID$_{50}$, at least $0.2 \times 10^6$ CCID$_{50}$, at least $0.4 \times 10^6$ CCID$_{50}$, at least $0.6 \times 10^6$ CCID$_{50}$, at least $0.8 \times 10^6$ CCID$_{50}$, at least $0.1 \times 10^6$ CCID$_{50}$; at least $1 \times 10^6$ CCID$_{50}$, at least $2 \times 10^6$ CCID$_{50}$, or at least $3 \times 10^6$ CCID$_{50}$ of the FAdV-8a/8b and/or the second FAdV serotype strain virus per dose.

* * * * *

UNITED STATES PATENT AND TRADEMARK OFFICE
CERTIFICATE OF CORRECTION

PATENT NO.         : 8,524,249 B2
APPLICATION NO.    : 12/969444
DATED              : September 3, 2013
INVENTOR(S)        : Susantha Gomis et al.

It is certified that error appears in the above-identified patent and that said Letters Patent is hereby corrected as shown below:

In the Claims

1. Claim 9, column 78, line 20, "...serotype strain is FAdV-8a/8b isolate 04-55357-74 deposited..." should read --serotype strain is FAdV-8a/8b isolate 04-53357-74 deposited--.

2. Claim 15, column 78, line 47, "...and the second FAdV is killed, and the composition further an..." should read --and the second FAdV is killed, and the composition further comprises an--.

3. Claim 21, column 78, line 62, "....serofvpe strain is a FAdV-11 serotype strain." should read --serotype strain is a FAdV-11 serotype strain--.

Signed and Sealed this
Twelfth Day of November, 2013

Teresa Stanek Rea
*Deputy Director of the United States Patent and Trademark Office*